US012655225B2

(12) United States Patent
Huille et al.

(10) Patent No.: US 12,655,225 B2
(45) Date of Patent: Jun. 16, 2026

(54) FORMULATIONS OF ANTI-CD38 ANTIBODIES FOR SUBCUTANEOUS ADMINISTRATION

(71) Applicant: Sanofi-Aventis U.S. LLC, Bridgewater, NJ (US)

(72) Inventors: Sylvain Huille, Paris (FR); Thomas Ballet, Paris (FR); Kiran Bangari, Bridgewater, NJ (US); Ravi Chari, Bridgewater, NJ (US); Bernardo Perez-Ramirez, Bridgewater, NJ (US); Filipe Vasco, Paris (FR)

(73) Assignee: SANOFI-AVENTIS U.S. LLC, Bridgewater, NJ (US)

( * ) Notice: Subject to any disclaimer, the term of this patent is extended or adjusted under 35 U.S.C. 154(b) by 122 days.

(21) Appl. No.: 17/112,768

(22) Filed: Dec. 4, 2020

(65) Prior Publication Data

US 2021/0188996 A1 Jun. 24, 2021

Related U.S. Application Data

(60) Provisional application No. 62/944,082, filed on Dec. 5, 2019.

(51) Int. Cl.
*C07K 16/28* (2006.01)

(52) U.S. Cl.
CPC .... *C07K 16/2896* (2013.01); *C07K 2317/565* (2013.01); *C07K 2317/94* (2013.01)

(58) Field of Classification Search
CPC ............ C07K 16/2896; C07K 2317/94; C07K 2317/565
See application file for complete search history.

(56) References Cited

U.S. PATENT DOCUMENTS

| | | | |
|---|---|---|---|
| 5,064,413 A | 11/1991 | Mckinnon et al. | |
| 5,449,345 A | 9/1995 | Taylor et al. | |
| 5,460,944 A | 10/1995 | Franken et al. | |
| 5,954,695 A | 9/1999 | Sims et al. | |
| 6,428,509 B1 | 8/2002 | Fielder | |
| 6,587,845 B1 | 7/2003 | Braunheim | |
| 6,645,177 B1 | 11/2003 | Shearn | |
| 6,875,432 B2 | 4/2005 | Liu et al. | |
| 7,195,610 B1 | 3/2007 | Flachbart | |
| 8,231,576 B2 | 7/2012 | Sims et al. | |
| 8,420,081 B2 | 4/2013 | Fraunhofer et al. | |
| 8,814,830 B2 | 8/2014 | Morris et al. | |
| 9,306,965 B1 | 4/2016 | Grossman et al. | |
| 10,385,135 B2 * | 8/2019 | Jansson .................. A61K 45/06 | |
| 11,655,302 B2 | 5/2023 | Chiron-Blondel et al. | |
| 2008/0213282 A1 | 9/2008 | Jacob et al. | |
| 2010/0234246 A1 | 9/2010 | Jung et al. | |
| 2011/0302640 A1 | 12/2011 | Liu et al. | |
| 2012/0137367 A1 | 5/2012 | Dupont et al. | |
| 2013/0055404 A1 | 2/2013 | Khalili et al. | |
| 2013/0216525 A1 | 8/2013 | Chen et al. | |

| | | | |
|---|---|---|---|
| 2013/0216556 A1 | 8/2013 | Fowler et al. | |
| 2016/0058863 A1 | 3/2016 | Johnston et al. | |
| 2016/0376373 A1 | 12/2016 | Ahmadi et al. | |
| 2017/0049888 A1 | 2/2017 | Liu et al. | |
| 2017/0051039 A1 | 2/2017 | Gombotz et al. | |
| 2017/0121414 A1 | 5/2017 | Jansson et al. | |
| 2018/0000932 A1 | 1/2018 | Bansal | |
| 2018/0000935 A1 | 1/2018 | Parshad et al. | |
| 2018/0333493 A1 * | 11/2018 | Shenoy ............ A61K 39/39591 | |
| 2019/0233533 A1 | 8/2019 | Otten | |
| 2020/0399391 A1 | 12/2020 | Chiron Blondel et al. | |
| 2021/0155913 A1 | 5/2021 | Park et al. | |
| 2022/0218607 A1 | 7/2022 | Saluja et al. | |
| 2023/0323470 A1 | 10/2023 | Fury et al. | |
| 2023/0416395 A1 | 12/2023 | Chiron-Blondel et al. | |

FOREIGN PATENT DOCUMENTS

| | | | |
|---|---|---|---|
| EP | 2526963 A1 | 11/2012 | |
| EP | 3958898 A1 | 3/2022 | |
| EP | 3636752 A1 | 4/2022 | |
| WO | WO 2006/023148 A2 | 3/2006 | |
| WO | WO 2006/099875 A1 | 9/2006 | |
| WO | WO 2008/047242 A2 | 4/2008 | |
| WO | WO 2008/079290 A2 | 7/2008 | |
| WO | WO 2009/120684 A1 | 10/2009 | |

(Continued)

OTHER PUBLICATIONS

Almagro JC, Fransson J. Humanization of antibodies. Front Biosci. Jan. 1, 2008;13:1619-33. (Year: 2008).*

Kevzara (sarilumab). Package Insert. Sanofi Biotechnology; U.S. Food and Drug Administration website. https://www.accessdata.fda.gov/drugsatfda_docs/label/2018/761037s001lbl.pdf. Revised Apr. 2018. Accessed Aug. 14, 2024. (Year: 2018).*

Kang et al. Rapid Formulation Development for Monoclonal Antibodies. Bioprocess Technical 14(4), p. 40-45, Apr. 2016. (Year: 2016).*

Arnulf et al., "Updated survival analysis of a randomized phase III study of subcutaneous versus intravenous bortezomib in patients with relapsed multiple myeloma", Haematologica, 2012, vol. 97, No. 12, pp. 1925-1928.

(Continued)

*Primary Examiner* — Aurora M Fontainhas
*Assistant Examiner* — Jennifer A Benavides
(74) *Attorney, Agent, or Firm* — LATHROP GPM LLP; James H. Velema, Esq.

(57) ABSTRACT

Provided are formulations of anti-CD38 antibodies suitable for subcutaneous administration to a subject in need thereof. The formulations include a high concentration of antibody, a viscosity lowering agent, a stabilizing agent, a buffering agent and a surfactant. In certain embodiments, the viscosity of the solution is at most 25 mPa·s, and the pH of the solution is 5.9 to 7.0. In certain embodiments, the anti-CD38 antibody is isatuximab. The formulations will find use in treating CD38$^+$ hematological malignancies, including multiple myeloma, as well as autoimmune and inflammatory diseases, in humans.

31 Claims, 29 Drawing Sheets

Specification includes a Sequence Listing.

(56) References Cited

FOREIGN PATENT DOCUMENTS

| WO | WO 2010/061357 A1 | 6/2010 |
|----|---|---|
| WO | WO 2010/061358 A1 | 6/2010 |
| WO | WO 2010/061359 A1 | 6/2010 |
| WO | WO 2010/061360 A1 | 6/2010 |
| WO | WO 2012/076663 A1 | 6/2012 |
| WO | WO 2013/059885 A2 | 5/2013 |
| WO | WO 2014/074528 A2 | 5/2014 |
| WO | WO 2014/079886 A1 | 5/2014 |
| WO | WO 2014/089416 A1 | 6/2014 |
| WO | WO 2014/159911 A1 | 10/2014 |
| WO | WO 2015/066450 A1 | 5/2015 |
| WO | WO 2016/109822 A1 | 7/2016 |
| WO | WO 2017/079150 A1 | 5/2017 |
| WO | WO 2018/005881 A1 | 1/2018 |
| WO | WO 2018/007456 A1 | 1/2018 |
| WO | WO 2018/119142 A1 | 6/2018 |
| WO | WO 2018/119299 A1 | 6/2018 |
| WO | WO 2020/160020 A1 | 8/2020 |
| WO | WO 2020/216847 A1 | 10/2020 |
| WO | WO 2020/219681 A1 | 10/2020 |

OTHER PUBLICATIONS

Colombian Office Action No. 3725 regarding the Opposition filed by Laboratorios Legrand S.A. in parallel Columbian Patent Application No. NC2021/0015561, dated Mar. 22, 2022.

Derer et al., "Increasing FcγRIIa affinity of an FcγRIII-optimized anti-EGFR antibody restores neutrophil-mediated cytotoxicity", MAbs, Mar.-Apr. 2014, vol. 6, No. 2, pp. 409-421.

Dilillo et al., "Differential Fc-receptor engagement drives an anti-tumor vaccinal effect", Cell, May 21, 2015, vol. 161, No. 5, pp. 1035-1045.

Durie et al., "Bortezomib with lenalidomide and dexamethasone versus lenalidomide and dexamethasone alone in patients with newly diagnosed myeloma without intent for immediate autologous stem-cell transplant (SWOG S0777): a randomised, open-label, phase 3 trial", Lancet, Feb. 4, 2017, vol. 389, Issue 10068, pp. 519-527.

EMPLICITI® (elotuzumab) [package insert], U.S. Food and Drug Administration website, Obtained from: <www.accessdata.fda.gov/drugsatfda_docs/label/2018/761035s008lbl.pdf>, Revised Nov. 2018.

Gao et al., "Monoclonal antibody humanness score and its applications", BMC Biotechnology, Biomed Central Ltd., Jul. 5, 2013, vol. 13, No. 1, p. 55.

Graham et al., "Characteristics of a human cell line transformed by DNA from human adenovirus type 5", J. Gen Virol., Jul. 1977, vol. 36, No. 1, p. 59.

International Search Report and Written Opinion for PCT International Patent Application No. PCT/EP2020/061340, mailed Jul. 28, 2020.

International Search Report and Written Opinion for PCT International Patent Application No. PCT/US2020/029531, mailed Aug. 14, 2020.

Kumar et al., "Randomized, multicenter, phase 2 study (EVOLUTION) of combinations of bortezomib, dexamethasone, cyclophosphamide, and lenalidomide in previously untreated multiple myeloma", Blood, 2012, vol. 119, No. 19, pp. 4375-4382.

Lazar et al., "Engineered Antibody Fc Variants with Enhanced Effector Function", Proceedings of the National Academy of Sciences USA, Mar. 14, 2006, vol. 103, No. 11, pp. 4005-4010.

Lin et al., "Flow cytometric immunophenotypic analysis of 306 cases of multiple myeloma", Am J Clin Pathol., 2004, vol. 121, Issue 4, pp. 482-488.

Martin et al., "A phase 1b study of isatuximab plus lenalidomide and dexamethasone for relapsed/refractory multiple myeloma", Blood, 2017, vol. 129, No. 25, pp. 3294-3303.

Mather et al., "Culture of Testicular Cells in Hormone-Supplemented Serum-Free Medium", Annals of the NY Academy of Sciences, 1982, vol. 383, Issue 1, pp. 44-68.

Mather, "Establishment and characterization of two distinct mouse testicular epithelial cell lines", Biol. Reprod., 1980, vol. 23, No. 1, pp. 243-251.

Miltenyi Biotec, "CD14 MicroBeads human", Order No. 130-050-201, 2007, pp. 1-4.

Ocio et al., "Future agents and treatment directions in multiple myeloma", Expert Rev Hematol., 2014, vol. 7, No. 1, pp. 127-141.

Reinherz et al., "Discrete stages of human intrathymic differentiation: analysis of normal thymocytes and leukemic lymphoblasts of T-cell lineage", Proc Natl Acad Sci USA, Mar. 1980, vol. 77, No. 3, pp. 1588-1592.

Richards et al., "Optimization of antibody binding to FcgammaRIIa enhances macrophage phagocytosis of tumor cells", Mol Cancer Ther., Aug. 2008, vol. 7, No. 8, pp. 2517-2527.

Richardson et al., "A phase III randomized, open label, multicenter study comparing isatuximab, pomalidomide, and low-dose dexamethasone versus pomalidomide and low-dose dexamethasone in patients with relapsed/refractory multiple myeloma (RRMM)", Journal of Clinical Oncology, 2019, vol. 37, Issue 15, Supplement, Abstract 8004.

Richardson et al., "Lenalidomide, bortezomib, and dexamethasone combination therapy in patients with newly diagnosed multiple myeloma", Blood, Aug. 5, 2010, vol. 116, No. 5, pp. 679-686.

Roussel et al., "Front-line transplantation program with lenalidomide, bortezomib, and dexamethasone combination as induction and consolidation followed by lenalidomide maintenance in patients with multiple myeloma: a phase II study by the Intergroupe Francophone du Myélome", J Clin Oncol., Sep. 2014, vol. 32, No. 25, pp. 2712-2717.

Shire et al., "Challenges in the Development of High Protein Concentration Formulations", Journal of Pharmaceutical Sciences, American Chemical Society and American Pharmaceutical Association, US, Jun. 2004, vol. 93, No. 6, pp. 1390-1402.

Smith et al., "Mouse model recapitulating human Fcγ receptor structural and functional diversity", Proc Natl Acad Sci USA, 2012, vol. 109, No. 16, pp. 6181-6186.

Touzeau et al., "Daratumumab for the treatment of multiple myeloma", Expert Opinion on Biological Therapy, 2017, vol. 17, Issue 7, pp. 887-893.

Tzogani et al., "EMA Review of Panobinostat (Farydak) for the Treatment of Adult Patients with Relapsed and/or Refractory Multiple Myeloma", Oncologist, 2018, vol. 23, Issue 5, pp. 631-636.

Urlaub et al., "Isolation of Chinese hamster cell mutants deficient in dihydrofolate reductase activity", Proc. Natl. Acad. Sci. USA, 1980, vol. 77, No. 7, pp. 4216-4220.

Wang et al., "IgG Fc engineering to modulate antibody effector functions", Protein & Cell, Oct. 6, 2017, vol. 9, No. 1, pp. 63-73.

Yazaki et al., Methods in Molecular Biology, 2003, vol. 248, pp. 255-268.

Baek et al., "Effects of Histidine and sucrose on the Biophysical Properties of a Monoclonal Antibody", Pharmaceutical Research, Dec. 29, 2016, 34(3): 629-639.

Daugherty et al., "Chapter 8: Formulation and Delivery Issues for Monoclonal Antibody Therapeutics", Current Trends in Monoclonal Antibody Development and Manufacturing, Jan. 1, 2010, pp. 103-129.

He et al., "Effect of Sugar Molecules on the Viscosity of High Concentration Monoclonal Antibody Solutions", Pharmaceutical Research, May 15, 2011, 28(7): 1552-1560.

International Search Report and Written Opinion for PCT International Patent Application No. PCT/US2020/063452, mailed Mar. 18, 2021, 15 pages.

Kumar et al., "International Myeloma Working Group consensus criteria for response and minimal residual disease assessment in multiple myeloma", Lancet Oncol., Aug. 2016, 17(8): e328-e346.

Oken et al., "Toxicity and response criteria of the Eastern Cooperative Oncology Group", Am. J. Clin. Oncol., Dec. 1982, 5(6): 649-655.

Shu et al., "Blockade of CD38 diminishes lipopolysaccharide-induced macrophage classical activation and acute kidney injury involving NF-κB signaling suppression", Cell Signal, Jan. 2018, 42: 249-258.

(56)                    References Cited

OTHER PUBLICATIONS

Wang et al., "Viscosity-Lowering Effect Amino Acids and Salts on Highly Concentrated Solutions of Two IgG1 Monoclonal Antibodies", Molecular Pharmaceutics, Dec. 7, 2015, 12(12): 4478-4487.

Wang et al., "Antibody Structure, Instability, and Formulation", American Chemical Society and American Pharmaceutical Association, US, Jan. 1, 2007, 96(1): 1-26.

Begum et al., "Investigating the Influence of Polysorbate 20/80 and Polaxomer P188 on the Surface & Interfacial Properties of Bovine Serum Albumin and Lysozyme", Pharm. Res., May 20, 2019, 36(7): 107.

Parmar et al., "Efficacy and safety of isatuximab subcutaneous (SC) plus carfilzomib and dexamethasone (Isa-Kd) in patients with relapsed/refractory multiple myeloma (RRMM): Results of the phase 2 study IZALCO", J. Clin. Oncol., Meeting Abstract: 2025 ASCO Annual Meeting, Poster PS1726, May 28, 2025.

Quach et al., Letter to the Editor, "A multicenter, phase Ib study of subcutaneous administration of isatuximab in combination with pomalidomide and dexamethasone in patients with relapsed/refractory multiple myeloma", Haematologica, Dec. 2024, 109(12): 4078-4082.

Chang et al., LIBSVM—A Library for Support Vector Machines. 2001, http://vvwwicsio.ntu.edb..twi-cjiiMibsvin.

Clinicaltrials.gov, "Multinational Clinical Study Comparing Isatuximab, Pomalidomide, and Dexamethasone to Pomalidomide and Dexamethasone in Refractory or Relapsed and Refractory Multiple Myeloma Patients (ICARIA-MM)", ClinicalTrials.gov ID NCT02990338, Dec. 8, 2016.

Cui et al., "Computer prediction of appergen proteins from sequence-derived protein structural and physiochemical properties", Molecular Immunology, 2007, 44: 514-520.

Duckert et at, Prediction of proprotein convertase cleavage sites, Protein Engineering, Design and Selector vol. 17, 2004, pp. 107-112.

Dziuba et al. Database of biologically active peptide sequences, Nahrung, 1999, vol. 43, No. 3, pp. 190-195.

European Examination Report for European Patent Application No. 20720057.7, mailed Feb. 5, 2024.

Falciani et al Bioactive Peptides from Libraries, Chemistry & Biology, vol. 12, Issue 4, 2005, pp. 417-426.

International Search Report and Written Opinion for PCT International Patent Application No. PCT/EP2008/001687, mailed Jun. 29, 2009.

Jones, Protein. Secondary Structure Prediction Based on Position-specific Scoring Matrices, J. Wi. Biol. vol. 292 1999. pp. 195-202.

Kim et al., Prediction of Protein Relative Solvent Accessibility with Support Vector Machines and Long-Range Interaction 3D Local Descriptor, PROTEINS: Structure, Function, and Bioinformatics, vol. 54, 2004, pp. 557-556.

Mei et al., "A new set of amino acid descriptors and its application in peptide QSARs", Biopolymers, May 13, 2005, 80: 775-786.

Nathoo et al., Identification of nebropeptide-like protein gene families in Caenorhabditis elegans end other species, PNAS, vol. 98, No. 24, Nov. 20, 2001: pp. 14000-14005.

Nielsen et al., Identification of prokaryotic and eukaryotic signal peptides and prediction of their cleavage sites, Protein Engineering, vol. 20, No. 1 1997, pp. 1-6.

Noble, W., What is a support vector machine?, Nature Biotechnology, vol. 24, No. 1 Dec. 2006, pp. 1565-1567.

Solov'Ev et al., "Anti-HIV Activity of HEPT, TIBO, and Cyclic Urea Derivatives: Structure-Property Studies, Focused Combinatorial Library Generation, and Hits Selection Using Substructural Molecular Fragments Method", Journ Chem Inf Comput Sci., 2003, 43(5): 1703-1719.

European Examination Report for European Patent Application No. 20720057.7, mailed Mar. 27, 2026.

* cited by examiner

FORMULATIONS OF ANTI-CD38 ANTIBODIES FOR SUBCUTANEOUS ADMINISTRATION

RELATED APPLICATIONS

This application claims priority to U.S. Provisional Patent Application Ser. No. 62/944,082, filed Dec. 5, 2019, the entire disclosure of which is hereby incorporated herein by reference.

SEQUENCE LISTING

The instant application contains a Sequence Listing which has been submitted electronically in ASCII format and is hereby incorporated by reference in its entirety. Said ASCII copy, created on Dec. 4, 2020, is named 712538_SA9-295_ST25.txt and is 9,561 bytes in size.

FIELD OF THE INVENTION

The present disclosure concerns formulations of antibodies useful in the treatment of disease. More specifically, it relates to formulations of anti-CD38 antibodies suitable for use in subcutaneous administration for treating cancers, including multiple myeloma, as well as other diseases and conditions in which CD38$^+$ cells play a role.

BACKGROUND

CD38 is a 45 kDa type II transmembrane glycoprotein with a long C-terminal extracellular domain and a short N-terminal cytoplasmic domain. The CD38 protein is a bifunctional ectoenzyme that can catalyze the conversion of NAD$^+$ into cyclic ADP-ribose (cADPR) and also hydrolyze cADPR into ADP-ribose.

CD38 is upregulated in many hematological malignancies and in cell lines derived from various hematological malignancies. Furthermore, most primitive pluripotent stem cells of the hematological system are CD38$^-$. CD38 expression in hematological malignancies and its correlation with disease progression in chronic lymphocytic leukemia (CLL) makes CD38 an attractive target for antibody therapy.

CD38$^+$ cells are also reported to be associated with various other diseases and conditions, including many autoimmune diseases such as rheumatoid arthritis and lupus erythematosus, and lipopolysaccharide (LPS)- or sepsis-induced acute kidney injury (Shu B et al., *Cell Signal* (2018) 42: 249-58).

Anti-CD38 antibodies, which specifically recognize CD38, have been previously described, for example in the international patent application WO2006/099875. However, these antibodies fail to induce apoptosis when used as a single agent and incubated with CD38$^+$ expressing cells.

Monoclonal anti-CD38 antibodies have been described in international patent application WO2008/047242.

The use of these specific anti-CD38 antibodies in combination with cytotoxic agents, such as cytarabine, vincristine, cyclophosphamide and melphalan, has been reported in international patent applications WO2010/061357, WO2010/061358, WO2010/061359, and WO2010/061360.

International patent applications WO2015/066450, WO2012/076663, and WO2014/089416, WO2014/159911, also describe the use of the humanized version of 38SB19 (also known as SAR650984 or Isatuximab). A phase 3 clinical trial (NCT02990338) of isatuximab in combination with pomalidomide and dexamethasone for the treatment of patients with relapsed/refractory multiple myeloma recently met its primary endpoint, prolonged progression-free survival.

SUMMARY OF THE INVENTION

An aspect of the present disclosure relates to formulations of an anti-CD38 antibody suitable for subcutaneous administration to a subject. Advantageously, the formulations disclosed herein are suitable for subcutaneous administration, either by injection or infusion, including large-volume subcutaneous infusion. The formulations can be used in the treatment of a disease or condition characterized by CD38-expressing cells. Such diseases and conditions include, without limitation, CD38 expressing solid tumors, such as prostate cancer, various hematological malignancies, such as non-Hodgkin's lymphoma (NHL), multiple myeloma (MM), acute myeloid leukemia (AML), acute lymphoblastic leukemia (B-cell ALL) and/or chronic lymphocytic leukemia (CLL). Such diseases and conditions further include, without limitation, autoimmune diseases including rheumatoid arthritis and systemic lupus erythematosus, and lipopolysaccharide (LPS)- or sepsis-induced acute kidney injury.

In certain embodiments, the present disclosure relates to a formulation of an anti-CD38 antibody comprising a high concentration of the antibody, a pH of 5.9-7.0, and a viscosity of at most 25 mPa·s at 20° C.

In certain embodiments, the present disclosure relates to a formulation comprising at least 100 mg/mL of an anti-CD38 antibody, a viscosity reducing agent, a stabilizer, a buffering agent, and a surfactant, wherein the formulation has a pH of 5.9-7.0 and a viscosity of at most 25 mPa·s at 20° C.

An aspect of the present disclosure relates to a formulation comprising at least 100 mg/mL of an anti-CD38 antibody, wherein the anti-CD38 antibody comprises a variable heavy region (VH) comprising three complementarity determining regions (CDRs) CDR-H1, CDR2-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises a viscosity reducing agent, a stabilizer, a buffering agent, and a surfactant, and the formulation has a pH of 5.9-7.0 and a viscosity of at most 25 mPa·s at 20° C.

In certain embodiments, the viscosity reducing agent is 90-150 mM Arg-Cl.

In certain embodiments, the viscosity reducing agent is 90-125 mM Arg-Cl.

In certain embodiments, the viscosity reducing agent is 110 mM Arg-Cl.

In certain embodiments, the surfactant is Poloxamer 188.

In certain embodiments, the surfactant is 0.4% (w/v) Poloxamer 188.

In certain embodiments, the buffering agent is histidine.

In certain embodiments, the buffering agent is 9 mM histidine.

In certain embodiments, the viscosity reducing agent is 90-150 mM Lys-Ac.

In certain embodiments, the viscosity reducing agent is 125 mM Lys-Ac.

In certain embodiments, the surfactant is Polysorbate 80.

In certain embodiments, the surfactant is 0.04% (w/v) Polysorbate 80.

In certain embodiments, the formulation comprises 125-155 mg/mL of the anti-CD38 antibody.

In certain embodiments, the formulation comprises 140 mg/mL of the anti-CD38 antibody.

In certain embodiments, the stabilizer is sucrose.

In certain embodiments, the stabilizer is 2% (w/v) sucrose.

In certain embodiments, the pH is 5.9-7.0.

In certain embodiments, the pH is 5.9-6.5.

An aspect of the present disclosure relates to a formulation comprising 140 mg/mL of an anti-CD38 antibody, wherein the anti-CD38 antibody comprises a variable heavy region (VH) comprising three complementarity determining regions (CDRs) CDR-H1, CDR-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises 9 mM histidine, 110 mM Arg-Cl, 2% (w/v) sucrose, and 0.4% (w/v) Poloxamer 188, and wherein the formulation has a pH of 6.2 and a viscosity of at most 14 mPa·s at 20° C.

An aspect of the present disclosure relates to a formulation comprising 140 mg/mL of an anti-CD38 antibody, wherein the anti-CD38 antibody comprises a variable heavy region (VH) comprising three complementarity determining regions (CDRs) CDR-H1, CDR-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises 125 mM Lys-Ac, 2% (w/v) sucrose, and 0.04% (w/v) Polysorbate 80, and the formulation has a pH of 6.2 and a viscosity of at most 14 mPa·s at 20° C.

In certain embodiments, the formulation is suitable for subcutaneous administration by either injection or infusion including large volume sub-cutaneous infusion.

In certain embodiments, VH of the anti-CD38 antibody comprises the amino acid sequence set forth in SEQ ID NO: 7, and the VL of the anti-CD38 antibody comprises the amino acid sequence set forth in SEQ ID NO: 8.

In certain embodiments, the anti-CD38 antibody is isatuximab.

An aspect of the present disclosure relates to a packaged pharmaceutical product comprising a sterile container comprising a therapeutically effective amount of a formulation of the present disclosure.

An aspect of the present disclosure relates to a device comprising a therapeutically effective amount of a formulation of the present disclosure.

In certain embodiments, the device can be, for example, a syringe, a syringe driver, and an infusion pump comprising the formulation.

In certain embodiments, the syringe is a pre-filled syringe.

An aspect of the present disclosure is a method of treating a disease or condition characterized by presence or activity of CD38⁺ cells, comprising administering to a subject in need thereof an effective amount of a formulation of the disclosure, wherein the formulation is administered subcutaneously.

In certain embodiments, the disease or condition characterized by the presence or activity of CD38⁺ cells is a CD38⁺ hematological malignancy.

In certain embodiments, the disease or condition characterized by the presence or activity of CD38⁺ cells is an autoimmune or inflammatory disease or condition.

An aspect of the present disclosure is a method of treating a CD38⁺ hematological malignancy, comprising administering to a subject in need thereof an effective amount of a formulation of the present disclosure, wherein the formulation is administered subcutaneously.

An aspect of the present disclosure is a method of treating a CD38⁺ hematological malignancy, comprising administering to a subject in need thereof an effective amount of a formulation of an anti-CD38 antibody comprising at least 100 mg/mL of an anti-CD38 antibody, wherein the anti-CD38 antibody comprises a variable heavy region (VH) comprising three complementarity determining regions (CDRs) CDR-H1, CDR-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises a viscosity reducing agent, a stabilizer, a buffering agent, and a surfactant, and the formulation has a pH of 5.5-7.0 and a viscosity of at most 25 mPa·s at 20° C., wherein the formulation is administered subcutaneously.

An aspect of the present disclosure is a method of treating a CD38⁺ hematological malignancy, comprising administering to a subject in need thereof an effective amount of a formulation of an anti-CD38 comprising 140 mg/mL of an anti-CD38 antibody, wherein the anti-CD38 antibody comprises a variable heavy region (VH) comprising three complementarity determining regions (CDRs) CDR-H1, CDR-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises 9 mM histidine, 110 mM Arg-Cl, 2% (w/v) sucrose, and 0.4% (w/v) Poloxamer 188, and wherein the formulation has a pH of 6.2 and a viscosity of at most 14 mPa·s at 20° C., wherein the formulation is administered subcutaneously.

In certain embodiments, the method comprises administering to the subject in need thereof an effective amount of a formulation comprising 140 mg/mL of an anti-CD38 antibody, wherein the anti-CD38 antibody comprises a variable heavy region (VH) comprising three complementarity determining regions (CDRs) CDR-H1, CDR-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises 9 mM histidine, 110 mM Arg-Cl, 2% (w/v) sucrose, and 0.4% (w/v) Poloxamer 188, and wherein the formulation has a pH of 6.3 and a viscosity of at most 14 mPa·s at 20° C., wherein the formulation is administered subcutaneously.

In certain embodiments, the formulation is administered by subcutaneous infusion.

In certain embodiments, the formulation is administered by subcutaneous infusion.

In certain embodiments, the subcutaneous infusion is a large-volume subcutaneous infusion, e.g., from >2 mL to 30 mL.

In certain embodiments, the method of treating a CD38+ hematological malignancy further comprises administering to the subject one or more additional agents suitable for treating a C38+ hematological cancer. In some embodiments, the other agent is, for example, a corticosteroid (e.g., dexamethasone), a chemotherapy drug, a proteasome inhibitor, an immunomodulatory drug, or a combination thereof.

In certain embodiments, the chemotherapy drug is, for example, cytarabine, daunorubicin, daunomycin, doxorubicin, liposomal doxorubicin, idarubicin, mitoxantrone, gemtuzumab, clofarabine, cladribine, hydroxyurea, etoposide, amsacrine, a FLT3-inhibitor such as gilteritinib, 5-azacytidine, decitabine, melphalan, cyclophosphamide, or vincristine, or combinations thereof.

In certain embodiments, the immunomodulatory drug is, for example, thalidomide, lenalidomide, or pomalidomide, or combinations thereof.

In certain embodiments, the proteasome inhibitor is, for example, ixazomib, carfilzomib, or bortezomib, or combinations thereof.

In certain embodiments, the method of treating a CD38+ hematological malignancy comprises administering to the subject isatuximab formulated for subcutaneous administration as defined herein, and two or more additional agents from different classes of compounds, such as, for example, an immunomodulatory drug or a proteasome inhibitor.

In certain embodiments, the CD38+ hematological malignancy is multiple myeloma. In certain embodiments, the multiple myeloma is relapsed/refractory multiple myeloma. In some embodiments, the patient has received at least two previous therapies for multiple myeloma including lenalidomide and a proteasome inhibitor, and had demonstrated disease progression on last therapy or after completion of the last therapy.

DETAILED DESCRIPTION

Figure 1:
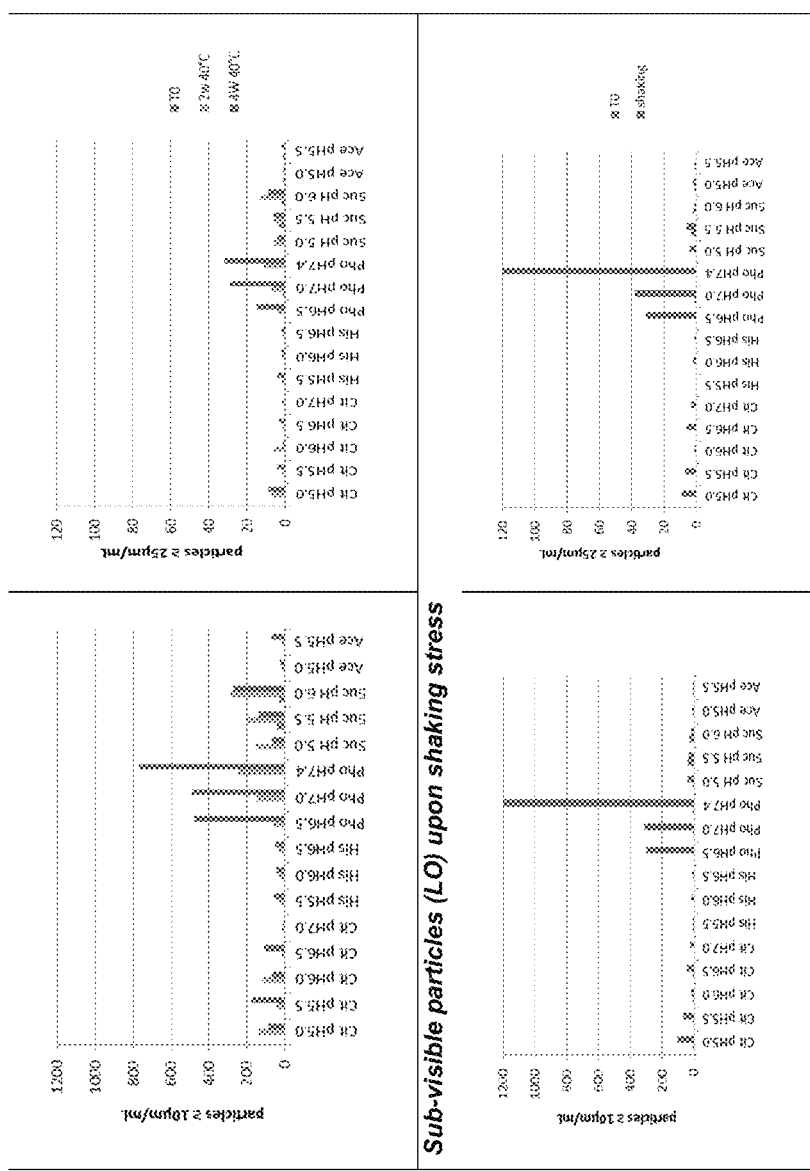
FIG. 1 is a series of graphs depicting the number of sub-visible particles $\geq 10$ μm and $\geq 25$ μm after thermal stress (upper panels) and shaking stress (lower panels) of isatuximab in the indicated buffer systems. 2 w 40° C., two weeks at 40° C.; 4 w 40° C., 4 weeks at 40° C.; Cit, citrate buffer; His, histidine buffer; Pho, phosphate buffer; Ace, acetate buffer.

Provided herein are formulations of an anti-CD38 antibody suitable for subcutaneous administration to a subject. Advantageously, the formulations disclosed herein are suitable for subcutaneous administration, either by injection or by infusion, including large-volume subcutaneous infusion. The formulations can be used in the treatment of a disease or condition characterized by CD38-expressing cells. Such diseases and conditions include, without limitation, various hematological malignancies, such as non-Hodgkin's lymphoma (NHL), multiple myeloma (MM), acute myeloid leukemia (AML), acute lymphoblastic leukemia (B-cell ALL) and/or chronic lymphocytic leukemia (CLL). Such diseases and conditions further include, without limitation, autoimmune diseases including rheumatoid arthritis and systemic lupus erythematosus, and lipopolysaccharide (LPS)- or sepsis-induced acute kidney injury. In certain embodiments, the formulations provided herein comprise a high concentration of the antibody, a pH of 5.5-7.0, and a viscosity of at most 25 mPa·s at 20° C. In some embodiments, provided herein, the formulation is an aqueous formulation.

"Hematological malignancies" are the types of cancer that affect blood, bone marrow, and lymph nodes. As the three are intimately connected through the immune system, a disease affecting one of the three might affect the others as well. Hematological malignancies include non-Hodgkin's lymphoma (NHL) (including, e.g. Burkitt's lymphoma (BL) and T-cell lymphoma (TCL)), multiple myeloma (MM), chronic lymphocytic leukemia (CLL) (such as, e.g., B-cell chronic lymphocytic leukemia (B-CLL) and hairy cell leukemia (HCL)), B- and T-cell acute lymphocytic leukemia (ALL), acute myeloid leukemia (AML), Hodgkin's lymphoma (HL), and chronic myeloid leukemia (CML). In some embodiments, the hematological malignancy is a $CD38^+$ hematological malignancy.

"$CD38^+$ hematological malignancy" is thus a hematological malignancy, as described above, wherein the cancerous cells express CD38. $CD38^+$ cells are also reported to be involved in many autoimmune and inflammatory diseases and disorders, including rheumatoid arthritis and systemic lupus erythematosus, as well as other conditions including LPS- or sepsis-induced acute kidney injury.

$CD38^+$ hematological malignancies include B-cell non-Hodgkin's lymphoma (NHL), multiple myeloma (MM), acute myeloid leukemia (AML), acute lymphoblastic leukemia (B-cell ALL) and/or chronic lymphocytic leukemia (CLL). In some embodiments, the $CD38^+$ hematological malignancy is MM. In some embodiments, the $CD38^+$ hematological malignancy is relapsed and/or refractory multiple myeloma.

An "antibody" may be a natural or conventional antibody in which two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgG, IgA, IgD, and IgE. Additionally, immunoglobulin subclasses (or sub-isotypes), e.g., IgG1, IgG2, IgG3, IgG4, IgA1, and IgA2, are well characterized and are known to confer functional specialization. Each chain contains distinct sequence domains. The light chain includes two domains or regions, a variable domain (VL) and a constant domain (CL). The heavy chain includes four domains, a variable domain (VH) and three constant domains (CH1, CH2, and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin which includes the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site.

"Complementarity Determining Regions" or "CDRs" refer to amino acid sequences which together define the binding specificity and affinity of the natural Fv region of a native immunoglobulin binding site. The light and heavy chains of an immunoglobulin each have three CDRs, designated CDR-L1, CDR-L2, CDR-L3 and CDR-H1, CDR-H2, CDR-H3, respectively. A conventional antibody antigen-binding site, therefore, includes six CDRs, comprising the CDR set from each of a heavy and a light chain V region.

CDR/FR definition concerning the immunoglobulin light or heavy chain are given based on the Kabat definition (worlwideweb.bioinforg.uk/abs/).

An antibody can also be a non-naturally occurring antibody, e.g., a monoclonal antibody, a chimeric antibody, or a humanized antibody. The term "monoclonal antibody" or "mAb" as used herein refers to an antibody molecule of a single amino acid composition that is directed against a specific antigen, and is not to be construed as requiring production of the antibody by any particular method. A monoclonal antibody may be produced by a single clone of B cells or hybridoma, but may also be recombinant, i.e., produced by protein engineering.

The term "humanized antibody" refers to an antibody which is initially wholly or partially of non-human origin and which has been modified to replace certain amino acids, for example, in the framework regions of the heavy and light chains, in order to avoid or minimize an immune response in humans. The constant domains of a humanized antibody can be, for example, human CH and CL domains. In an embodiment, a humanized antibody has constant domains of human origin.

In some embodiments, the anti-CD38 antibody according to the disclosure comprises a heavy chain comprising a CDR-H1 comprising the amino acid sequence set forth as SEQ ID NO: 1, a CDR-H2 comprising the amino acid sequence SEQ ID NO: 2, and a CDR-H3 comprising the amino acid sequence SEQ ID NO: 3, and a light chain comprising a CDR-L1 comprising the amino acid sequence set forth as SEQ ID NO: 4, a CDR-L2 comprising the amino acid sequence set forth as SEQ ID NO: 5, and a CDR-L3 comprising the amino acid sequence set forth as SEQ ID NO: 6.

```
CDR-H1
                           (SEQ ID NO: 1)
DYWMQ

CDR-H2
                           (SEQ ID NO: 2)
TIYPGDGDTGY AQKFQG

CDR-H3
                           (SEQ ID NO: 3)
GDYYGSNSLDY

CDR-L1
                           (SEQ ID NO: 4)
KASQDVSTVVA

CDR-L2
                           (SEQ ID NO: 5)
SASYRYI

CDR-L3
                           (SEQ ID NO: 6)
QQHYSPPYT
```

In some embodiments, said antibody comprises a heavy chain variable domain (VH) comprising the amino acid sequence set forth as SEQ ID NO: 7.

In some embodiments, said antibody comprises a light chain variable domain (VL) comprising the amino acid sequence set forth as SEQ ID NO: 8.

In some embodiments, said antibody comprises a heavy chain variable domain (VH) comprising the amino acid sequence set forth as SEQ ID NO: 7 and a light chain variable domain (VL) comprising the amino acid sequence set forth as SEQ ID NO: 8.

```
                           (SEQ ID NO: 7)
QVQLVQSGAEVAKPGTSVKLSCKASGYTFTDYWMQWVKQRPGQGLE

WIGTIYPGDGDTGYAQKFQGKATLTADKSSKTVYMHLSSLASEDSA

VYYCARGDYYGSNSLDYWGQGTSVTVSS
```

```
                           (SEQ ID NO: 8)
DIVMTQSHLSMSTSLGDPVSITCKASQDVSTVVAWYQQKPGQSPRR

LIYSASYRYIGVPDRFTGSGAGTDFTFTISSVQAEDLAVYYCQQHY

SPPYTFGGGTKLEIKR
```

In some embodiments, the anti-CD38 antibody according to the disclosure is isatuximab. The heavy chain (HC) of isatuximab comprises the amino acid sequence set forth as SEQ ID NO: 9, and the light chain (LC) of isatuximab comprises the amino acid sequence set forth as SEQ ID NO: 10.

```
                           (SEQ ID NO: 9)
QVQLVQSGAEVAKPGTSVKLSCKASGYTFTDYWMQWVKQRPGQGLE

WIGTIYPGDGDTGYAQKFQGKATLTADKSSKTVYMHLSSLASEDSA

VYYCARGDYYGSNSLDYWGQGTSVTVSSASTKGPSVFPLAPSSKST

SGGTAALGCLVKDYFPEPVTVSWNSGALTSGVHTFPAVLQSSGLYS

LSSVVTVPSSSLGTQTYICNVNHKPSNTKVDKKVEPKSCDKTHTCP

PCPAPELLGGPSVFLFPPKPKDTLMISRTPEVTCVVVDVSHEDPEV

KFNWYVDGVEVHNAKTKPREEQYNSTYRVVSVLTVLHQDWLNGKEY

KCKVSNKALPAPIEKTISKAKGQPREPQVYTLPPSRDELTKNQVSL

TCLVKGFYPSDIAVEWESNGQPENNYKTTPPVLDSDGSFFLYSKLT

VDKSRWQQGNVFSCSVMHEALHNHYTQKSLSLSPGK
```

```
                           (SEQ ID NO: 10)
DIVMTQSHLSMSTSLGDPVSITCKASQDVSTVVAWYQQKPGQSPRR

LIYSASYRYIGVPDRFTGSGAGTDFTFTISSVQAEDLAVYYCQQHY

SPPYTFGGGTKLEIKRTVAAPSVFIFPPSDEQLKSGTASVVCLLNN

FYPREAKVQWKVDNALQSGNSQESVTEQDSKDSTYSLSSTLTLSKA

DYEKHKVYACEVTHQGLSSPVTKSFNRGEC
```

In some embodiments, the antibody is for use in treating a CD38$^+$ hematological malignancy, such as multiple myeloma (MM), including relapsed and/or refractory MM or patients having MM who have received one or more prior therapies for MM.

In the context of the disclosure, the term "treating" or "treatment", as used herein, means reversing, alleviating, inhibiting the progress of, or preventing the disorder or condition to which such term applies, or one or more symptoms of such disorder or condition. In certain embodiments, the term "treating" or "treatment", as used herein, means reversing, alleviating, or inhibiting the progress of the disorder or condition to which such term applies, or one or more symptoms of such disorder or condition.

By the term "treating a CD38$^+$ hematological malignancy" as used herein is meant the inhibition of the growth of CD38$^+$ malignant cells of a tumor and/or the progression of metastases from said CD38$^+$ tumor. Such treatment can also lead to the regression of tumor growth, i.e., the decrease in size of a measurable tumor.

By a "therapeutically effective amount" of the antibody, in context of the disclosure, is meant a sufficient amount of the antibody to treat said CD38$^+$ hematological malignancy as disclosed herein.

In certain embodiments, said therapeutically effective amount of the antibody administered subcutaneously to the subject is a dose ranging from 500 mg to 2000 mg of antibody per dose.

In certain embodiments, said therapeutically effective amount of the antibody administered to the subject is 1000 mg of antibody per dose. In certain embodiments, said therapeutically effective amount of the antibody administered to the subject is 1400 mg of antibody per dose. In certain embodiments, said therapeutically effective amount of the antibody administered to the subject is 1600 mg of antibody per dose.

As used herein, the term "subject" refers to a mammal. In certain embodiments, the term "subject" refers to a human.

The antibody of the disclosure may be administered once a week (QW), once in two weeks (Q2W), or a combination of once a week and once in two weeks. In some embodiments, the antibody is administered once every four weeks.

For example, the antibody can be administered to the subject is a dose ranging from 500 mg to 1400 mg once a week for four weeks (cycle 1) followed by once every other week (e.g., on day 1 and day 15 of each subsequent four week cycle).

In some embodiments, 1000 mg of antibody is administered to the subject once a week for four weeks (cycle 1) and then 1000 mg of antibody is administered to the subject on days 1 and 15 of each subsequent four week cycle.

In some embodiments, 1000 mg of the antibody is administered to the subject once every other week.

In some embodiments, 1400 mg of the antibody is administered to the subject once a week for four weeks (cycle 1) and then 1400 mg of the antibody is administered on days 1 and 15 for each subsequent four week cycle.

In some embodiments, 1400 mg of the antibody is administered to the subject once every other week. In some embodiments, the antibody may be administered according to an intermittent program with an interval between each administration of 1 week or 2 weeks, which may be prolonged by 1 to 2 weeks depending on the tolerance to the preceding administration.

A "cycle" as used herein refers to 4 calendar weeks, i.e., 28 days. Administration "once a week" means once every 7 days. Administration "once in two weeks" means once every 14 days. Administration once a cycle or once every four weeks means once every 28 days.

In some embodiments, the number of cycles of antibody administration may be 2 to 50, such as 2, 3, 4, 5, 6, 7, 8, 9, 10, 12, 14, 16, 18, 20, 25, 30, 35, 45, 50 cycles.

Formulations of the Invention

The present disclosure provides certain formulations of anti-CD38 antibodies. In some embodiments, the formulations are liquid formulations. In certain embodiments, such formulations (antibody formulations) are suitable for administration to a subject in need of treatment with the anti-CD38 antibody.

Advantageously, the antibody formulations of the present disclosure can be administered to a subject subcutaneously either by injection or by infusion, including large-volume subcutaneous infusion.

In certain embodiments, the present disclosure relates to a formulation of an anti-CD38 antibody comprising a high concentration of the antibody, a pH of 5.5-7.0, and a viscosity of at most 25 mPa·s at 20° C.

In certain embodiments, the present disclosure relates to a formulation comprising at least 100 mg/mL of an anti-CD38 antibody, a viscosity reducing agent, a stabilizer, a buffering agent, and a surfactant, wherein the formulation has a pH of 5.5-7.0 and a viscosity of at most 25 mPa·s at 20° C.

In some embodiments, formulations of the antibody are provided comprising at least 100 mg/mL of an anti-CD38 antibody, wherein the anti-CD38 antibody comprises a variable heavy region (VH) comprising three complementarity determining regions (CDRs) CDR-H1, CDR-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises a viscosity reducing agent, a stabilizer, a buffering agent, and a surfactant, and the formulation has a pH of 5.5-7.0 and a viscosity of at most 25 mPa·s at 20° C.

In certain embodiments, the formulation comprises 125-155 mg/mL of the anti-CD38 antibody.

In certain embodiments, the formulation comprises 140 mg/mL of the anti-CD38 antibody.

In certain embodiments, the viscosity reducing agent is 90-150 mM Arg-Cl.

In certain embodiments, the viscosity reducing agent is 90-130 mM Arg-Cl.

In certain embodiments, the viscosity reducing agent is 110 mM Arg-Cl.

In certain embodiments, the stabilizer is sucrose.

In certain embodiments, the aqueous formulation comprises 125-155 mg/mL of the anti-CD38 antibody, 90-150 mM Arg-Cl, and sucrose.

In certain embodiments, the formulation comprises 140 mg/mL of the anti-CD38 antibody, 90-150 mM Arg-Cl, and sucrose.

In certain embodiments, the formulation comprises 125-155 mg/mL of the anti-CD38 antibody, 90-130 mM Arg-Cl, and sucrose.

In certain embodiments, the formulation comprises 125-155 mg/mL of the anti-CD38 antibody, 110 mM Arg-Cl, and sucrose.

In certain embodiments, the formulation comprises 140 mg/mL of the anti-CD38 antibody, 90-130 mM Arg-Cl, and sucrose.

In certain embodiments, the formulation comprises 140 mg/mL of the anti-CD38 antibody, 110 mM Arg-Cl, and sucrose.

In certain embodiments, the formulation comprises 2% (w/v) sucrose.

In certain embodiments, the formulation comprises 125-155 mg/mL of the anti-CD38 antibody, 90-150 mM Arg-Cl, and 2% (w/v) sucrose.

In certain embodiments, the formulation comprises 140 mg/mL of the anti-CD38 antibody, 90-130 mM Arg-Cl, and 2% (w/v) sucrose.

In certain embodiments, the formulation comprises 140 mg/mL of the anti-CD38 antibody, 110 mM Arg-Cl, and 2% (w/v) sucrose.

In certain embodiments, the formulation comprises a surfactant.

In certain embodiments, the surfactant is Poloxamer 188.

In certain embodiments, the viscosity reducing agent is 90-150 mM Arg-Cl, the stabilizer is sucrose, and the surfactant is Poloxamer 188.

In certain embodiments, the viscosity reducing agent is 90-150 mM Arg-Cl, the stabilizer is 2% (w/v) sucrose, and the surfactant is Poloxamer 188.

In certain embodiments, the solution comprises 125-155 mg/mL of the anti-CD38 antibody, 90-150 mM Arg-Cl, 2% (w/v) sucrose, and Poloxamer 188.

In certain embodiments, the solution comprises 140 mg/mL of the anti-CD38 antibody, 90-150 mM Arg-Cl, 2% (w/v) sucrose, and Poloxamer 188.

In certain embodiments, the viscosity reducing agent is 90-130 mM Arg-Cl, the stabilizer is sucrose, and the surfactant is Poloxamer 188.

In certain embodiments, the viscosity reducing agent is 110 mM Arg-Cl, the stabilizer is sucrose, and the surfactant is Poloxamer 188.

In certain embodiments, the viscosity reducing agent is 90-125 mM Arg-Cl, the stabilizer is 2% (w/v) sucrose, and the surfactant is Poloxamer 188.

In certain embodiments, the viscosity reducing agent is 110 mM Arg-Cl, the stabilizer is 2% (w/v) sucrose, and the surfactant is Poloxamer 188.

In certain embodiments, the solution comprises 125-155 mg/mL of the anti-CD38 antibody, 90-125 mM Arg-Cl, 2% (w/v) sucrose, and Poloxamer 188.

In certain embodiments, the solution comprises 125-155 mg/mL of the anti-CD38 antibody, 110 mM Arg-Cl, 2% (w/v) sucrose, and Poloxamer 188.

In certain embodiments, the solution comprises 140 mg/mL of the anti-CD38 antibody, 90-125 mM Arg-Cl, 2% (w/v) sucrose, and Poloxamer 188.

In certain embodiments, the solution comprises 140 mg/mL of the anti-CD38 antibody, 110 mM Arg-Cl, 2% (w/v) sucrose, and Poloxamer 188.

In certain embodiments, the formulation comprises 0.4% (w/v) Poloxamer 188.

In certain embodiments, the viscosity reducing agent is 90-150 mM Arg-Cl, the stabilizer is sucrose, and the surfactant is 0.4% (w/v) Poloxamer 188.

In certain embodiments, the viscosity reducing agent is 90-150 mM Arg-Cl, the stabilizer is 2% (w/v) sucrose, and the surfactant is 0.4% (w/v) Poloxamer 188.

In certain embodiments, the solution comprises 125-155 mg/mL of the anti-CD38 antibody, 90-150 mM Arg-Cl, 2% (w/v) sucrose, and 0.4% (w/v) Poloxamer 188.

In certain embodiments, the solution comprises 140 mg/mL of the anti-CD38 antibody, 90-150 mM Arg-Cl, 2% (w/v) sucrose, and 0.4% (w/v) Poloxamer 188.

In certain embodiments, the viscosity reducing agent is 90-125 mM Arg-Cl, the stabilizer is sucrose, and the surfactant is 0.4% (w/v) Poloxamer 188.

In certain embodiments, the viscosity reducing agent is 110 mM Arg-Cl, the stabilizer is sucrose, and the surfactant is 0.4% (w/v) Poloxamer 188.

In certain embodiments, the viscosity reducing agent is 90-125 mM Arg-Cl, the stabilizer is 2% (w/v) sucrose, and the surfactant is 0.4% (w/v) Poloxamer 188.

In certain embodiments, the viscosity reducing agent is 110 mM Arg-Cl, the stabilizer is 2% (w/v) sucrose, and the surfactant is 0.4% (w/v) Poloxamer 188.

In certain embodiments, the solution comprises 125-155 mg/mL of the anti-CD38 antibody, 90-125 mM Arg-Cl, 2% (w/v) sucrose, and 0.4% (w/v) Poloxamer 188.

In certain embodiments, the solution comprises 125-155 mg/mL of the anti-CD38 antibody, 110 mM Arg-Cl, 2% (w/v) sucrose, and 0.4% (w/v) Poloxamer 188.

In certain embodiments, the solution comprises 140 mg/mL of the anti-CD38 antibody, 90-125 mM Arg-Cl, 2% (w/v) sucrose, and 0.4% (w/v) Poloxamer 188.

In certain embodiments, the solution comprises 140 mg/mL of the anti-CD38 antibody, 110 mM Arg-Cl, 2% (w/v) sucrose, and 0.4% (w/v) Poloxamer 188.

In certain embodiments, the formulation comprises a buffering agent.

In certain embodiments, the buffering agent is histidine.

In certain embodiments, the viscosity reducing agent is 90-150 mM Arg-Cl, the stabilizer is sucrose, the surfactant is Poloxamer 188, and the buffering agent is histidine.

In certain embodiments, the viscosity reducing agent is 90-150 mM Arg-Cl, the stabilizer is 2% (w/v) sucrose, the surfactant is Poloxamer 188, and the buffering agent is histidine.

In certain embodiments, the viscosity reducing agent is 90-150 mM Arg-Cl, the stabilizer is 2% (w/v) sucrose, the surfactant is 0.4% (w/v) Poloxamer 188, and the buffering agent is histidine.

In certain embodiments, the solution comprises 125-155 mg/mL of the anti-CD38 antibody, 90-150 mM Arg-Cl, 2% (w/v) sucrose, 0.4% (w/v) Poloxamer 188, and histidine.

In certain embodiments, the solution comprises 140 mg/mL of the anti-CD38 antibody, 90-150 mM Arg-Cl, 2% (w/v) sucrose, 0.4% (w/v) Poloxamer 188, and histidine.

In certain embodiments, the viscosity reducing agent is 90-125 mM Arg-Cl, the stabilizer is sucrose, the surfactant is Poloxamer 188, and the buffering agent is histidine.

In certain embodiments, the viscosity reducing agent is 110 mM Arg-Cl, the stabilizer is sucrose, the surfactant is Poloxamer 188, and the buffering agent is histidine.

In certain embodiments, the viscosity reducing agent is 90-125 mM Arg-Cl, the stabilizer is 2% (w/v) sucrose, the surfactant is Poloxamer 188, and the buffering agent is histidine.

In certain embodiments, the viscosity reducing agent is 110 mM Arg-Cl, the stabilizer is 2% (w/v) sucrose, the surfactant is Poloxamer 188, and the buffering agent is histidine.

In certain embodiments, the viscosity reducing agent is 90-125 mM Arg-Cl, the stabilizer is 2% (w/v) sucrose, the surfactant is 0.4% (w/v) Poloxamer 188, and the buffering agent is histidine.

In certain embodiments, the viscosity reducing agent is 110 mM Arg-Cl, the stabilizer is 2% (w/v) sucrose, the surfactant is 0.4% (w/v) Poloxamer 188, and the buffering agent is histidine.

In certain embodiments, the solution comprises 125-155 mg/mL of the anti-CD38 antibody, 90-125 mM Arg-Cl, 2% (w/v) sucrose, 0.4% (w/v) Poloxamer 188, and histidine.

In certain embodiments, the solution comprises 125-155 mg/mL of the anti-CD38 antibody, 110 mM Arg-Cl, 2% (w/v) sucrose, 0.4% (w/v) Poloxamer 188, and histidine.

In certain embodiments, the solution comprises 140 mg/mL of the anti-CD38 antibody, 90-125 mM Arg-Cl, 2% (w/v) sucrose, 0.4% (w/v) Poloxamer 188, and histidine. In certain embodiments, the solution comprises 140 mg/mL of the anti-CD38 antibody, 110 mM Arg-Cl, 2% (w/v) sucrose, 0.4% (w/v) Poloxamer 188, and histidine.

In certain embodiments, the buffering agent is 9 mM histidine.

In certain embodiments, the viscosity reducing agent is 90-150 mM Arg-Cl, the stabilizer is sucrose, the surfactant is Poloxamer 188, and the buffering agent is 9 mM histidine.

In certain embodiments, the viscosity reducing agent is 90-150 mM Arg-Cl, the stabilizer is 2% (w/v) sucrose, the surfactant is Poloxamer 188, and the buffering agent is 9 mM histidine.

In certain embodiments, the viscosity reducing agent is 90-150 mM Arg-Cl, the stabilizer is 2% (w/v) sucrose, the surfactant is 0.4% (w/v) Poloxamer 188, and the buffering agent is 9 mM histidine.

In certain embodiments, the solution comprises 125-155 mg/mL of the anti-CD38 antibody, 90-150 mM Arg-Cl, 2% (w/v) sucrose, 0.4% (w/v) Poloxamer 188, and 9 mM histidine.

In certain embodiments, the solution comprises 140 mg/mL of the anti-CD38 antibody, 90-150 mM Arg-Cl, 2% (w/v) sucrose, 0.4% (w/v) Poloxamer 188, and 9 mM histidine.

In certain embodiments, the viscosity reducing agent is 90-125 mM Arg-Cl, the stabilizer is sucrose, the surfactant is Poloxamer 188, and the buffering agent is 9 mM histidine.

In certain embodiments, the viscosity reducing agent is 110 mM Arg-Cl, the stabilizer is sucrose, the surfactant is Poloxamer 188, and the buffering agent is 9 mM histidine.

In certain embodiments, the viscosity reducing agent is 90-125 mM Arg-Cl, the stabilizer is 2% (w/v) sucrose, the surfactant is Poloxamer 188, and the buffering agent is 9 mM histidine.

In certain embodiments, the viscosity reducing agent is 110 mM Arg-Cl, the stabilizer is 2% (w/v) sucrose, the surfactant is Poloxamer 188, and the buffering agent is 9 mM histidine.

In certain embodiments, the viscosity reducing agent is 90-125 mM Arg-Cl, the stabilizer is 2% (w/v) sucrose, the surfactant is 0.4% (w/v) Poloxamer 188, and the buffering agent is 9 mM histidine.

In certain embodiments, the viscosity reducing agent is 110 mM Arg-Cl, the stabilizer is 2% (w/v) sucrose, the surfactant is 0.4% (w/v) Poloxamer 188, and the buffering agent is 9 mM histidine.

In certain embodiments, the solution comprises 125-155 mg/mL of the anti-CD38 antibody, 90-125 mM Arg-Cl, 2% (w/v) sucrose, 0.4% (w/v) Poloxamer 188, and 9 mM histidine.

In certain embodiments, the solution comprises 125-155 mg/mL of the anti-CD38 antibody, 110 mM Arg-Cl, 2% (w/v) sucrose, 0.4% (w/v) Poloxamer 188, and 9 mM histidine.

In certain embodiments, the solution comprises 140 mg/mL of the anti-CD38 antibody, 90-125 mM Arg-Cl, 2% (w/v) sucrose, 0.4% (w/v) Poloxamer 188, and 9 mM histidine.

In certain embodiments, the solution comprises 140 mg/mL of the anti-CD38 antibody, 110 mM Arg-Cl, 2% (w/v) sucrose, 0.4% (w/v) Poloxamer 188, and 9 mM histidine.

In certain embodiments, the viscosity reducing agent is 90-150 mM Lys-Ac.

In certain embodiments, the viscosity reducing agent is 125 mM Lys-Ac.

In certain embodiments, the formulation comprises 125-155 mg/mL of the anti-CD38 antibody, 90-150 mM Lys-Ac, and sucrose.

In certain embodiments, the formulation comprises 140 mg/mL of the anti-CD38 antibody, 90-150 mM Lys-Ac, and sucrose.

In certain embodiments, the formulation comprises 125-155 mg/mL of the anti-CD38 antibody, 125 mM Lys-Ac, and sucrose.

In certain embodiments, the formulation comprises 140 mg/mL of the anti-CD38 antibody, 125 mM Lys-Ac, and sucrose.

In certain embodiments, the formulation comprises 125-155 mg/mL of the anti-CD38 antibody, 90-150 mM Lys-Ac, and 2% (w/v) sucrose.

In certain embodiments, the formulation comprises 140 mg/mL of the anti-CD38 antibody, 90-150 mM Lys-Ac, and 2% (w/v) sucrose.

In certain embodiments, the formulation comprises 125-155 mg/mL of the anti-CD38 antibody, 125 mM Lys-Ac, and 2% (w/v) sucrose.

In certain embodiments, the formulation comprises 140 mg/mL of the anti-CD38 antibody, 125 mM Lys-Ac, and 2% (w/v) sucrose.

In certain embodiments, the formulation comprises a surfactant.

In certain embodiments, the surfactant is Polysorbate 80.

In certain embodiments, the viscosity reducing agent is 90-150 mM Lys-Ac, the stabilizer is sucrose, and the surfactant is Polysorbate 80.

In certain embodiments, the formulation comprises 125-155 mg/mL of the anti-CD38 antibody, 90-150 mM Lys-Ac, sucrose, and Polysorbate 80.

In certain embodiments, the formulation comprises 140 mg/mL of the anti-CD38 antibody, 90-150 mM Lys-Ac, sucrose, and Polysorbate 80.

In certain embodiments, the viscosity reducing agent is 90-150 mM Lys-Ac, the stabilizer is 2% (w/v) sucrose, and the surfactant is Polysorbate 80.

In certain embodiments, the formulation comprises 125-155 mg/mL of the anti-CD38 antibody, 90-150 mM Lys-Ac, 2% (w/v) sucrose, and Polysorbate 80.

In certain embodiments, the formulation comprises 140 mg/mL of the anti-CD38 antibody, 90-150 mM Lys-Ac, 2% (w/v) sucrose, and Polysorbate 80.

In certain embodiments, the viscosity reducing agent is 125 mM Lys-Ac, the stabilizer is sucrose, and the surfactant is Polysorbate 80.

In certain embodiments, the formulation comprises 125-155 mg/mL of the anti-CD38 antibody, 125 mM Lys-Ac, sucrose, and Polysorbate 80.

In certain embodiments, the formulation comprises 140 mg/mL of the anti-CD38 antibody, 125 mM Lys-Ac, sucrose, and Polysorbate 80.

In certain embodiments, the viscosity reducing agent is 125 mM Lys-Ac, the stabilizer is 2% (w/v) sucrose, and the surfactant is Polysorbate 80.

In certain embodiments, the formulation comprises 125-155 mg/mL of the anti-CD38 antibody, 125 mM Lys-Ac, 2% (w/v) sucrose, and Polysorbate 80.

In certain embodiments, the formulation comprises 140 mg/mL of the anti-CD38 antibody, 125 mM Lys-Ac, 2% (w/v) sucrose, and Polysorbate 80.

In certain embodiments, the surfactant is 0.04% (w/v) Polysorbate 80.

In certain embodiments, the viscosity reducing agent is 90-150 mM Lys-Ac, the stabilizer is sucrose, and the surfactant is 0.04% (w/v) Polysorbate 80.

In certain embodiments, the formulation comprises 125-155 mg/mL of the anti-CD38 antibody, 90-150 mM Lys-Ac, sucrose, and 0.04% (w/v) Polysorbate 80.

In certain embodiments, the formulation comprises 140 mg/mL of the anti-CD38 antibody, 90-150 mM Lys-Ac, sucrose, and 0.04% (w/v) Polysorbate 80.

In certain embodiments, the viscosity reducing agent is 90-150 mM Lys-Ac, the stabilizer is 2% (w/v) sucrose, and the surfactant is 0.04% (w/v) Polysorbate 80.

In certain embodiments, the formulation comprises 125-155 mg/mL of the anti-CD38 antibody, 90-150 mM Lys-Ac, 2% (w/v) sucrose, and 0.04% (w/v) Polysorbate 80.

In certain embodiments, the formulation comprises 140 mg/mL of the anti-CD38 antibody, 90-150 mM Lys-Ac, 2% (w/v) sucrose, and 0.04% (w/v) Polysorbate 80.

In certain embodiments, the viscosity reducing agent is 125 mM Lys-Ac, the stabilizer is sucrose, and the surfactant is 0.04% (w/v) Polysorbate 80.

In certain embodiments, the formulation comprises 125-155 mg/mL of the anti-CD38 antibody, 125 mM Lys-Ac, sucrose, and 0.04% (w/v) Polysorbate 80.

In certain embodiments, the formulation comprises 140 mg/mL of the anti-CD38 antibody, 125 mM Lys-Ac, sucrose, and 0.04% (w/v) Polysorbate 80.

In certain embodiments, the viscosity reducing agent is 125 mM Lys-Ac, the stabilizer is 2% (w/v) sucrose, and the surfactant is 0.04% (w/v) Polysorbate 80.

In certain embodiments, the formulation comprises 125-155 mg/mL of the anti-CD38 antibody, 125 mM Lys-Ac, 2% (w/v) sucrose, and 0.04% (w/v) Polysorbate 80.

In certain embodiments, the formulation comprises 140 mg/mL of the anti-CD38 antibody, 125 mM Lys-Ac, 2% (w/v) sucrose, and 0.04% (w/v) Polysorbate 80.

In certain embodiments, the pH of the formulation is 5.9-7.0.

In certain embodiments, the pH of the formulation is 5.9-6.5.

In certain embodiments, the pH of the formulation is 6.2.

In some embodiments, the formulation comprise 140 mg/mL of an anti-CD38 antibody, wherein the anti-CD38 antibody comprises a variable heavy region (VH) comprising three complementarity determining regions (CDRs) CDR-H1, CDR-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises 9 mM histidine, 110 mM Arg-Cl, 2% (w/v) sucrose, and 0.4% (w/v) Poloxamer 188, and wherein the formulation has a pH of 6.2-6.3 and a viscosity of at most 14 mPa·s at 20° C.

An aspect of the present disclosure relates to an formulation comprising 140 mg/mL of an anti-CD38 antibody, wherein the anti-CD38 antibody comprises a variable heavy region (VH) comprising three complementarity determining regions (CDRs) CDR-H1, CDR-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises 125 mM Lys-Ac, 2% (w/v) sucrose, and 0.04 (w/v) Polysorbate 80, and the formulation has a pH of 6.2 and a viscosity of at most 14 mPa·s at 20° C.

In accordance with each of the foregoing aspects and embodiments, in certain embodiments, the VH of the anti-CD38 antibody comprises amino acid sequence set forth in SEQ ID NO: 7.

In accordance with each of the foregoing aspects and embodiments, in certain embodiments, the VL of the anti-CD38 antibody comprises the amino acid sequence set forth in SEQ ID NO: 8.

In accordance with each of the foregoing aspects and embodiments, in certain embodiments, the VH of the anti-CD38 antibody comprises amino acid sequence set forth in SEQ ID NO: 7, and the VL of the anti-CD38 antibody comprises the amino acid sequence set forth in SEQ ID NO: 8.

In accordance with each of the foregoing aspects and embodiments, in certain embodiments, the anti-CD38 antibody is isatuximab.

In accordance with each of the foregoing aspects and embodiments, the formulation further comprises water, for example water for injection (WFI), in an amount sufficient to achieve the specified concentrations of other ingredients.

In accordance with each of the foregoing aspects and embodiments, in certain embodiments, the formulation is suitable for subcutaneous administration. For example, the formulation can be sterile. In certain embodiments, the components of the formulation can be combined to form a solution and then the solution can be sterile filtered to provide the sterile formulation.

In certain embodiments, the finished formulation is substantially free of dissolved oxygen. For example, the formulation can be equilibrated with nitrogen gas and then sealed under nitrogen atmosphere.

Yet further in accordance with each of the foregoing aspects and embodiments, in certain embodiments the formulation can further comprise at least one additional excipient or component for improved stability, e.g., a preservative agent.

Packaged Pharmaceutical Products

An aspect of the present disclosure relates to a packaged pharmaceutical product comprising a sterile container comprising a single dose of the formulation of the present disclosure. Suitable sterile containers include, without limitation, vials, ampoules, bottles, bags, pouches, pre-filled syringes, syringe drivers, infusion pumps, and containers adapted for use with syringe drivers and/or infusion pumps. Suitable containers include single-use containers and multiple-use containers. In certain embodiments, a container is a single-use container, e.g., a vial containing the antibody in an amount corresponding to a single dose.

A syringe driver as used herein refers to a mechanical or pneumatic device constructed and arranged to engage a plunger of a syringe and drive it axially forward and/or backward so as to cause the contents of the syringe to be delivered at a desired rate. Syringe drivers are known in the art and include, for example and without limitation, devices disclosed in U.S. Pat. Nos. 5,064,413; 5,449,345; 5,954,695; 6,428,509; 6,645,177; 7,195,610; 8,231,576; and 8,814,830, the contents of all of which are incorporated herein by reference.

Infusion pumps are well known in the art and include, for example, Baxter Colleague CXE volumetric infusion pump, and Cané Crono pump.

An aspect of the present disclosure relates to a device comprising a therapeutically effective amount of a formulation of the present disclosure. In certain embodiments, the device can be, for example, a syringe, a syringe driver, and an infusion pump comprising the formulation. In certain embodiments, the syringe is a pre-filled syringe.

In some embodiments, the antibody formulation of the disclosure is provided in a fixed volume format. Such formulation can be presented in or as, for example, a vial or ampoule. For example, in some embodiments, the antibody formulation of the disclosure is provided in a volume of about 10 mL to about 20 mL. In some embodiments, the antibody formulation of the disclosure is provided in a volume of about 10 mL to about 15 mL. In some embodiments, the antibody formulation of the disclosure is provided in a volume of about 10 mL to about 12.5 mL. For example, in an embodiment of the formulation comprising 140 mg/mL of antibody, a vial containing 10 mL of such formulation contains 1400 mg of antibody.

Methods of Treatment

The formulations of the present disclosure can be used in a method of treating a disease or condition characterized by the presence or activity of CD38+ cells. Such disease or condition can include, without limitation, a CD38+ hematological malignancy, an autoimmune disease or condition, an inflammatory disease or condition, and LPS- or sepsis-induced kidney injury or dysfunction. The method generally entails administering to a subject in need thereof an effective amount of a formulated antibody provided herein, wherein the administering is by subcutaneous injection or infusion, optionally by large-volume (e.g., 10 mL or more) subcutaneous infusion. In certain embodiments, the subject is a human.

An aspect of the disclosure is a method of treating a CD38+ hematological malignancy in a human subject in need thereof, said method comprising administering to said human subject an effective amount of a formulation comprising at least 100 mg/mL of an anti-CD38 antibody, wherein the anti-CD38 antibody comprises a variable heavy region (VH) comprising three complementarity determining regions (CDRs) CDR-H1, CDR-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises a viscosity reducing agent, a stabilizer, a buffering agent, and a surfactant, and the formulation has a pH of 5.7-7.0 and a viscosity of at most 25 mPa·s at 20° C., and wherein the administering is subcutaneously administering.

In certain embodiments, the viscosity reducing agent is 90-150 mM Arg-Cl.

In certain embodiments, the viscosity reducing agent is 90-130 mM Arg-Cl.

In certain embodiments, the viscosity reducing agent is 110 mM Arg-Cl.

In certain embodiments, the surfactant is Poloxamer 188.

In certain embodiments, the surfactant is 0.4% (w/v) Poloxamer 188.

In certain embodiments, the buffering agent is histidine.

In certain embodiments, the buffering agent is 9 mM histidine.

In certain embodiments, the viscosity reducing agent is 90-150 mM Lys-Ac.

In certain embodiments, the viscosity reducing agent is 125 mM Lys-Ac.

In certain embodiments, the surfactant is Polysorbate 80.

In certain embodiments, the surfactant is 0.04% (w/v) Polysorbate 80.

In certain embodiments, the formulation comprises 125-155 mg/mL of the anti-CD38 antibody.

In certain embodiments, the formulation comprises 140 mg/mL of the anti-CD38 antibody.

In certain embodiments, the stabilizer is sucrose.

In certain embodiments, the stabilizer is 2% (w/v) sucrose.

In certain embodiments, the pH of the formulation is 5.9-7.0.

In certain embodiments, the pH of the formulation is 5.9-6.5

In certain embodiments, the pH of the formulation is 6.2.

In certain embodiments, the pH of the formulation is 6.3.

An aspect of the disclosure is a method of treating a CD38 hematological malignancy in a human subject in need thereof, said method comprising administering to said human subject an effective amount of a formulation comprising 140 mg/mL of an anti-CD38 antibody, wherein the anti-CD38 antibody comprises a variable heavy region (VH) comprising three complementarity determining regions (CDRs) CDR-H1, CDR-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises 9 mM histidine, 110 mM Arg-Cl, 2% (w/v) sucrose, and 0.4% (w/v) Poloxamer 188, and the formulation has a pH of 6.2 and a viscosity of at most 14 mPa·s at 20° C., and wherein the administering is subcutaneously administering.

An aspect of the disclosure is a method of treating a CD38+ hematological malignancy in a human subject in need thereof, said method comprising administering to said human subject an effective amount of a formulation comprising 140 mg/mL of an anti-CD38 antibody, wherein the anti-CD38 antibody comprises a variable heavy region (VH) comprising three complementarity determining regions (CDRs) CDR-H1, CDR-H2, and CDR-H3 comprising the amino acid sequences set forth in SEQ ID NOs: 1-3, respectively, and a variable light region (VL) comprising three CDRs CDR-L1, CDR-L2, and CDR-L3 comprising the amino acid sequences set forth in SEQ ID NOs: 4-6, respectively, the formulation comprises 125 mM Lys-Ac, 2% (w/v) sucrose, and 0.04% (w/v) Polysorbate 80, and the formulation has a pH of 6.2 and a viscosity of at most 14 mPa·s at 20° C., and wherein the administering is subcutaneously administering.

In certain embodiments in accordance with each of the methods above, the subcutaneously administering comprises one or more subcutaneous injections.

In certain embodiments in accordance with each of the methods above, the subcutaneously administering comprises one or more subcutaneous infusions.

In certain embodiments in accordance with each of the methods above, the subcutaneously administering comprises one or more large-volume subcutaneous infusions. As used herein, a "large-volume infusion" refers to an infusion volume of greater than or equal to 5 mL. In certain embodiments, a "large-volume infusion" refers to an infusion volume of about 5-10 mL, about 10-15 mL, about 15-20 mL, about 20-25 mL, or about 25-30 mL. In an embodiment, a "large-volume infusion" refers to an infusion volume of about 5-10 mL. In an embodiment, a "large-volume infusion" refers to an infusion volume of about 10-15 mL. In an embodiment, a "large-volume infusion" refers to an infusion volume of about 15-20 mL. In an embodiment, a "large-volume infusion" refers to an infusion volume of about 20-25 mL. In an embodiment, a "large-volume infusion" refers to an infusion volume of about 25-30 mL.

Surprisingly, it has been found that large-volume infusions of the compositions provided herein are effective for achieving systemic delivery of therapeutically effective amounts of anti-CD38 antibody such as isatuximab, to treat a disease or condition which is characterized by the presence and/or activity of CD38+ cells, including a CD38+ hematological malignancy in a human. Surprisingly, the antibody formulation provided herein demonstrated a bioavailability of at least 89% when administered subcutaneously to minipigs in the absence of dispersing agent such as hyaluronidase. Thus, provided herein is a formulation that does not include biologic dispersing agents. In alternative embodiments, provided herein is a formulation that further includes one or more biologic dispersing agents.

As disclosed in Example 6, following a single intravenous (IV) infusion of isatuximab at 1800 mg/animal over a 30-minute period to minipigs, the mean AUC over the complete 672-hour post dose sampling period ($AUC_{last}$) was 364,000 hr*μg/mL. Following a single subcutaneous (SC) infusion of isatuximab at 1806 mg/animal to minipigs under a flow rate of 0.5, 1 or 2 mL/min, the mean AUC over the complete 672-hour post dose sampling period ($AUC_{last}$) was 326,000, 565,000 and 369,000 hr*μg/mL, respectively. Furthermore, the absolute SC bioavailability of isatuximab in minipigs when given at a dose of 1806 mg/animal (solution of 140 mg/mL) by SC infusion at flow rates of 0.5 to 2 mL/min was at least 89%.

As used herein, "subject" and/or "subject in need thereof" is an individual that has a $CD38^+$ hematological malignancy or is suspected of having a $CD38^+$ hematological malignancy. As used herein, "subject" may also refer to a patient.

The subject according to the disclosure may be a male or a female.

In some embodiments, the subject has been previously treated with one or more agents or therapies suitable for treating a CD38-expressing hematological malignancy. The previous anti-cancer therapy may be, for example, a corticosteroid (e.g., dexamethasone), a chemotherapy drug, a proteasome inhibitor, an immunomodulatory drug, radiotherapy, bone marrow and/or stem cell transplantation, and immunotherapy.

"Chemotherapy drugs" are cytotoxic agents used for example to treat a hematological malignancy include, without limitation, cytarabine (cytosine arabinoside or ara-C) and the anthracycline drugs (such as daunorubicin and/or daunomycin, doxorubicin and liposomal doxorubicin, idarubicin, and mitoxantrone), gemtuzumab, clofarabine, cladribine, hydroxyurea, etoposide, amsacrine, FLT3-inhibitors, and demethylating agents (5-azacytidine and decitabine), melphalan, cyclophosphamide, and vincristine.

proteasome inhibitors include, for example, bortezomib, carfilzomib, and ixazomib. Immunomodulatory drugs include, for example thalidomide, lenalidomide, and pomalidomide.

"Radiation therapy" or "radiation" refers to high-energy radiation used to remove cancer cells. Radiation therapy might be used before a bone marrow or peripheral blood stem cell transplant.

"Bone marrow and/or stem cell transplantation" refers to a cell transplantation aimed to restore stem cells that were destroyed by high doses of chemotherapy drug(s) and/or radiation therapy. Sources of stem cells include bone marrow, peripheral blood or umbilical cord blood. Depending on the source of stem cells that are transplanted, the procedure might be distinguished into bone marrow transplant (BMT) or peripheral blood stem cell transplant (PBSCT) or umbilical cord blood transplantation (UCBT). Furthermore, bone marrow and/or stem cell transplantation might refer to an autologous stem cell transplantation and/or an allogeneic transplantation.

In an "autologous transplant", a subject's own stem cells are removed from his or her bone marrow or peripheral blood, frozen, and stored while the person gets treatment (high-dose of chemotherapy drug(s) and/or radiation). A process called "purging" may be used to try to remove any cancer cells in the samples. The stem cells are then reinfused into the subject's blood after treatment.

"Allogeneic transplants" are transplants from a matched donor. The advantage of allogenic bone marrow transplants is that the transplanted cells from the donor might establish a new immune system, which might detect leukemia cells as foreign and removes them. The disadvantage of the allogeneic transplants is the limitation of matching donors and the side effects.

"Immunotherapy" refers to the stimulation of the subject's immune system to attack the malignant tumor cells that are responsible for the disease. This can be done either through immunization of the subject, e.g., by administering a cancer vaccine, in which case the subject's own immune system is trained to recognize tumor cells as targets to be destroyed, or through the administration of therapeutic antibodies as drugs, in which case the subject's immune system is recruited to destroy tumor cells by the therapeutic antibodies.

In the context of the disclosure, the subject may have been previously treated for a hematological malignancy but relapsed and/or was refractory.

In some embodiments, the subject suffers from multiple my eloma. In some embodiments, the subject has relapsed and/or refractory multiple myeloma "Relapsed" refers to a disease or condition, such as a hematological malignancy, which has been previously treated and which progresses and requires the initiated of additional treatment but does not meet the criteria for either primary refractory or relapsed and refractory disease.

"Refractory" refers to a disease or condition that is non-responsive (failure to achieve minimal response or develops progressive disease while on therapy) while on primary or salvage therapy, or progresses within 60 days of the last therapy.

Relapsed and refractory disease is non-responsive while on salvage therapy (e.g., therapy that is administered after treatment with first line of therapy has failed) or disease that progresses within 60 days of last therapy in patients who have achieved minimal response or better at some point prior to progressing in their current disease course.

Primary refractory disease is disease that is non-responsive in patients who have never achieved minimal response or better with any therapy.

In some embodiments, the subject has been previously treated with bortezomib and/or lenalidomide.

In some embodiments, the subject has previously received an autologous stem cell transplant (ASCT).

In some embodiments, the subject has relapsed within 6 months after an autologous transplantation.

Dosage and Administration

In some embodiments, the formulated antibody provided herein is administered as a "flat dose", such that the amount of antibody administered to a patient is not adjusted based on body size or body weight. In some embodiments, the flat dose administered to the patient comprises 1000-1800 mg of the antibody. In some embodiments, the flat dose is 1000 mg. In some embodiments, the flat dose is 1400 mg.

In some embodiments, the formulated antibody, such as a fixed dose of the antibody, is administered to the patient in a fixed volume. For example, in some embodiments, the antibody formulation of the disclosure is administered in a volume of about 10 to about 20 mL. In some embodiments, the antibody formulation of the disclosure is administered in a volume of about 10 to about 15 mL. In some embodiments, the antibody formulation of the disclosure is administered in a volume of about 10 mL to about 12.5 mL. In some embodiments, the antibody formulation of the disclosure is administered in a volume of about 10 mL to about 11 mL. In some embodiments, the antibody formulation of the disclosure is administered in a volume of about 10 mL to about 10.5 mL.

In some embodiments, the dose of the formulated antibody provided herein is administered subcutaneously over about 10 to about 60 minutes. In some embodiments, the dose of formulated antibody is administered subcutaneously over about 20 to about 40 minutes. In some embodiments, the dose of formulated antibody is administered subcutaneously over about 10 minutes. In some embodiments, the dose of formulated antibody is administered subcutaneously over about 20 minutes. In some embodiments, the dose of formulated antibody is administered subcutaneously over about 30 minutes. In some embodiments, the dose of formulated antibody is administered subcutaneously over about 40 minutes. In some embodiments, the dose of formulated antibody is administered subcutaneously over about 50 minutes. In some embodiments, the dose of formulated antibody is administered subcutaneously over about 60 minutes.

In some embodiments, the subcutaneous administration takes place at a certain rate of infusion of the antibody. For example, the formulation can be administered subcutaneously at a rate suitable to achieve complete delivery of a desired dose, in a minimal time, without significant leakage or significant discomfort. Such rate may range, for example, from about 0.1 mL/min to about 1.5 mL/min. In some embodiments, about the rate of infusion is 0.8 mL/min. In some embodiments, the rate is 1 mL/min. In some embodiments, the rate is 1.2 mL/min. In some embodiments, the rate is 1.5 mL/min.

In some embodiments, the initial rate of infusion may be maintained for the entire period of infusion. In other embodiments, the rate of infusion may be adjusted up or down, or both up and down, during the period of infusion.

In some embodiments, the anti-CD38 antibody is administered alone. In other embodiments, the anti-CD38 antibody is administered together with another agent suitable for treating the CD38$^+$ hematological cancer. In some embodiments, the other agent is a corticosteroid (e.g., dexamethasone), a chemotherapy drug, a proteasome inhibitor, an immunomodulatory drug, or a combination thereof.

When administered with another agent suitable for treating the CD38$^+$ hematological cancer, the anti-CD38 antibody and the other agent(s) can be administered either simultaneously or separately (e.g. sequentially over a period of time). The anti-CD38 antibody and the other agent(s) can be administered by the same or different routes of administration. When the anti-CD38 antibody and the other agent(s) are administered by the same route of administration, they can be administered by the same or different sites of administration.

Corticosteroids such as dexamethasone are used to treat a variety of inflammatory, autoimmune, and allergic conditions. It also is used in the treatment of cancer, either as a direct agent (e.g., in multiple myeloma) or in combination with other agents (e.g., immunomodulatory drugs, chemotherapy drugs, and proteasome inhibitors). Corticosteroids such as dexamethasone can also be used to counteract side effects of chemotherapy drug(s) (e.g., nausea and inflammation). Corticosteroids such as dexamethasone can also be used as a premedication to reduce potential risk and/or severity of infusion reactions (IR) due to infusion of the antibody. Dexamethasone is typically administered orally.

Pomalidomide is a thalidomide analogue and immunomodulatory drug with multiple cellular effects that inhibit multiple myeloma cell growth and survival blocking the stromal support from the bone marrow microenvironment that can promote myeloma cell growth; in addition, pomalidomide has potent immunomodulatory effects that enhance the immune response to myeloma cells by stimulating natural killer (NK) cells and by inhibiting regulatory T cells. Pomalidomide is typically administered orally.

In the context of the disclosure, a physician may evaluate the disease response and thus adapt the administration regimen.

In other embodiments, the anti-CD38 antibody is administered together with one or more biologic dispersing agents. When administered with a biologic dispersing agent, the anti-CD38 antibody and the other agent(s) can be administered either simultaneously or separately (e.g. sequentially over a period of time). The anti-CD38 antibody and the other agent(s) can be administered by the same or different routes of administration. When the anti-CD38 antibody and the other agent(s) are administered by the same route of administration, they can be administered by the same or different sites of administration.

Prior to the administration of the antibody the subject receives premedication to reduce the risk and/or severity of Infusion Reactions (IRs) typically observed with the administration of a monoclonal antibody. Premedications can include, for example, Montelukast, Acetaminophen, Ranitidine, Diphenyldramamine, dexamethasone, or combinations thereof. In some embodiments, where the subject does not experience an IR after four consecutive administrations of the antibody as described herein, the premedication may be discontinued.

"Disease response" may be determined according to standard criteria for hematological malignancies and staging. Methods to evaluate the disease response of a hematological malignancy, in particular a CD38$^+$ hematological malignancy, are known to persons skilled in the art. For example, methods to evaluate the disease response include performance status evaluations such as Eastern Cooperative Oncology Group (ECOG) performance status and International Myeloma Working Group Response Criteria (see Oken, et al., *Am. J. Clin. Oncol.* 1982; 5(6):649-655 and Kumar, et al., *Lancet Oncol.* 2016; 17(8):328-346, respectively) Methods to evaluate disease response can also include quantification of disease markers, bone marrow biopsy and/or aspiration, radiologic imaging of plasmacytoma, bone skeletal survey, M-protein quantification (serum and/or 24-hr urine) and serum free light chain levels or urinary light chain levels, serum β2-microglobulin, lymph node biopsy, radiologic tumor assessment (by X-ray, computed tomography (CT) scan, PET scan, or magnetic resonance imaging (MRI)), and blood count including blast count. This list of evaluation methods is to be understood as being non-limiting.

Based on the results obtained from the evaluation of the disease response, the disease response may then be stratified according to the standard criteria for underlying disease and classified into complete response or complete remission (CR), partial response (PR), stable disease (SD), or progressive disease (PD).

"Markers" used in the context of the response evaluation may include serum and/or plasma markers, such as C-reactive protein (CRP), tumor necrosis factor alpha (TNF-α), IL-6, IL-1β, or IFN. Markers can also include cell surface markers, such as CD38.

Techniques to evaluate the disease response in a subject that has multiple myeloma include, for example, bone marrow biopsy and/or aspiration, radiologic imaging of plasmacytoma, bone skeleton survey, M-protein quantification, and measure of serum β2-microglobulin.

The disease response evaluation may further include receptor density and receptor occupancy on circulating tumor cells (peripheral blood), receptor density and receptor occupancy on blasts and plasma cells in bone marrow, and level of human anti-drug antibodies (ADA).

The entire contents of all patents and published patent applications cited in this disclosure are incorporated herein by reference.

The present disclosure will be further understood by reference to the following non-limiting examples. The examples have been set forth below for the purpose of illustration and to describe certain embodiments of the disclosure. The scope of the claims is not to be in any way limited by the examples set forth herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g. amounts, temperature, etc.)

Example 1—Initial Screening

Initial formulation development activities involved screening of buffer-pH systems, thermal stabilizers, surfactant as well as viscosity reducer to identify excipients and their combination that are compatible with isatuximab and enhance its stability, while maintaining osmolality and viscosity suitable for subcutaneous injection.

Selection of the Buffer and pH System

To identify the buffer and pH system, the stability of isatuximab was evaluated in 16 different buffer-pH systems. The buffer-pH systems (Table 1) were tested based on their buffering capacity in the pH range of interest.

TABLE 1

| Buffer-pH system tested | | |
| --- | --- | --- |
| Buffer | pH | pKa |
| Citrate 10 mM | 5.0 | 4.8-6.4 |
| Citrate 10 mM | 5.5 | |
| Citrate 10 mM | 6.0 | |
| Citrate 10 mM | 6.5 | |
| Citrate 10 mM | 7.0 | |
| Histidine 10 mM | 5.5 | 6.0 |
| Histidine 10 mM | 6.0 | |
| Histidine 10 mM | 6.5 | |
| Phosphate 10 mM | 6.5 | 7.2 |
| Phosphate 10 mM | 7.0 | |
| Phosphate 10 mM | 7.4 | |
| Succinate 10 mM | 5.0 | 4.2-5.6 |
| Succinate 10 mM | 5.5 | |
| Succinate 10 mM | 6.0 | |
| Acetate 10 mM | 5.0 | 4.8 |
| Acetate 10 mM | 5.5 | |

The buffer-pH systems were evaluated with regard to their impact on aggregation of isatuximab, in terms of formation of visible and sub-visible particles and soluble aggregates (high-molecular weight species HMWs) upon shaking and thermal stress in liquid formulation of isatuximab at a concentration of 5 mg/mL.

As shown in Table 2, aggregation of isatuximab into visible particles was found to be dependent on the pH and buffer system. The histidine buffer system with pH ranging from 5.5 to 6.5 showed the highest stability under shaking stress (presenting fewer visible particles after stress), and the citrate buffer system within pH 5.0 to 7.0 and citrate buffer at pH 5.5, 6.5 and 7.0 showed the highest stability upon thermal stress (presenting fewer visible particles after two weeks of stress). Interestingly, the phosphate buffer system at pHs ranging from 6.5-7.4 showed the highest thermal stability after one week of thermal stress, but had several visible particles after two weeks of thermal stress and showed the lowest stability for isatuximab under shaking stress of all the buffer systems tested.

TABLE 2

| Visual inspection | | | | | |
| --- | --- | --- | --- | --- | --- |
| Buffer | pH | T0 | Shaking | 1 week 40° C. | 2 weeks 40° C. |
| Citrate 10 mM | 5.0 | 0 | ++ | 0 | + |
| Citrate 10 mM | 5.5 | 0 | ++ | 0 | 0 |
| Citrate 10 mM | 6.0 | 0 | ++ | + | + |
| Citrate 10 mM | 6.5 | 0 | ++ | 0 | 0 |
| Citrate 10 mM | 7.0 | 0 | ++ | 0 | 0 |
| Histidine 10 mM | 5.5 | 0 | + | + | ++ |
| Histidine 10 mM | 6.0 | 0 | + | + | ++ |
| Histidine 10 mM | 6.5 | 0 | + | 0 | ++ |
| Phosphate 10 mM | 6.5 | 0 | +++ | 0 | ++ |
| Phosphate 10 mM | 7.0 | 0 | +++ | 0 | ++ |
| Phosphate 10 mM | 7.4 | 0 | +++ | + | ++ |
| Succinate 10 mM | 5.0 | 0 | ++ | ++ | ++ |
| Succinate 10 mM | 5.5 | 0 | ++ | ++ | ++ |
| Succinate 10 mM | 6.0 | 0 | + | ++ | ++ |
| Acetate 10 mM | 5.0 | 0 | ++ | + | + |
| Acetate 10 mM | 5.5 | 0 | ++ | ++ | ++ |

0: no visible particles
+: few visible particles
++: several visible particles
+++: numerous visible particles The number of sub-visible particles $\geq 10$ μm and $\geq 25$ μm after shaking stress and thermal stress were measured by light obscuration (LO). As shown in FIG. 1, under shaking and thermal stress, phosphate buffers presented the highest levels of sub-visible particles. Histidine and acetate buffer systems provided the lowest levels of sub-visible particles, indicating higher stability of isatuximab.

Figure 2:
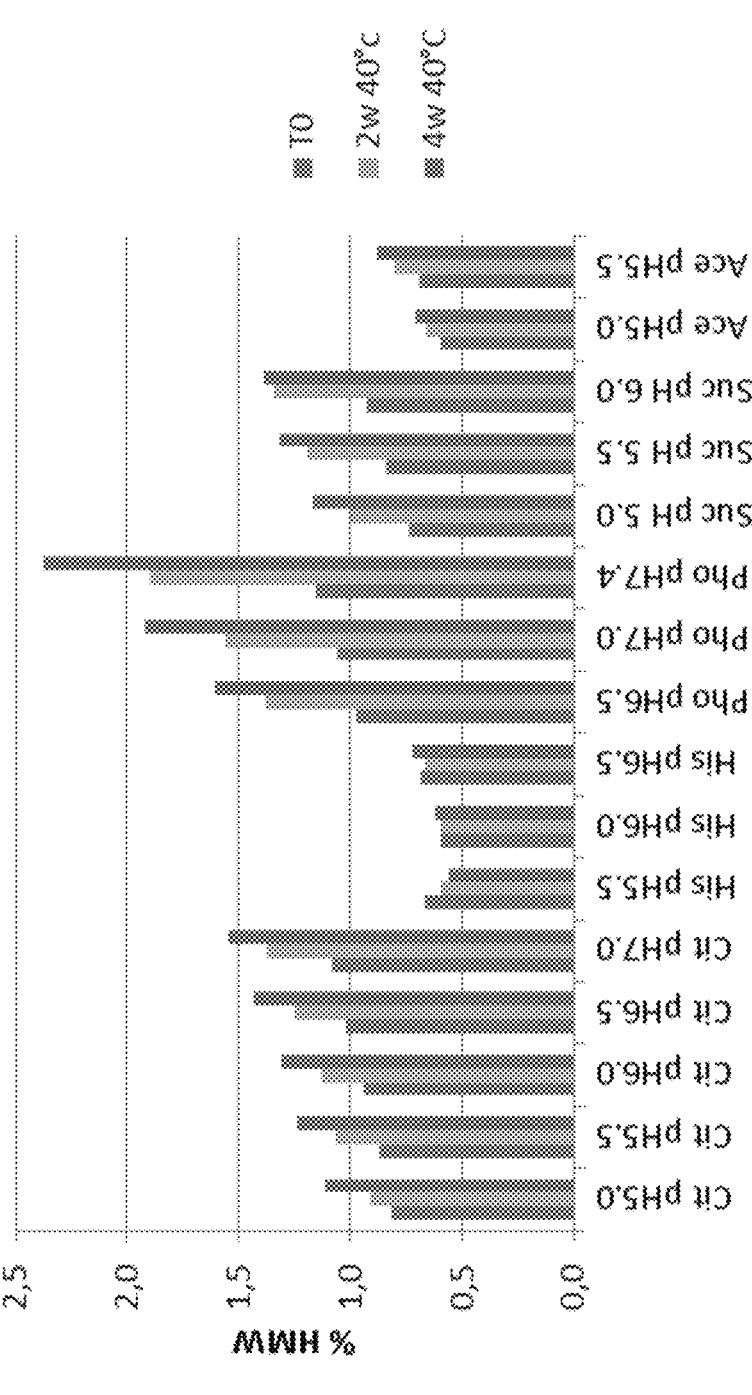
FIG. 2 is a graph depicting the percentage of soluble aggregates (high molecular weight aggregates (HMWs) as measured using size exclusion chromatography (SE-HPLC)) upon thermal stress at 40° C. 2 w 40° C., two weeks at 40° C.; 4 w 40° C., 4 weeks at 40° C.; Cit, citrate buffer; His, histidine buffer; Pho, phosphate buffer; Ace, acetate buffer.

Soluble aggregates (HMWs) were observed by size exclusion chromatography (SE-HPLC) after thermal stress in citrate, histidine, phosphate, succinate, and acetate buffers at various pH. As shown in FIG. 2, citrate, phosphate, and succinate buffer systems showed higher increase of soluble aggregates and a general trend was observed showing the higher pH, the higher the soluble aggregates (HMWs) content. This was particularly significant at pH above 7.0. Shaking stress did not appear to have any impact on soluble aggregates.

The impact of pH on isatuximab stability was further studied in histidine buffer in the presence of sucrose and polysorbate 80. Isatuximab at a concentration of 5 mg/mL in the formulations shown in Table 3 were incubated at 40° C. for 1 month and HMWs were measured by SE-HPLC.

TABLE 3

| | | | Composition | |
| Prototype reference | Buffer | pH | Sucrose % (w/v) | PS80 % (w/v) |
|---|---|---|---|---|
| His 10 mM pH 6.5 | Histidine 10 mM | 6.5 | 10 | 0.02 |
| His 10 mM pH 6.0 | Histidine 10 mM | 6.0 | 10 | 0.02 |
| His 20 mM pH 6.5 | Histidine 20 mM | 6.5 | 10 | 0.02 |
| His 20 mM pH 6.0 | Histidine 20 mM | 6.0 | 10 | 0.02 |

Buffer-pH system tested

Figure 3:
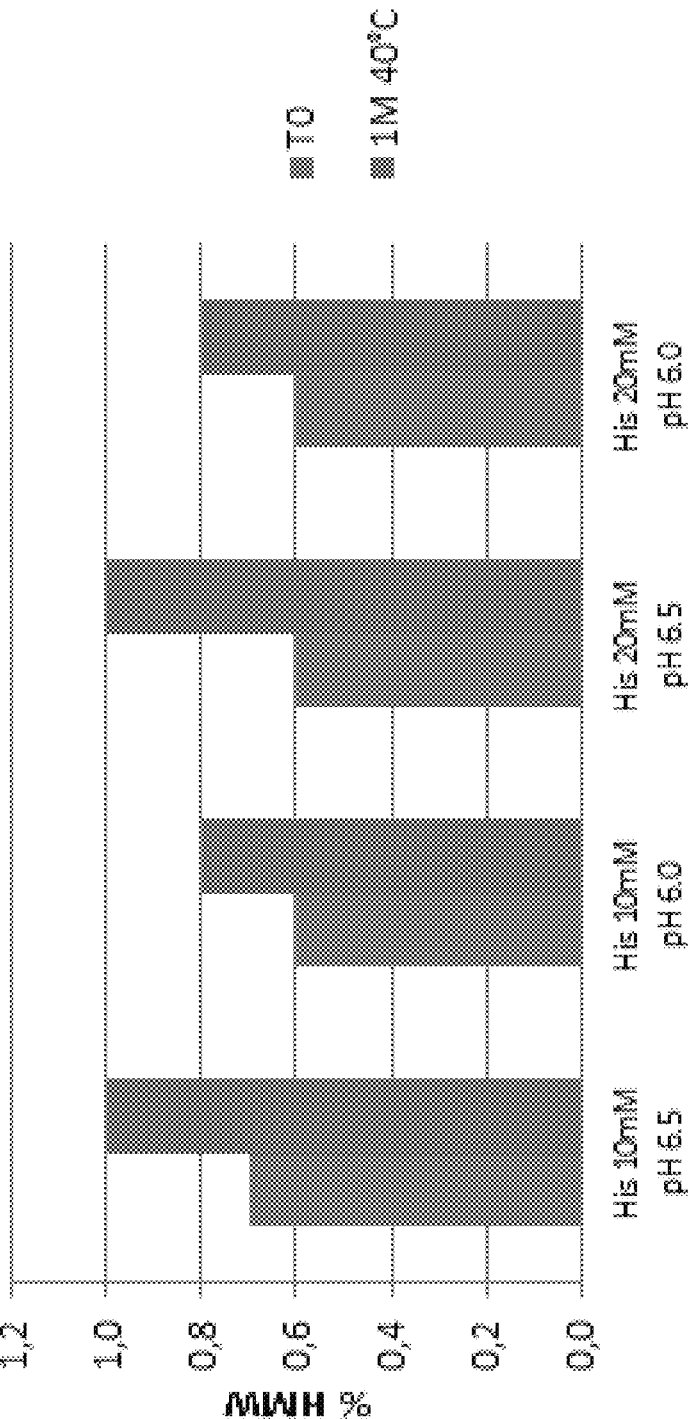
FIG. 3 is a graph depicting the percentage of soluble aggregates (high molecular weight aggregates (HMWs)) as measured using size exclusion chromatography (SE-HPLC) upon thermal stress at 40° C. in histidine buffers with indicated values of pH and concentration. 1M 40° C., one month at 40° C.

HMWs were observed by SE-HPLC. As shown in FIG. 3, there were fewer soluble aggregates (HMWs) after 1 month of thermal stress at 40° C. in histidine buffers at pH 6.0 compared to pH 6.5.

Figure 4:
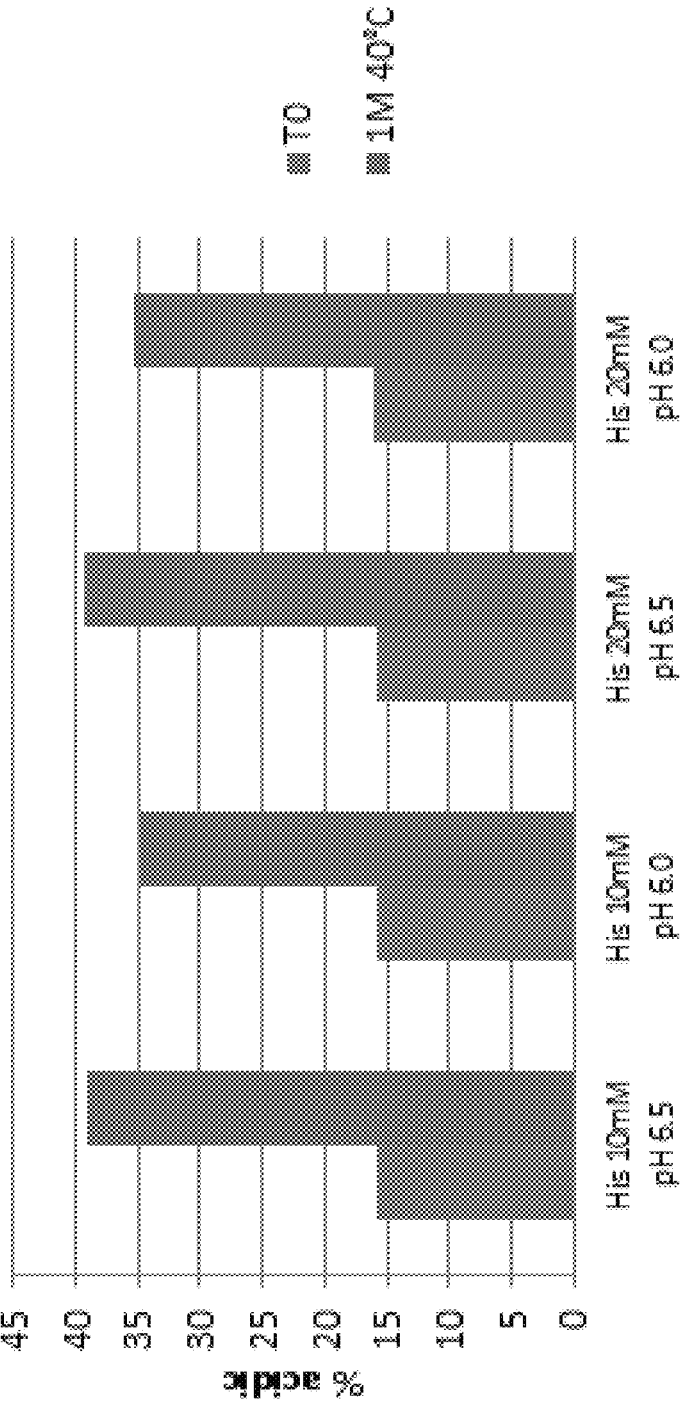
FIG. 4 is a graph depicting the percentage acidic forms of isatuximab as measured using weak cationic exchange analysis upon shaking stress at 40° C. in histidine buffers with indicated values of pH and concentration. 1M 40° C., one month at 40° C.

The level of acidic isoforms of isatuximab was measured by WCX (week cationic exchange) after incubation of 5 mg/mL isatuximab in the formulations shown in Table 3 for 1 month at 40° C. As shown in FIG. 4, histidine formulations at pH 6.0 showed a smaller increase in the level of acidic forms of isatuximab compared to pH 6.5 after 1 month at 40° C.

These results showed that the pH and buffer system impacted the stability of isatuximab, and pH around pH 6.0 was more stable than pH 6.5.

Selection of Viscosity Reducing Excipient

To enable subcutaneous delivery of isatuximab, various formulation conditions with viscosity reducing excipients were tested to determine whether high concentration with a viscosity less than 25 cP at 20° C. could be developed.

The antibody was concentrated and formulated in the test formulations. Protein concentration of the resulting formulations was confirmed spectroscopically with a SoloVPE instrument, and the pH of the final solution was measured.

TABLE 4

Formulations tested in viscosity study

| Buffer | pH | Sucrose % w/v | Arg-Cl mM | Other | Conc. mg/ml | Visco. mP · s (cP) |
|---|---|---|---|---|---|---|
| 10 mM Histidine | 5.73 | 0 | 200 | — | 150 | 21.5 |
| 10 mM Histidine | 5.75 | 0 | 200 | — | 150 | 19.5 |
| 10 mM Histidine | 5.44 | 0 | 150 | — | 150 | 39.0 |
| 10 mM Histidine | 5.46 | 0 | 200 | — | 150 | 31.2 |
| 10 mM Histidine | 5.11 | 2 | 150 | — | 155 | 102.0 |
| 10 mM Histidine | 5.10 | 2 | 200 | — | 151 | 60.8 |
| 10 mM Histidine | 5.31 | 2 | 150 | — | 154 | 57.0 |
| 10 mM Histidine | 5.34 | 2 | 200 | — | 155 | 37.3 |
| 10 mM Histidine | 5.82 | 2 | 200 | — | 152 | 21.0 |
| 10 mM Histidine | 5.62 | 2 | 150 | — | 151 | 19.0 |
| 10 mM Histidine | 5.21 | 2 | 150 | — | 152 | 94.0 |
| 10 mM Histidine | 5.05 | 2 | 200 | — | 152 | 68.0 |
| 10 mM Histidine | 5.39 | 2 | 150 | — | 155 | 38.0 |
| 10 mM Histidine | 5.37 | 2 | 200 | — | 152 | 45.0 |
| 10 mM Histidine | 6.17 | 2 | 100 | — | 153 | 19.0 |

TABLE 4-continued

Formulations tested in viscosity study

| Buffer | pH | Sucrose % w/v | Arg-Cl mM | Other | Conc. mg/ml | Visco. mP · s (cP) |
|---|---|---|---|---|---|---|
| 10 mM Histidine | 6.13 | 2 | 150 | — | 147 | 13.4 |
| 10 mM Histidine | 6.35 | 2 | 200 | — | 154 | 11.7 |
| 10 mM Histidine | 6.85 | 2 | 100 | — | 150 | 11.0 |
| 10 mM Histidine | 6.93 | 2 | 150 | — | 148 | 9.6 |
| 10 mM Histidine | 6.99 | 2 | 200 | — | 152 | 9.7 |
| 10 mM Histidine acetate | 6.20 | 2 | 100* | — | 153 | 23.7 |
| 10 mM Histidine acetate | 6.16 | 2 | 150* | — | 154 | 20.0 |
| 10 mM Histidine acetate | 6.17 | 2 | 200* | — | 153 | 18.0 |
| 10 mM Histidine | 6.30 | 0 | 0 | — | 150 | 59.0 |
| 10 mM Histidine | 6.31 | 2 | 0 | — | 150 | 60.0 |
| 10 mM Histidine | 6.35 | 2 | 50 | — | 150 | 23.6 |
| 10 mM Histidine | 6.36 | 2 | 100 | — | 150 | 16.1 |
| 10 mM Histidine | 6.34 | 2 | 150 | — | 150 | 14.5 |
| 10 mM Histidine | 6.35 | 2 | 200 | — | 150 | 12.4 |
| 10 mM Histidine | 6.25 | 0 | 0 | — | 180 | 242.0 |
| 10 mM Histidine | 6.38 | 2 | 0 | — | 180 | 121.0 |
| 10 mM Histidine | 6.34 | 2 | 50 | — | 180 | 60.0 |
| 10 mM Histidine | 6.35 | 2 | 100 | — | 180 | 32.5 |
| 10 mM Histidine | 6.37 | 2 | 150 | — | 180 | 32.5 |
| 10 mM Histidine | 6.36 | 2 | 200 | — | 180 | 25.5 |
| 10 mM Histidine | 6.36 | 2 | 0 | 150 mM Lysine | 150 | 10.8 |
| 10 mM Histidine | 4.7 | 2 | 0 | 150 mM Proline | 150 | 369 |
| 10 mM Succinate | 5.77 | 2 | 150 | — | 150 | 21.7 |
| 10 mM Succinate | 5.85 | 2 | 150 | — | 150 | 18.7 |
| 10 mM Phosphate-Succinate | 5.42 | 2 | 150 | — | 150 | 32.8 |
| 10 mM Phosphate-Tris | 4.98 | 2 | 150 | — | 150 | 128 |
| Water | 5.97 | 2 | 150 | — | 150 | 17 |
| 10 mM Histidine | 4.96 | 2 | 0 | 200 mM Proline | 150 | 357 |
| 10 mM Histidine | 6.03 | 0 | 0 | 150 mM NaCl | 150 | 27.2 |
| 10 mM Histidine | 7.07 | 0 | 0 | — | | 21 |

*Formulation used Arginine-acetate rather than Arginine-Cl

Viscosity of all samples were measured on a RheoSense Initium instrument using its automatic method at 20° C. This automatically determines a shear rate appropriate so that the instrument operated in a desirable range of pressure for the sensors. Because the shear rate did not exceed 10,000 s$^{-1}$, non-Newtonian effects such as shear thinning is considered negligible.

Figure 5:
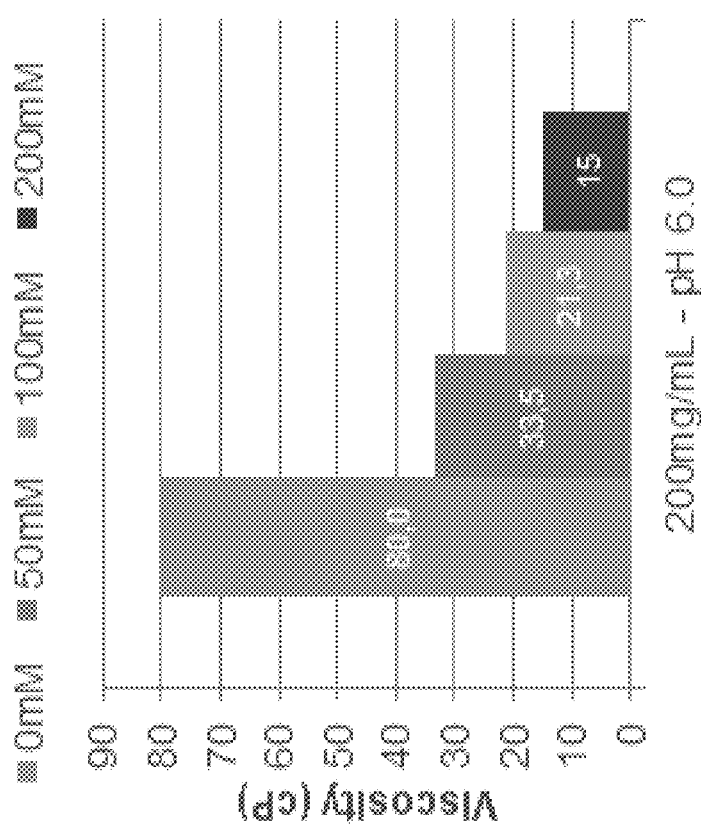
FIG. 5 is a graph depicting viscosity of 200 mg/mL isatuximab in Arginine-Cl pH 6.0 at the indicated concentrations.

FIG. 5 shows the viscosity (cP) of a solution of 200 mg/mL isatuximab at pH 6.0 in the presence of 0, 50, 100, and 200 mM L-Arginine-Cl. The preliminary measurements indicated that Arginine-Cl was an effective viscosity reducing excipient in a concentration-dependent manner; increasing Arginine-Cl concentration correlated with decreasing viscosity.

Over 40 different formulations with varying pH, viscosity reducing agent for various concentrations of isatuximab were tested. The results are shown in Table 4.

Figure 6A:
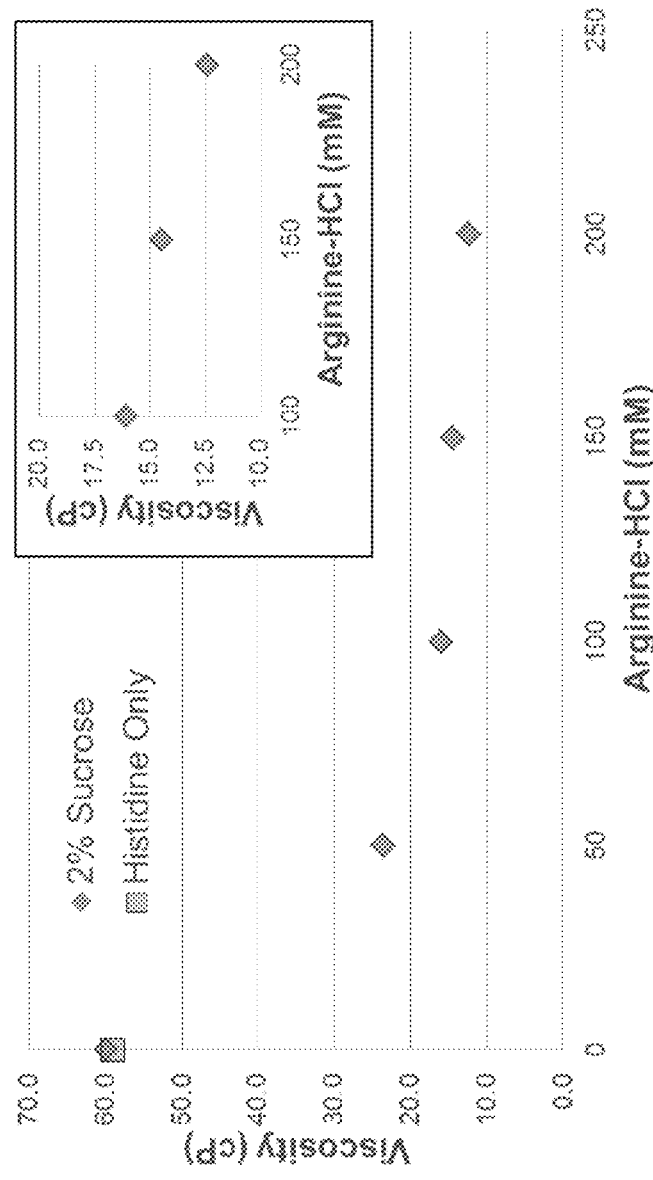
FIG. 6A is a graph depicting viscosity of 150 mg/mL isatuximab over a range of concentrations of Arginine-HCl buffer, pH 6.3. Inset shows detail at higher concentrations of Arginine-HCl.
Figure 6B:
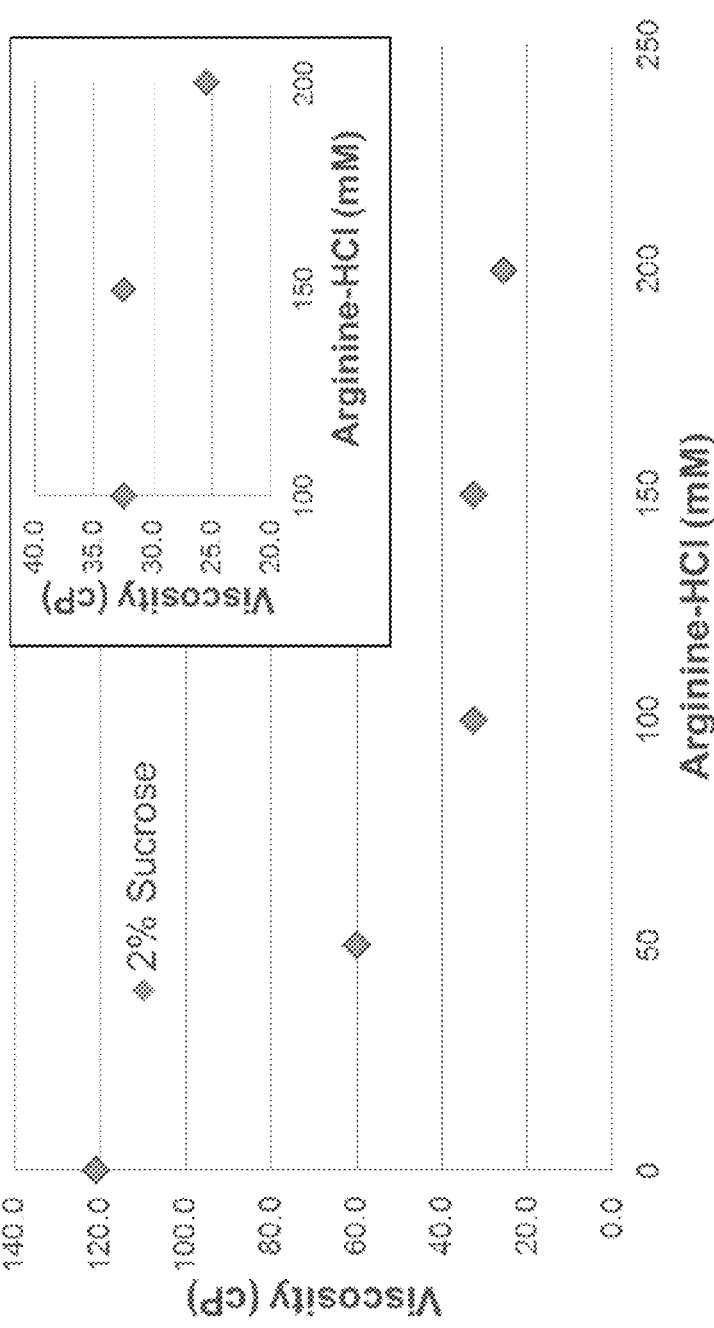
FIG. 6B is a graph depicting viscosity of 180 mg/mL isatuximab over a range of concentrations of Arginine-HCl buffer, pH 6.3. Inset shows detail at higher concentrations of Arginine-HCl.

The effect of the concentration of Arginine-Cl on the viscosity is shown in FIGS. 6A and 6B for two concentrations of isatuximab, 150 mg/mL (FIG. 6A) and at 180 mg/mL (FIG. 6B) in the presence of 10 mM histidine and 2% sucrose.

Figure 7A:
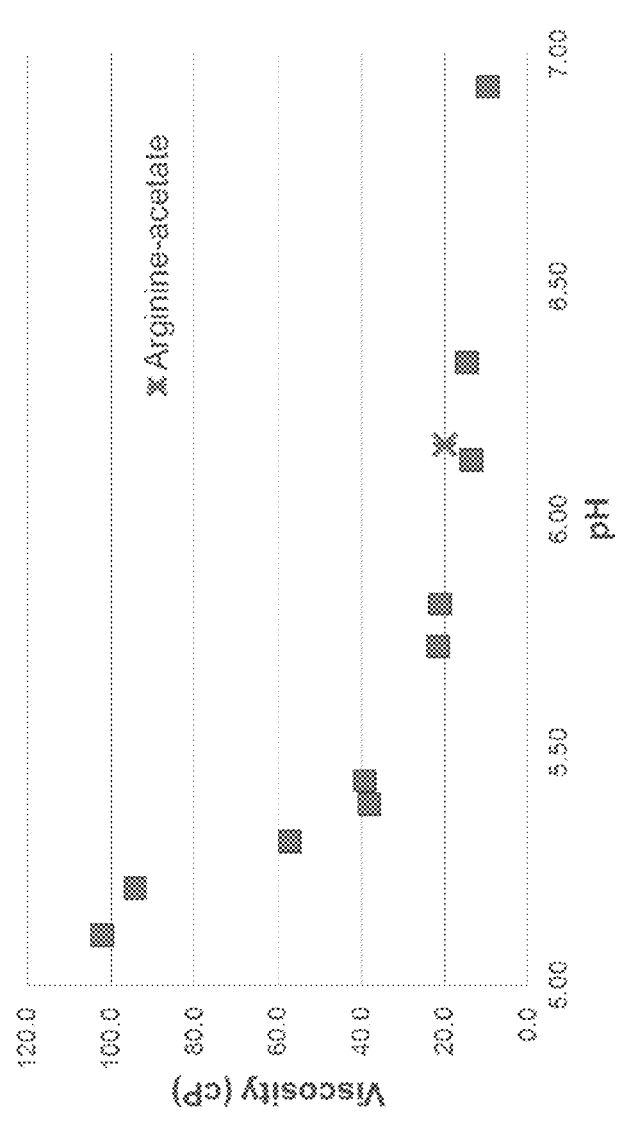
FIG. 7A is a graph depicting viscosity of 150 mg/mL isatuximab over a range of pH in 150 mM Arginine-HCl buffer.
Figure 7B:
FIG. 7B is a graph depicting viscosity of 150 mg/mL isatuximab over a range of pH in 200 mM Arginine-HCl buffer.

In addition to concentration of Arginine-Cl, pronounced effect of pH on the viscosity of isatuximab was observed. FIGS. 7A and 7B show viscosity as a function of the pH for 150 mM Arginine-Cl (FIG. 7A) and 200 mM Arginine-Cl (FIG. 7B).

Figure 8:
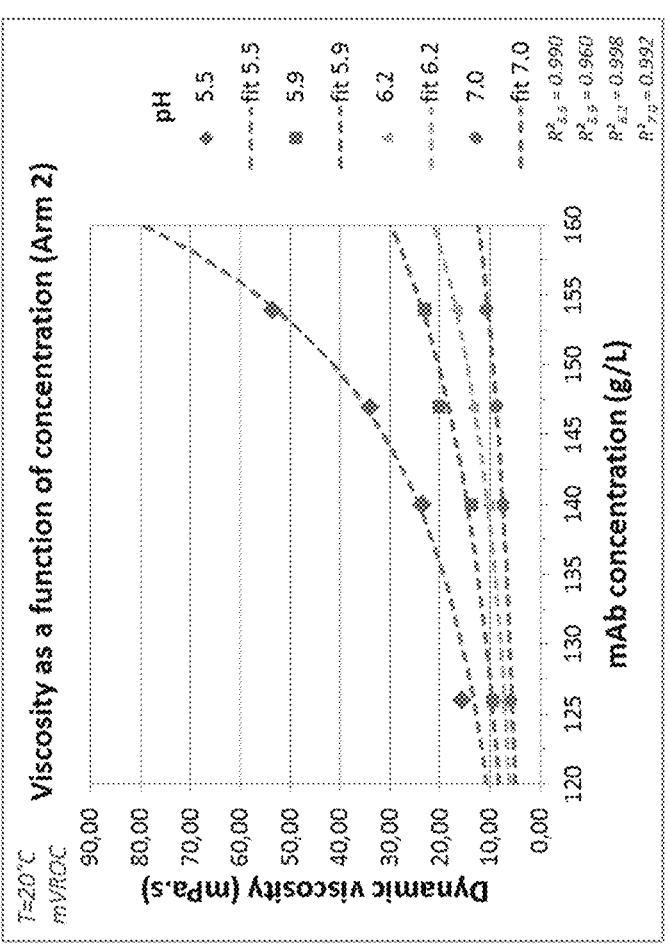
FIG. 8 is a graph depicting viscosity plotted as a function of mAb concentration, at pH 5.5, 5.9, 6.2 and 7.0 (T=20° C.). Fit: Mooney-based equation.

Surprisingly, the results shown in FIGS. 7A and 7B shown an inverse relationship between viscosity and pH, namely, increasing viscosity was associated with decreasing pH. There was a sharp increase in viscosity at pH≤5.7. This inverse relationship is the opposite of what is typically expected and observed for protein solutions. In addition, this unexpected effect was further amplified with increasing antibody concentration (FIG. 8).

Arginine-Cl concentration of at least 100 mM was shown to reduce the viscosity of 150 mg/mL isatuximab to less than 20 cP and to reduce the viscosity of 180 mg/mL isatuximab to less than 40 cP. In addition, pH was shown to have a significant effect on the viscosity, as demonstrated by a sharp increase of the viscosity for pH below 5.7. At the same time, account must be taken of the impact of pH on the stability of isatuximab. As demonstrated in FIGS. 3 and 4, histidine buffer systems at a pH value close to 6.0 resulted in less HMWs after 1 month of thermal stress compared to buffer systems at pH 6.5.

Example 2—Viscosity Studies

With results of the studies described in Example 1 in hand, and with the goal of arriving at formulations containing high concentration (e.g., at least 100 mg/mL) of isatuximab potentially suitable for subcutaneous administration, a number of formulations were prepared and studied in more detail. Different parameters may influence the viscosity of a protein in solution, such as protein concentration, pH, concentration of viscosity reducer, and temperature. Several experiments were performed to evaluate the impact of protein concentration, pH, arginine concentration on formulation viscosity. Table 5 shows the parameters and value ranges tested. The effect of temperature was also examined, considering that the drug product will be stored in refrigerated conditions (5±3° C.).

TABLE 5

| | Viscosity study | |
| --- | --- | --- |
| Parameter | Target formulation value | Range probed |
| Protein concentration | 140 mg/mL | 126-154 mg/mL |
| pH | 6.2 | 5.5-7.0 |
| Arginine concentration* | 110 mM | 90-150 mM |

*probed at fixed pH 6.2 and mAb concentration 140 mg/mL

The target concentration was set at 140 mg/mL to achieve a viscosity below 25 cPs at 20° C. including when the mAb solutions exhibit fluctuations in antibody concentration or viscosity reducing agent concentration or in pH, inherent in the process of manufacturing. Indeed, such variation between actual and target compositions of each excipients are commonly observed with UF/DF due to Donnan effect or during compounding steps because of accuracy in weighing of the excipients or other manufacturing steps (e.g. filtration) that may impact the excipient levels in the final drug product.

Solutions of mAb at high concentrations tend to exhibit high viscosity. Arginine was chosen as a viscosity reducer in order to determine whether a high concentration liquid formulation of isatuximab having a viscosity lower than 25 mPa·s at 20° C. could be developed.

This study was conducted in three arms. The first arm examined coarse pH and concentration. The second arm examined fine pH and concentration. The third arm examined arginine concentration.

In the first arm of the study, the effects of isatuximab concentration, pH, and temperature on viscosity were studied. Seven formulations were prepared for this arm of the study. Detailed compositions, with measured values, are presented in Table 6.

TABLE 6

| Formulations with measured values for isatuximab concentration ($C_{mab}$) and pH in formulations | | | | | |
| --- | --- | --- | --- | --- | --- |
| mAb (mg/mL) | Arginine-Cl (mM) | pH | Histidine (mM) | Sucrose % (w/v) | P188 % (w/v) |
| 126 | 113 | 6.2 | 9 | 2 | 0.4 |
| 142 | 112 | 5.9 | 9 | 2 | 0.4 |
| 143 | 112 | 6.2 | 9 | 2 | 0.4 |
| 142 | 112 | 6.5 | 9 | 2 | 0.4 |
| 141 | 112 | 6.8 | 9 | 2 | 0.4 |
| 152 | 111 | 5.9 | 9 | 2 | 0.4 |
| 154 | 111 | 6.2 | 9 | 2 | 0.4 |

The concentration of P188 at 0.4% w/v showed positive stability effect compared to the formulation with no surfactant. Sucrose at a concentration of 2% allowed a sufficient stability while maintaining the osmolality close to isotonicity.

In the second arm of the study, the effects of isatuximab concentration and pH on viscosity at 20° C. were studied. A total of 32 formulations were prepared. Solutions were prepared at 4 target concentrations of antibody (126, 140, 147, and 154 g/L) and 8 target pH values (5.5, 5.7, 5.9, 6.2, 6.5, 6.7, 6.9, 7.0). Detailed compositions, with measured values, are presented in Table 7.

TABLE 7

| Formulations with measured values for isatuximab concentration ($C_{mab}$) and pH in formulation | | | | | |
| --- | --- | --- | --- | --- | --- |
| mAb (mg/mL) | Arginine-Cl (mM) | pH | Histidine (mM) | Sucrose % (w/v) | P188 % (w/v) |
| 124.6 | 112 | 5.5 | 9 | 2 | 0.4 |
| 131 | 111 | 5.7 | 9 | 2 | 0.4 |
| 129.4 | 111 | 5.9 | 9 | 2 | 0.4 |
| 127.3 | 111 | 6.2 | 9 | 2 | 0.4 |
| 125.1 | 112 | 6.6 | 9 | 2 | 0.4 |
| 126.5 | 111 | 6.7 | 9 | 2 | 0.4 |
| 124.4 | 112 | 6.9 | 9 | 2 | 0.4 |
| 125.6 | 112 | 7.0 | 9 | 2 | 0.4 |

TABLE 7-continued

Formulations with measured values for isatuximab concentration ($C_{mab}$) and pH in formulation

| mAb (mg/mL) | Arginine-Cl (mM) | pH | Histidine (mM) | Sucrose % (w/v) | P188 % (w/v) |
|---|---|---|---|---|---|
| 141.4 | 110 | 5.5 | 9 | 2 | 0.4 |
| 139.5 | 110 | 5.7 | 9 | 2 | 0.4 |
| 141.7 | 110 | 5.9 | 9 | 2 | 0.4 |
| 140.5 | 110 | 6.2 | 9 | 2 | 0.4 |
| 140.3 | 110 | 6.5 | 9 | 2 | 0.4 |
| 140.1 | 110 | 6.7 | 9 | 2 | 0.4 |
| 138.7 | 110 | 6.9 | 9 | 2 | 0.4 |
| 137.4 | 110 | 7.0 | 9 | 2 | 0.4 |
| 147.5 | 109 | 5.6 | 9 | 2 | 0.4 |
| 150 | 109 | 5.7 | 9 | 2 | 0.4 |
| 148.6 | 109 | 5.9 | 9 | 2 | 0.4 |
| 147.8 | 109 | 6.2 | 9 | 2 | 0.4 |
| 147.2 | 109 | 6.5 | 9 | 2 | 0.4 |
| 148.6 | 109 | 6.7 | 9 | 2 | 0.4 |
| 148.2 | 109 | 6.9 | 9 | 2 | 0.4 |
| 144.4 | 110 | 7.0 | 9 | 2 | 0.4 |
| 157.6 | 108 | 5.5 | 9 | 2 | 0.4 |
| 156.3 | 108 | 5.7 | 9 | 2 | 0.4 |
| 155.8 | 108 | 5.9 | 9 | 2 | 0.4 |
| 157.4 | 108 | 6.2 | 9 | 2 | 0.4 |
| 156.1 | 108 | 6.5 | 9 | 2 | 0.4 |
| 155.8 | 108 | 6.7 | 9 | 2 | 0.4 |
| 157.5 | 108 | 6.9 | 9 | 2 | 0.4 |
| 159.5 | 108 | 7.1 | 9 | 2 | 0.4 |

In the third arm of the study, the arginine concentration was varied between 90 and 150 mM. The detailed composition of 5 formulations, with measured values when available, are presented in Table 8.

TABLE 8

Formulations for reference solutions (before spiking) in study Arm 3-study of impact of arginine concentration on stability and viscosity

| mAb (mg/mL) | Arginine-Cl (mM) | pH | Histidine (mM) | Sucrose % (w/v) | P188 % (w/v) |
|---|---|---|---|---|---|
| 140 | 93 | 6.2 | 9 | 2 | 0.4 |
| 141 | 101 | 6.2 | 9 | 2 | 0.4 |
| 141 | 117 | 6.2 | 9 | 2 | 0.4 |
| 140 | 127 | 6.2 | 9 | 2 | 0.4 |
| 144 | 150 | 6.2 | 9 | 2 | 0.4 |

For Arm 1 of the study, the viscosity of all samples was determined on a Rheosense m-VROC viscometer at 5, 10, 15, 20, 25 and 30° C. For each sample and each temperature, the flowrates were chosen at 50% of the maximum flowrate, leading to shear rates between 250 and 2500 $s^{-1}$. Newtonian behavior was assumed for all samples.

For Arm 2 of the study, the viscosity of all samples was determined on a Rheosense m-VROC viscometer at 20° C. For each sample, the flowrate was chosen at 50% of the maximum flowrate determined by the instrument during the priming phase. This led to shear rates between 250 and 2500 $s^{-1}$. Newtonian behavior was assumed for all samples.

For Arm 3 of the study, the viscosity of all samples was determined on a Rheosense m-VROC viscometer at 20° C. For each sample, the flowrate was chosen at 50% of the maximum flowrate determined by the instrument during the priming phase. This led to shear rates between 1200 and 1600 $s^{-1}$. Newtonian behavior was assumed for all samples.

Viscosity as a Function of Concentration

At pH 5.5, viscosity increased from 16 mPa·s at a concentration 126 mg/mL to 54 mPa·s at 154 mg/mL. At pH 7.0, viscosity increased from 5.8 mPa·s to 11 mPa·s in the same range of concentration. For all conditions, data were fit using Mooney equation:

$$\frac{\eta}{\eta_{solv}} = \exp\left(\frac{[\eta]c}{1 - \frac{K}{S}[\eta]c}\right)$$

where $\eta_{solv}$ is the viscosity of the solvent, $[\eta]$ the intrinsic viscosity of the protein, K a "crowding factor" and S a "shape factor". The fitting parameters were $[\eta]$ and K/S. A fixed value was used for $\eta_{solv}$=1.26 mPa·s, corresponding to the viscosity of the formulation buffer at 20° C.

As shown in FIG. 8, the viscosity of isatuximab solutions increased with increasing mAb concentration.

Viscosity as a Function of pH

Figure 9:
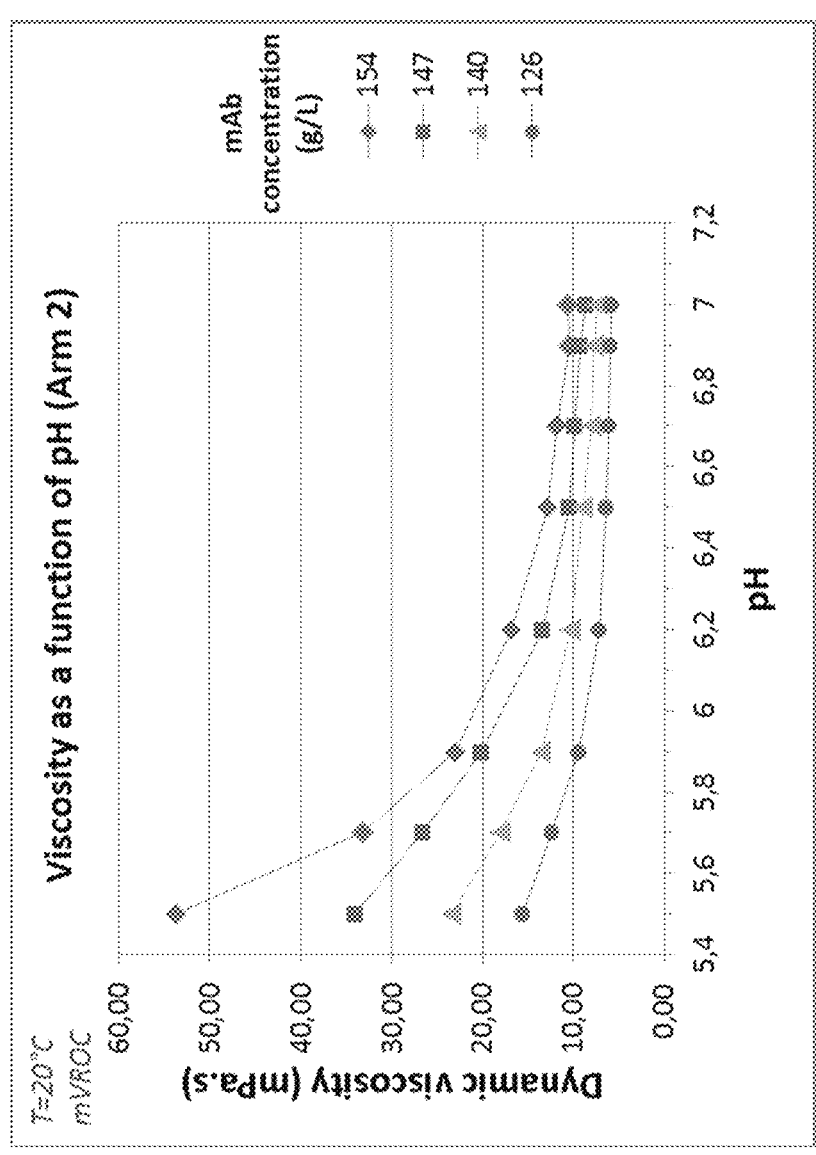
FIG. 9 is a graph depicting viscosity plotted as a function of pH, at mAb concentrations 126, 140, 147 and 154 g/L (T=20° C.).

FIG. 9 shows data obtained with m-VROC in Arm 2, viscosity plotted as a function of pH for 5 concentrations of isatuximab (126, 140, 147 and 154 mg/mL). As shown in FIG. 9, the viscosity of isatuximab solutions decreased with increasing pH.

At pH 6.2, the viscosity was less than 25 mPa·s across the concentration range of antibody tested. The viscosity was less than 25 mPa·s for all pH values higher than or equal to 5.9. However, at lower probed pH values (5.5 and 5.7), the viscosity was higher than 25 mPa·s for mAb concentrations higher or equal to 147 g/L.

Viscosity as a Function of Temperature

Figure 10:
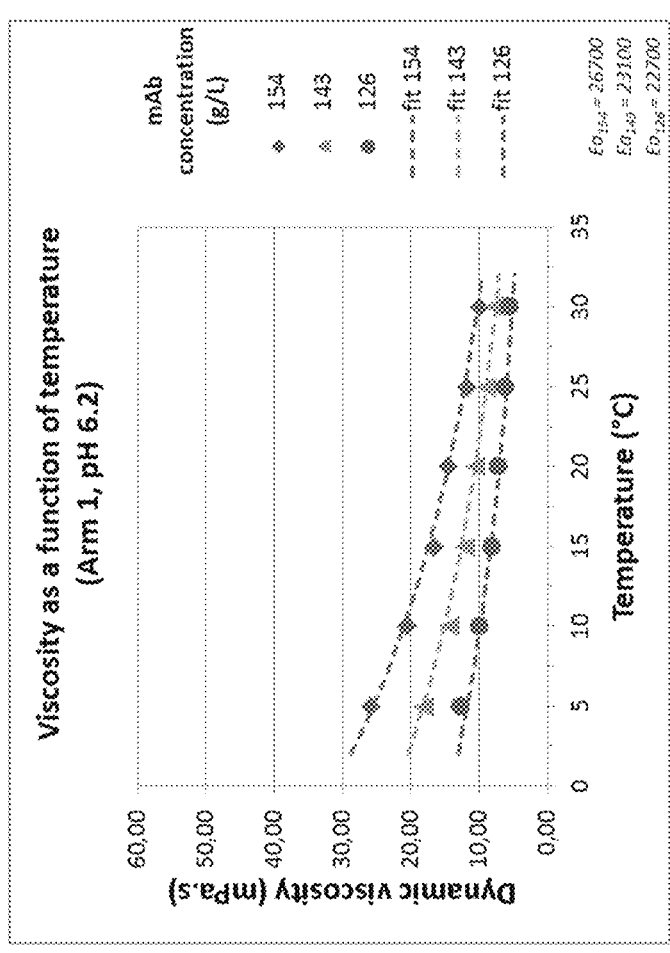
FIG. 10 is a graph depicting viscosity plotted as a function of temperature, at mAb concentrations 126, 143, and 154 g/L (pH=6.2).
Figure 11:
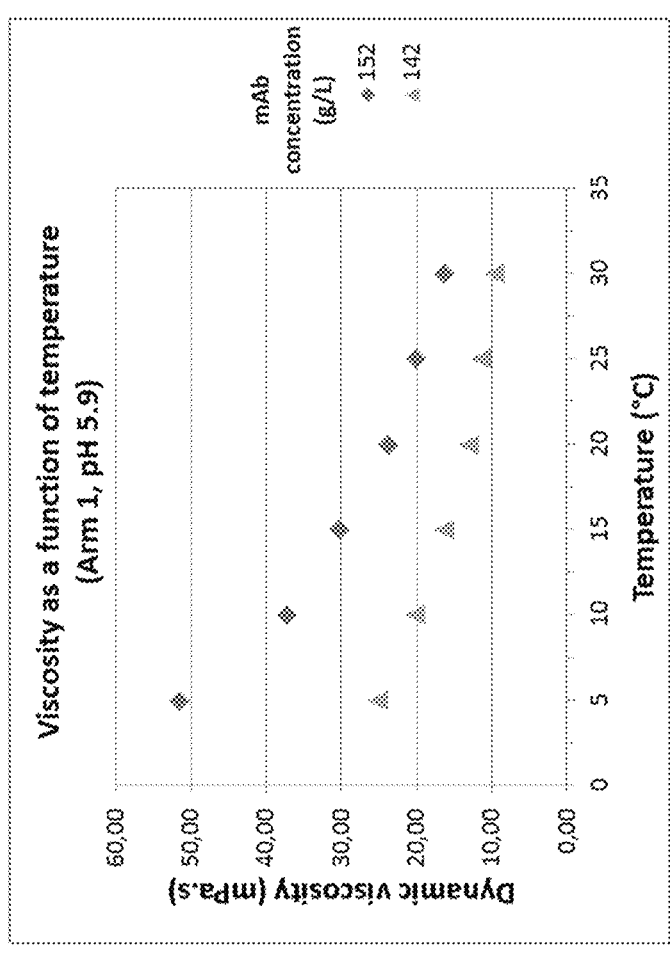
FIG. 11 is a graph depicting viscosity plotted as a function of temperature, at mAb concentrations 142, and 152 g/L (pH=5.9).

In Arm 1, the viscosity of the probed formulations was measured as a function of temperature between 5 and 30° C. As shown in FIG. 10 and FIG. 11, the viscosity decreased as temperature increased. Using an Arrhenius fit, the activation energy of the formulations was determined (Table 9). The values were used, in combination with a fit of data at 20° C. with Mooney equation, to calculate theoretical values. As shown in FIG. 10, the model coincided with the experimental data.

TABLE 9

Activation energy for the different formulations of Arm 1

| isatuximab concentration (g/L) | pH | Activation energy (kJ/mol) |
|---|---|---|
| 126 | 6.2 | 22.7 |
| 142 | 5.9 | 27.1 |
| 143 | 6.2 | 23.1 |
| 142 | 6.5 | 23.6 |
| 141 | 6.8 | 24.0 |
| 152 | 5.9 | 31.6 |
| 154 | 6.2 | 26.7 |

Activation energies increased with increasing concentration of isatuximab. Activation energies decreased between pH 5.9 and 6.2. To a lesser extent, activation energies increased between pH 6.2 and 6.8. In order to move in solution, a mAb must escape from its neighbors, and so needs a minimum energy that is defined here as Ea. The probability that the mAb can acquire this energy is proportional to exp(−Ea/RT) according to the Boltzmann law and thus the viscosity which is inversely proportional to the mobility of mAbs follow the equation viscosity=exp(+Ea/RT).

For formulations at pH 6.2, with mAb concentrations of 143 and 126 mg/mL, the viscosity remained under 25 mPa·s over the temperature range 5-30° C. At 154 mg/mL, the value recorded at 5° C. was slightly higher than 25 mPa·s.

For formulations at pH 5.9, the viscosity of isatuximab at 142 mg/mL was about 25 mPa·s at 5° C.

Viscosity as a Function of Arginine Concentration

Preliminary studies showed that, for a formulation of isatuximab at 150 mg/mL (without surfactant), the viscosity decreased from 60 mPa·s to 16 mPa·s between 0 and 100 mM of arginine, and only dropped to 12 mPa·s between 100 and 200 mM of arginine.

Figure 12:
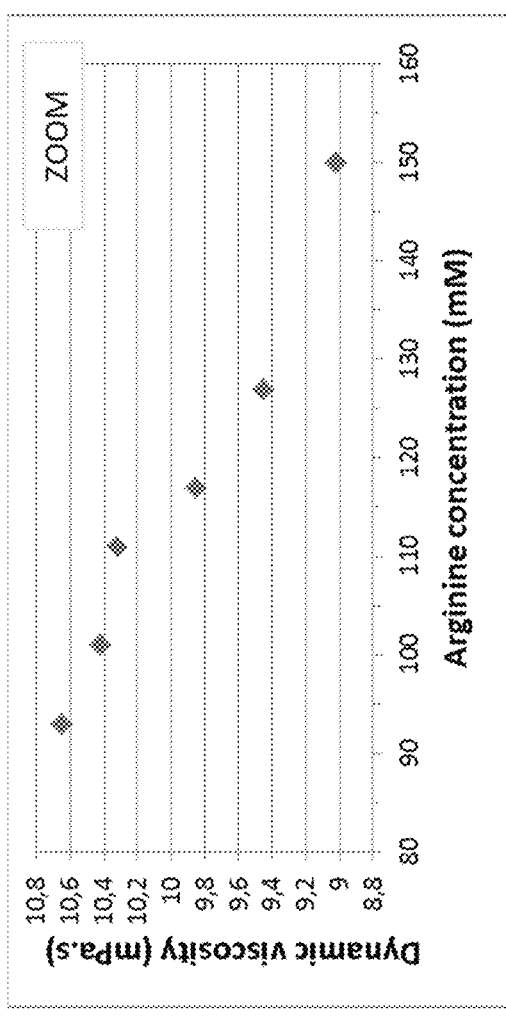
FIG. 12 is a graph depicting viscosity plotted as a function of arginine concentration, at mAb concentration 140 g/L (pH=6.2, T=20° C.).

In the present study, arginine concentrations from 90 to 150 mM, with points at 90, 100, 115, 125 and 150 mM were tested. The viscosity decreased with increasing concentrations of arginine (FIG. 12). The values decreased from 11 to 9 mPa·s, confirming the trend obtained in the preliminary studies.

In the range of arginine concentration studied (90-150 mM), the viscosity varied of less than 2 mPa·s.

Example 3—Stability

This example describes a series of stability studies in which 2 sets of formulations were subjected to a stability study at 5° C. and to an accelerated stability study at 40° C./75% r.h. as well as to a freeze-thaw and shake stress testing studies.

Formulations that were tested are summarized in Table 10 and Table 11.

TABLE 10

| | | | F4-1 to F4-16 | | |
|---|---|---|---|---|---|
| Form-ulation | Protein concentration (mg/mL) | pH | Arginine-HCl concentration (mM) | Sucrose concentration (mg/mL) | P188 concentration (mg/mL) |
| 1* | 140 | 6.2 | 125 | 20 | 4.0 |
| 2 | 140 | 6.5 | 145 | 16 | 3.0 |
| 3 | 140 | 6.2 | 125 | 20 | 4.0 |
| 4 | 140 | 5.9 | 105 | 24 | 5.0 |
| 5 | 154 | 6.2 | 105 | 16 | 5.0 |
| 6 | 140 | 6.2 | 125 | 20 | 4.0 |
| 7 | 126 | 6.2 | 145 | 24 | 3.0 |
| 8 | 154 | 5.9 | 125 | 24 | 3.0 |
| 9 | 140 | 6.2 | 125 | 20 | 4.0 |
| 10 | 126 | 6.5 | 125 | 16 | 5.0 |
| 11 | 154 | 5.9 | 145 | 20 | 5.0 |
| 12 | 126 | 6.5 | 105 | 20 | 3.0 |
| 13 | 140 | 6.2 | 125 | 20 | 4.0 |
| 14 | 154 | 6.5 | 145 | 24 | 4.0 |
| 15 | 126 | 5.9 | 105 | 16 | 4.0 |
| 16 | 140 | 6.2 | 125 | 20 | 4.0 |

*1 was tested as part of the accelerated study.

TABLE 11

| | | | F10-1 to F10-16 | | |
|---|---|---|---|---|---|
| Form-ulations | Protein concentration (mg/mL) | pH | Lysine acetate concentration (mM) | Sucrose concentration (mg/mL) | PS80 concentration (mg/mL) |
| 1* | 140 | 6.2 | 125 | 20 | 0.4 |
| 2 | 140 | 6.5 | 145 | 16 | 0.3 |
| 3 | 140 | 6.2 | 125 | 20 | 0.4 |
| 4 | 140 | 5.9 | 105 | 24 | 0.5 |
| 5 | 154 | 6.2 | 105 | 16 | 0.5 |
| 6 | 140 | 6.2 | 125 | 20 | 0.4 |
| 7 | 126 | 6.2 | 145 | 24 | 0.3 |
| 8 | 154 | 5.9 | 125 | 24 | 0.3 |
| 9 | 140 | 6.2 | 125 | 20 | 0.4 |
| 10 | 126 | 6.5 | 125 | 16 | 0.5 |
| 11 | 154 | 5.9 | 145 | 20 | 0.5 |
| 12 | 126 | 6.5 | 105 | 20 | 0.3 |
| 13 | 140 | 6.2 | 125 | 20 | 0.4 |
| 14 | 154 | 6.5 | 145 | 24 | 0.4 |

TABLE 11-continued

| | | | F10-1 to F10-16 | | |
|---|---|---|---|---|---|
| Form-ulations | Protein concentration (mg/mL) | pH | Lysine acetate concentration (mM) | Sucrose concentration (mg/mL) | PS80 concentration (mg/mL) |
| 15 | 126 | 5.9 | 105 | 16 | 0.4 |
| 16 | 140 | 6.2 | 125 | 20 | 0.4 |

*1 was tested as part of the accelerated study.

Freeze-thaw stress was performed by using an Epsilon1-6CC freeze-thaw unit (Martin Christ GmbH, Osterode, Germany). Samples were subjected to freeze-thawing stress.

One vial from each formulation (F4 and F10) was placed in a freeze-dryer and cycles were run according to the following parameters: speed, 0.1° C./min; freeze temperature, −30° C.; thaw temperature, 25° C.; number of cycles, 5; and hold-on temperature time, 60 min. After five cycles, samples were inspected for visual particles and were homogenized.

One vial of each formulation was mounted onto a horizontal shaking platform (IKA, KS4000 IC) and was stressed at 25° C. and 300 rpm for 21 days. T-mech samples were analyzed together with the T-1 month time point.

Osmolality of the samples was measured by a freezing-point depression method by using a Gonotec Osmomat 3000 (Gonotec, Berlin, Germany). A 3-point calibration was conducted prior to operation of the instrument, which included Milli-Q water and two osmolality standards at 300 and 400 mOsmol/kg.

Protein concentration was determined by UV spectroscopy performed in 96-well plates (Corning Incorporation, NY, USA) on a Tecan Safire2 plate reader (Tecan Austria GmbH, Grodig, Austria). The samples were diluted gravimetrically from 150 mg/mL solution to a protein concentration of 1 mg/mL. Dilution factors were calculated from balance printouts. For each data point, three wells (n=3) filled with 200 μL solution were measured to minimize measurement errors. The temperature of the measurement cell was set to 25° C. Dilution buffer was measured as blank spectrum. After measurement, the absorbance values obtained at 280 nm were corrected for the path length and subtracted with the corresponding blank. The calculated molar extinction coefficient ($\varepsilon_{molar}$) 224,320 $M^{-1}$ $cm^{-1}$ at 280 nm was used for calculation of the extinction coefficient (c). The calculated extinction coefficient ($\varepsilon$) of 1.548 mL $mg^{-1}$ $cm^{-1}$ was used to determine the protein concentration based on the absorbance values at 280 nm.

The vials were inspected for the presence or absence of visible particles under gentle, manual, radial agitation for 5 seconds in front of a white background and for 5 seconds in front of a black background according to the European Pharmacopoeia (8th edition; monograph 2.9.20) at ca. 3750 lux. The inspection was performed independently by two trained examiners.

To classify the observed visible particles, a number score on the basis of the "Deutscher Arzneimittel-Codex" (DAC 2006) was used (0, no particles visible within 5 sec; 1, few particles visible within 5 sec; 2, medium number of particles visible within 5 sec; 10, large number particles directly visible). Fiber-like structures and particles that are likely non-inherent to the product are not accounted for by the number score.

High Performance Size-Exclusion Chromatography (HP-SEC)

Prior to sample analysis, the performance of the HP-SEC column was tested with the BioRad gel filtration standard (containing thyroglobulin, gamma globulin, ovalbumin, myoglobin, and vitamin B12). The standard was prepared by solubilizing the lyophilized material in 500 µL of Milli-Q water, followed by a 10-fold dilution in mobile phase (final protein concentration 3.6 mg/mL). The system suitability test was performed at the beginning of each sequence by injecting the gel filtration standard (BioRad) and assessed by calculating the USP resolution between the gamma globulin and the ovalbumin peak. 50 mg/mL stock samples were diluted 5-fold in the 1.5 mL polypropylene tubes (Eppendorf) by mixing 40 µL of stock solution with 160 µL of solution A (mobile phase without acetonitrile), resulting in a protein concentration of 10.0 mg/mL.

To avoid blocking of the HP-SEC column by larger, insoluble particles that might potentially form during accelerated stability/stress testing, samples were centrifuged after dilution at 18,000 rcf for 5 min, and the supernatant was transferred into the HPLC vials. The samples were vortexed and stored at 5° C. in the autosampler until the analysis.

The following parameters were used for the HP-SEC analysis:

Instrument: Ultimate 3000 (Dionex)

Column: Amorphous silica column ProSEC 300S; 300 mm

Security guard: Guard column 50 mm×7.5 mm

Flow rate: 0.3 mL/min

Mobile phase: 90% of 100 mM Phosphate, pH 7.2, 300 mM $NaClO_4$+10% ACN

Detection: UV at 280 nm and at 214 nm

Column oven: 25° C.

Sample cooling: 5-8° C.

Injection volume: 10 µL for 5.0 mg/mL sample, 10 µL for blanks and SEC standards Analysis time: 90 min

Capillary Isoelectric Focusing (cIEF)

Imaged capillary isoelectric focusing (cIEF) was performed on an iCE280 instrument coupled to PrinCE Micro-injector (Convergent Bioscience, Toronto, Canada). Instead of eluting the focused molecular species past a fixed detection point, as practiced in conventional cIEF, in imaged cIEF the molecules are detected across the whole IEF capillary. To do so, UV light at a wavelength of 280 nm was focused on the UV-transparent capillary, and images were captured in regular intervals by aid of a charge-coupled device (CCD) camera.

Prior to analysis, the fused, silica-coated (FC) cartridge was installed following the instrument instructions. The anode reservoir was filled with 0.08 M phosphoric acid (in 0.1% methylcellulose, electrolyte kit, ProteinSimple) and the cathode reservoir with 0.1 M sodium hydroxide (in 0.1% methylcellulose, electrolyte kit, ProteinSimple). The performance of the system was checked by measuring a hemoglobin standard (iCE280 System Suitability Kit, ProteinSimple). Isoelectric focusing of the hemoglobin standard solution was carried out according to the manufacturer (pre-focusing:1 min at 1500 V; focusing: 4.5 min at 3000 V).

The Master Mix for 20 samples was prepared by mixing 2360 µL of Milli-Q water, 1400 µL of 1% methylcellulose, 160 µL of Pharmalyte pH 3-10, 20 µL of pI marker 7.05 and 20 µL of pI marker 9.50. Master Mix was homogenized by vortexing and shortly centrifuged at 5,000 rcf. The mix was filtrated with a 0.45 µm syringe PVDF filter unit (Millex-GV, Millipore).

The samples were pre-diluted to a protein concentration of 20.0 mg/mL by mixing 20 µL of the stock solutions (C=50 mg/mL) with 30 µL of the corresponding formulation buffers. Final samples for the cIEF analysis was prepared by mixing 2 µL of the pre-diluted samples at 20.0 mg/mL with 198 µL Master Mix to obtain a total volume of 200 µL and a protein concentration of 0.2 mg/mL.

Isoelectric focusing of the DP was carried out by pre-focusing for 1 min at 1500 V, followed by focusing for 8 min at 3000 V. The UV absorption images were analyzed by using the software ChromPerfect (Version 5.5.6).

Results of Visual Inspection

Visual inspection was performed by two independent operators Sample solutions after freeze-thawing were marked as inhomogeneous (S-Schlieren*, phase separation). No major changes in visible particle content and turbidity were observed for all tested formulations during the stability study.

The results of the osmolality measurements are presented in Table 12. At T0, osmolalities ranged between 275-418 mOsmol/kg. The F10 Formulations showed higher osmolality values than the F4 Formulations. Storage at 40° C./75% r.h. had no influence on the osmolality in tested samples.

TABLE 12

| Results of osmolality measurements at T0 (n = 1) | |
| --- | --- |
| Sample | Osmolality |
| F4-1 | 335 |
| F4-2 | 353 |
| F4-3 | 331 |
| F4-4 | 308 |
| F4-5 | 280 |
| F4-6 | 336 |
| F4-7 | 378 |
| F4-8 | 353 |
| F4-9 | 334 |
| F4-10 | 320 |
| F4-11 | 391 |
| F4-12 | 289 |
| F4-13 | 335 |
| F4-14 | 404 |
| F4-15 | 277 |
| F4-16 | 330 |
| F10-1 | 353 |
| F10-2 | 381 |
| F10-3 | 341 |
| F10-4 | 310 |
| F10-5 | 276 |
| F10-6 | 346 |
| F10-7 | 401 |
| F10-8 | 374 |
| F10-9 | 343 |
| F10-10 | 328 |
| F10-11 | 394 |
| F10-12 | 294 |
| F10-13 | 365 |
| F10-14 | 418 |
| F10-15 | 275 |
| F10-16 | 351 |

TABLE 13

| Results of osmolality measurements at T-1w_40° C., T-2w_40° C., and T-1m_40° C. | | | |
| --- | --- | --- | --- |
| | Osmolality | | |
| Sample | T-1w_40° C. | T-2w_40° C. | T-1m_40° C. |
| F4-1 | 326 | 326 | 324 |
| F10-1 | 342 | 343 | 344 |

The results of the viscosity measurements at T0 indicated that the F10 Formulations showed slightly higher viscosities than the F4 Formulations. The highest viscosity was measured for Formulation F4-8 (30.03 cP at 1000 s$^{-1}$ at 20° C.) and F10-8 (34.13 cP at 1000 s$^{-1}$ at 20° C.). For both sets of formulations (F4 and F10), Run 8 contained the highest protein concentration (154 mg/mL), the lowest pH (5.9), and the highest sucrose concentration (24 mg/mL).

The results of the protein concentration determination by UV spectroscopy are provided in Table 14 and Table 15. At T0, the protein concentrations ranged between 124 and 156 mg/mL. The protein concentration in the test formulations remained stable during storage at 40° C./75% r.h.

TABLE 14

Protein concentration

| | | Protein concentration (mg/mL) | | | |
|---|---|---|---|---|---|
| Sample | Target | T0 | T-mech | T-FT | T-1m_40° C. |
| F4-1 | 140 | 135.0 | 139.5 | 141.2 | 140.9 |
| F4-2 | 140 | 135.0 | 138.3 | 138.1 | 139.8 |
| F4-3 | 140 | 137.1 | 138.8 | 139.7 | 136.7 |
| F4-4 | 140 | 138.5 | 135.7 | 139.9 | 140.3 |
| F4-5 | 154 | 151.8 | 150.9 | 153.6 | 154.4 |
| F4-6 | 140 | 136.9 | 139.0 | 141.2 | 138.6 |
| F4-7 | 126 | 123.7 | 125.9 | 127.5 | 125.6 |
| F4-8 | 154 | 154.2 | 151.9 | 151.9 | 151.3 |
| F4-9 | 140 | 138.5 | 138.0 | 142.1 | 139.2 |
| F4-10 | 126 | 124.1 | 124.6 | 126.2 | 126.4 |
| F4-11 | 154 | 154.4 | 153.3 | 154.1 | 156.0 |
| F4-12 | 126 | 121.0 | 123.4 | 124.9 | 124.3 |
| F4-13 | 140 | 140.0 | 136.8 | 140.2 | 137.1 |
| F4-14 | 154 | 151.5 | 147.4 | 152.5 | 158.0 |
| F4-15 | 126 | 124.1 | 122.7 | 122.3 | 125.1 |
| F4-16 | 140 | 137.1 | 140.9 | 136.7 | 139.3 |
| F10-1 | 140 | 138.4 | 141.8 | 140.7 | 146.0 |
| F10-2 | 140 | 141.6 | 139.1 | 141.6 | 144.4 |
| F10-3 | 140 | 140.6 | 141.7 | 139.2 | 141.7 |

TABLE 14-continued

Protein concentration

| | | Protein concentration (mg/mL) | | | |
|---|---|---|---|---|---|
| Sample | Target | T0 | T-mech | T-FT | T-1m_40° C. |
| F10-4 | 140 | 139.4 | 138.8 | 140.2 | 141.0 |
| F10-5 | 154 | 154.3 | 156.4 | 152.2 | 157.2 |
| F10-6 | 140 | 141.1 | 142.4 | 142.7 | 142.0 |
| F10-7 | 126 | 129.9 | 126.1 | 128.4 | 130.3 |
| F10-8 | 154 | 153.9 | 155.9 | 159.2 | 156.2 |
| F10-9 | 140 | 140.2 | 140.3 | 141.9 | 140.2 |
| F10-10 | 126 | 126.5 | 127.1 | 128.7 | 129.8 |
| F10-11 | 154 | 154.5 | 152.7 | 152.7 | 155.4 |
| F10-12 | 126 | 125.3 | 126.1 | 125.1 | 127.3 |
| F10-13 | 140 | 141.1 | 140.9 | 140.1 | 141.8 |
| F10-14 | 154 | 158.8 | 155.2 | 156.2 | 157.1 |
| F10-15 | 126 | 123.8 | 127.1 | 126.6 | 125.3 |
| F10-16 | 140 | 141.7 | 142.6 | 138.1 | 142.4 |

TABLE 15

Protein Concentration

| | Protein Concentration (mg/mL) | |
|---|---|---|
| Sample | T-1w_40° C. | T-2w_40° C. |
| F4-1 | 137.1 | 140.2 |
| F10-1 | 142.3 | 144.6 |

Sodium dodecyl sulfate gel electrophoresis (SDS-PAGE) was used to characterize molecular weights and relative quantities of protein species. Relative amounts of separated species were calculated from SDS-PAGE gels by measuring the optical density of detected protein bands. The relative quantities and molecular weights of all detected protein species under non-reducing and reducing conditions are found in Table 16 and Table 17, respectively.

TABLE 16

Relative quantity and calculated molecular weights of species detected by non-reducing SDS-PAGE

| | Relative quantity (%) | | | | | Molecular weight (kDa) | | | | |
|---|---|---|---|---|---|---|---|---|---|---|
| Sample | Aggregate | Major band | Fragment 1 | Fragment 2 | Fragment 3 | Aggregate | Major band | Fragment 1 | Fragment 2 | Fragment 3 |
| F4-1 T0 | 0.6 | 95.5 | 3.4 | 0.3 | 0.3 | 244.6 | 157.5 | 141.7 | 112.1 | 25.0 |
| F10-1 T0 | 0.7 | 95.1 | 3.8 | 0.3 | 0.2 | 241.5 | 158.5 | 142.6 | 112.3 | 24.8 |
| F4-1 T1w_40° C. | 0.9 | 94.9 | 3.6 | 0.5 | 0.3 | 242.5 | 157.5 | 142.0 | 111.7 | 25.1 |
| F10-1 T1w_40° C. | 1.1 | 95.0 | 3.3 | 0.5 | 0.2 | 242.5 | 159.1 | 142.9 | 110.7 | 24.8 |
| F4-1 T2w_40° C. | 1.0 | 95.6 | 2.2 | 0.8 | 0.5 | 244.9 | 157.4 | 142.1 | 110.6 | 25.4 |
| F10-1 T2w_40° C. | 1.1 | 94.8 | 3.1 | 0.7 | 0.3 | 247.6 | 158.1 | 142.7 | 110.4 | 25.1 |
| F4-1 T1m_40° C. | 0.9 | 94.9 | 3.1 | 1.0 | 0.2 | 251.7 | 159.7 | 144.0 | 111.2 | 24.8 |
| F10-1 T1m_40° C. | 1.0 | 95.1 | 2.9 | 0.9 | 0.2 | 249.3 | 159.3 | 144.5 | 111.4 | 24.7 |

TABLE 17

| | Relative quantity (%) | | | | Molecular weight (kDa) | | |
|---|---|---|---|---|---|---|---|
| Sample | N-R adduct | Heavy chain | Light chain | Purity (%) | N-R adduct | Heavy chain | Light chain |
| F4-1T0 | 0.6 | 67.1 | 32.3 | 99.4 | 80.9 | 50.6 | 25.4 |
| F10-1T0 | 0.8 | 65.9 | 33.4 | 99.3 | 82.3 | 50.6 | 25.3 |
| F4-1T1w_40° C. | 0.8 | 66.2 | 33.1 | 99.3 | 81.8 | 50.8 | 25.5 |
| F10-1T1w_40° C. | 0.7 | 66.5 | 32.8 | 99.3 | 81.6 | 50.6 | 25.2 |
| F4-1T2w_40° C. | 0.7 | 67.9 | 31.5 | 99.4 | 84.0 | 51.0 | 25.9 |
| F10-1T2w_40° C. | 0.6 | 68.6 | 30.9 | 99.5 | 86.1 | 51.4 | 26.0 |
| F4-1T1m_40° C. | 0.9 | 66.1 | 33.1 | 99.1 | 85.1 | 51.2 | 25.7 |
| F10-1T1m_40° C. | 1.2 | 65.3 | 33.6 | 98.9 | 85.9 | 51.4 | 25.8 |

High performance size-exclusion chromatography (HP-SEC) was performed to assess for monomer, aggregates, and fragments. Four aggregate species (HMW1, HMW2, HMW3 and HMW4) and two fragment species (LMW1 and LMW2) were assigned.

Figure 13:
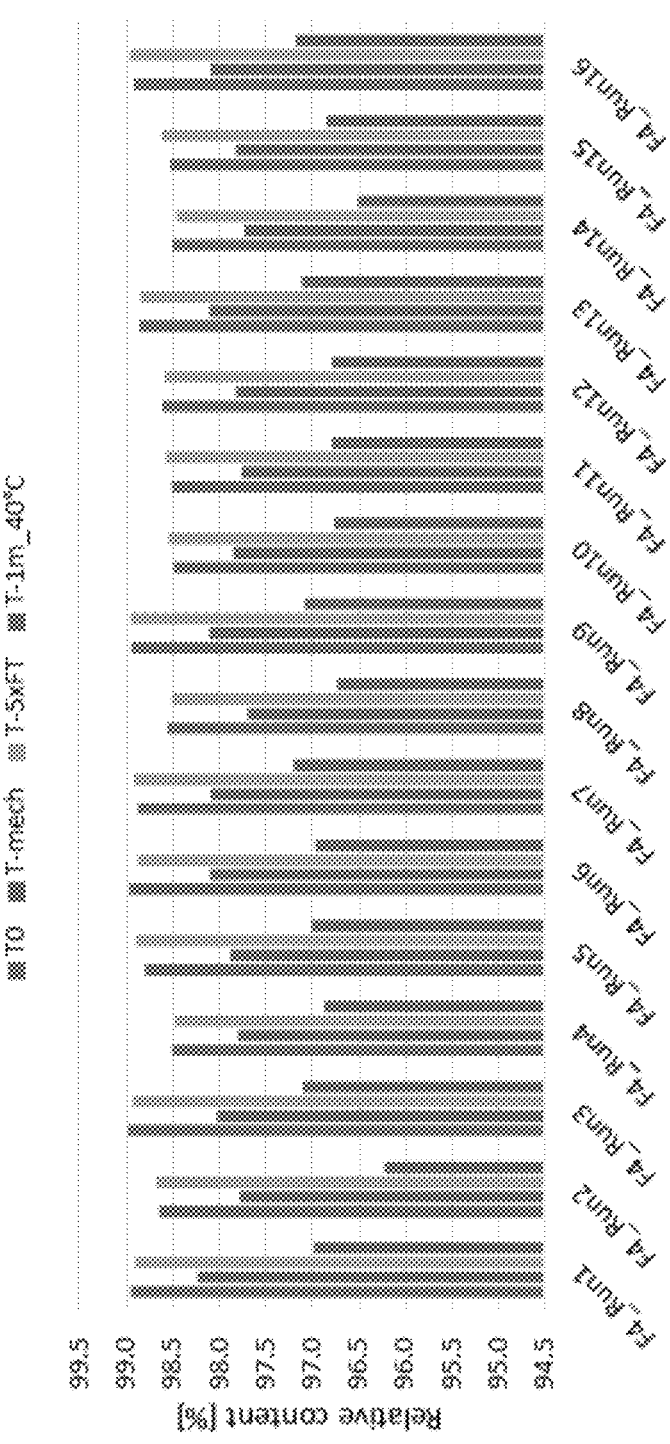
FIG. 13 is a graph depicting relative monomer content detected using HP-SEC analysis of isatuximab in Formulations F4-1 to F4-16 (Run 1-Run 16, respectively, n=2, mean); T0: no treatment, T-mech: Mechanical stress, T-5× FT: 5 Freeze/Thaw cycles, T-1m_40° C.: 1 month at 40° C.
Figure 14:
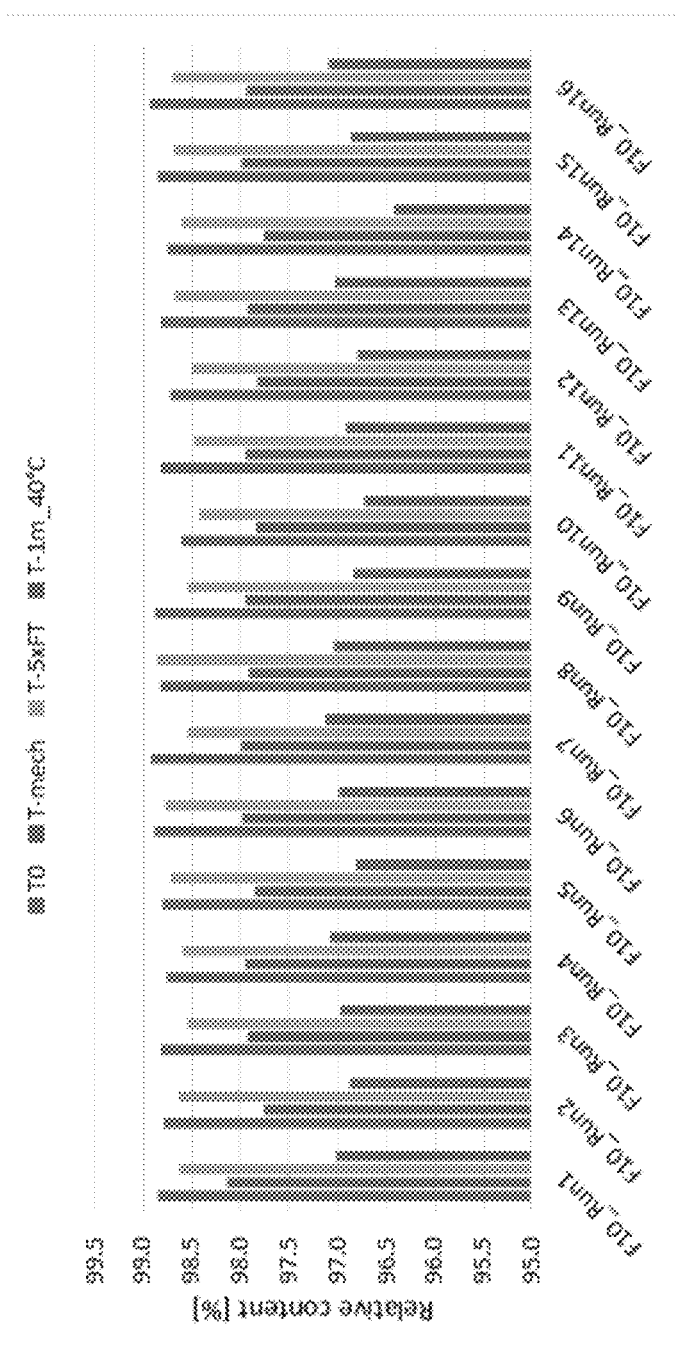
FIG. 14 is a graph depicting relative monomer content detected using HP-SEC analysis of isatuximab in Formulations F10-1 to F10-16 (Run 1-Run 16, respectively, n=2, mean); T0: no treatment, T-mech: Mechanical stress, T-5xFT: 5 Freeze/Thaw cycles, T-1m_40° C.: 1 month at 40° C.

At T0, the relative monomer content in Formulations F4 and F10 ranged between 98.5-99.0%. Storage at 40° C./75% r.h. led to a decrease of the monomer content in all tested samples. The monomer content in the test formulations after storage at 40° C./75% r.h. for one month ranged between 96.2-97.2%; the lowest monomer content at this time point was found in Formulation F4-2. Repeated freeze-thaw cycles had almost no impact on the relative monomer content, while mechanical stress led to a small decrease (97.7-98.2%). See FIG. 13 and FIG. 14.

For almost all samples and time points, the relative content of HMW1 was below the limit of quantitation of 0.15%, and similarly, for almost all samples and time points, the relative content of HMW2 was below the limit of quantitation of 0.15%.

The relative content of HMW3 was in the range of 0.7-0.9% at T0. After one month storage at 40° C./75% r.h., the HMW3 content increased to 1.1-1.5%. The highest increase in HMW3 content was observed in F4-14, F10-5, F10-12 and F10-14 samples, while the lowest increase was observed in Formulation F4-1 and F4-7 samples. Repeated freeze-thaw cycles did not result in an increase of the HMW3 relative content, while mechanical stress led to a slight HMW3 increase to 0.9-1.2%.

For almost all samples and time points, the relative content of HMW4 was below the limit of quantitation of 0.15%.

Figure 15:
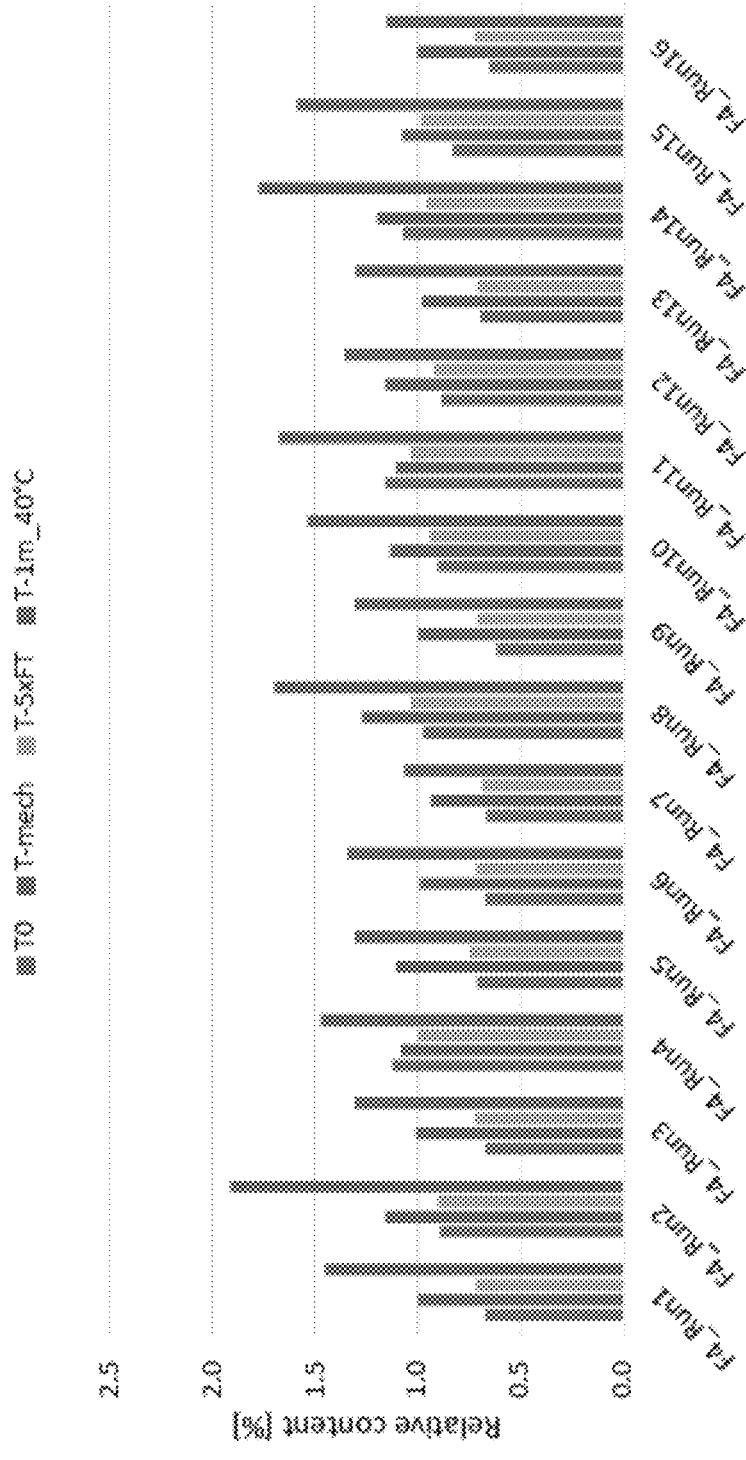
FIG. 15 is a graph depicting relative content of all aggregates (HMWS) detected using HP-SEC analysis of isatuximab in Formulations F4-1 to F4-16 (Run 1-Run 16, respectively, n=2, mean); T0: no treatment, T-mech: Mechanical stress, T-5xFT: 5 Freeze/Thaw cycles, T-1m_40° C.: 1 month at 40° C.
Figure 16:
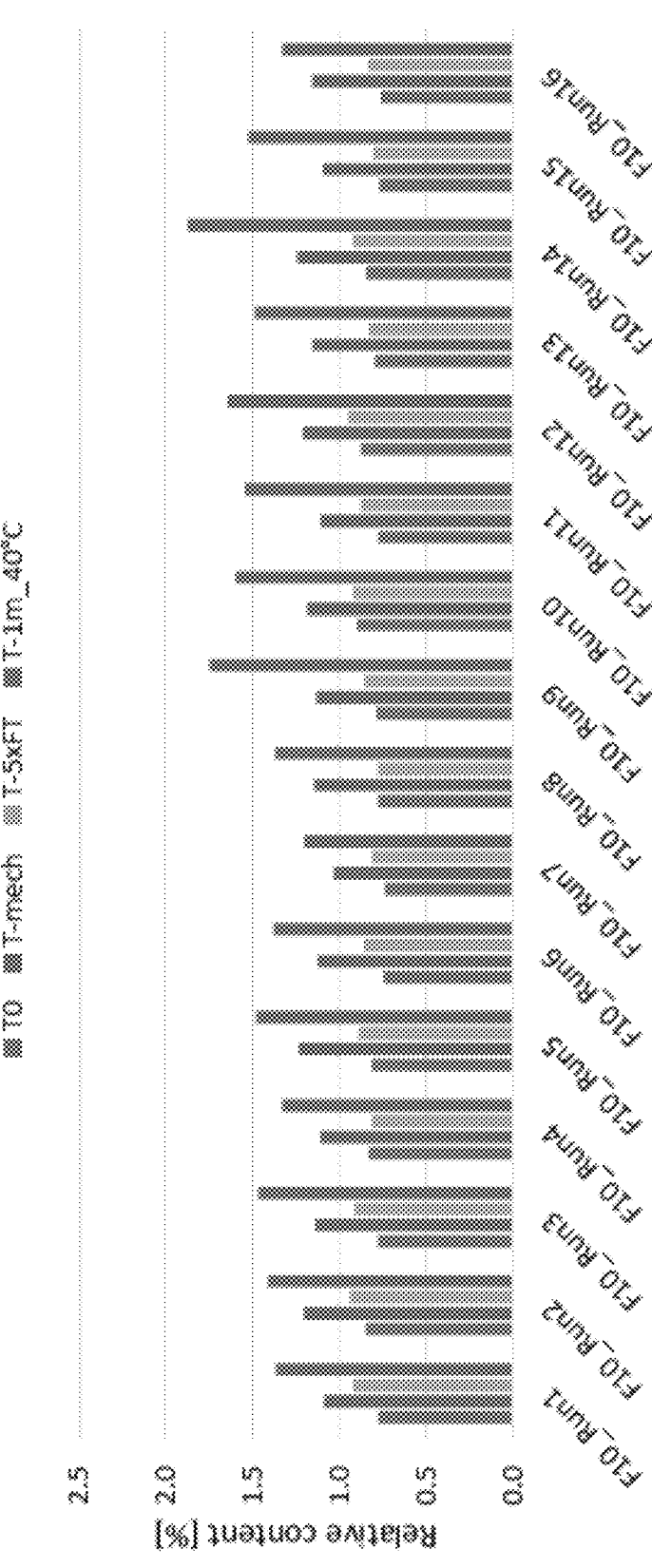
FIG. 16 is a graph depicting relative content of all aggregates (HMWS) detected using HP-SEC analysis of isatuximab in Formulations F10-1 to F10-16 (Run 1-Run 16, respectively, n=2, mean); T0: no treatment, T-mech: Mechanical stress, T-5xFT: 5 Freeze/Thaw cycles, T-1m_40° C.: 1 month at 40° C.

The sum of all aggregates (HMWS) was calculated with peaks ≥0.15% relative area. At T0, the total content of aggregates (HMWS) was in the range of 0.6-1.2%. Storage at 40° C./75% r.h. led to a notable increase of the HMWS content in all tested formulations. The relative HMWS content after storage at 40° C./75% r.h. for one month ranged between 1.1-1.9%. The lowest increase of HWM species was observed for Formulation F4-7, and the highest increase was observed for Formulations F4-2 and F10-14. No substantial changes in HMWS content were observed after freeze-thawing, and only small increases were detected after exposure to mechanical stress leading to a HWMS content between 0.9-1.3%. See FIG. 15 and FIG. 16).

At T0, the content of fragment LMW1 was about 0.3. Storage at 40° C./75% r.h. led to an increase of the LMW1 content in all tested samples. The relative LMW1 content was highest after storage at 40° C./75% r.h. for one month and ranged between 1.1-1.5%. Freeze-thawing had no influence on the LMW1 content. Mechanical stress led to a small increase in LMW1 content.

At T0, the relative content of fragment LMW2 was below the limit of quantification (≥0.15%) for all tested formulations. Storage at 40° C./75% r.h. for two weeks and one month led to a small increase of the LMW2 content, with the highest values observed at T-1m_40° C. (0.3-0.5%).

Figure 17:
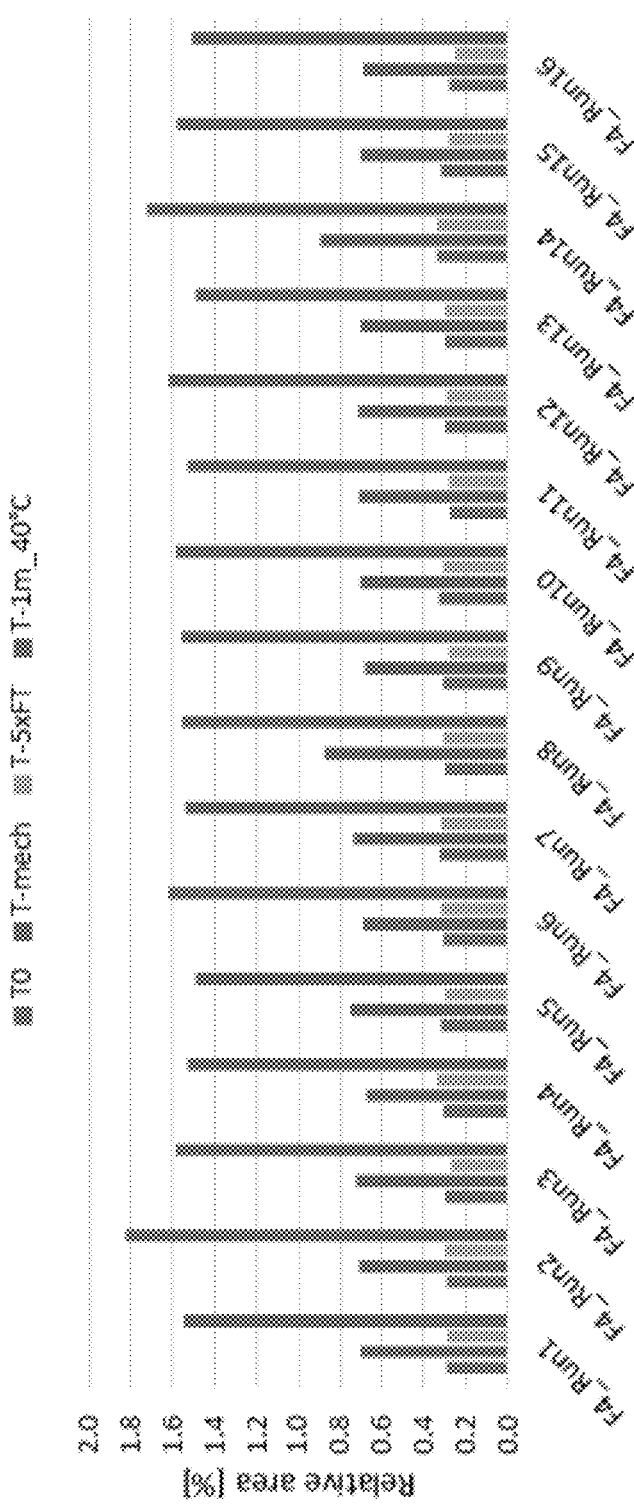
FIG. 17 is a graph depicting relative content of all fragments (LMWS) detected using HP-SEC analysis of isatuximab in Formulations F4-1 to F4-16 (Run 1-Run 16, respectively, n=2, mean); T0: no treatment, T-mech: Mechanical stress, T-5xFT: 5 Freeze/Thaw cycles, T-1m_40° C.: 1 month at 40° C.
Figure 18:
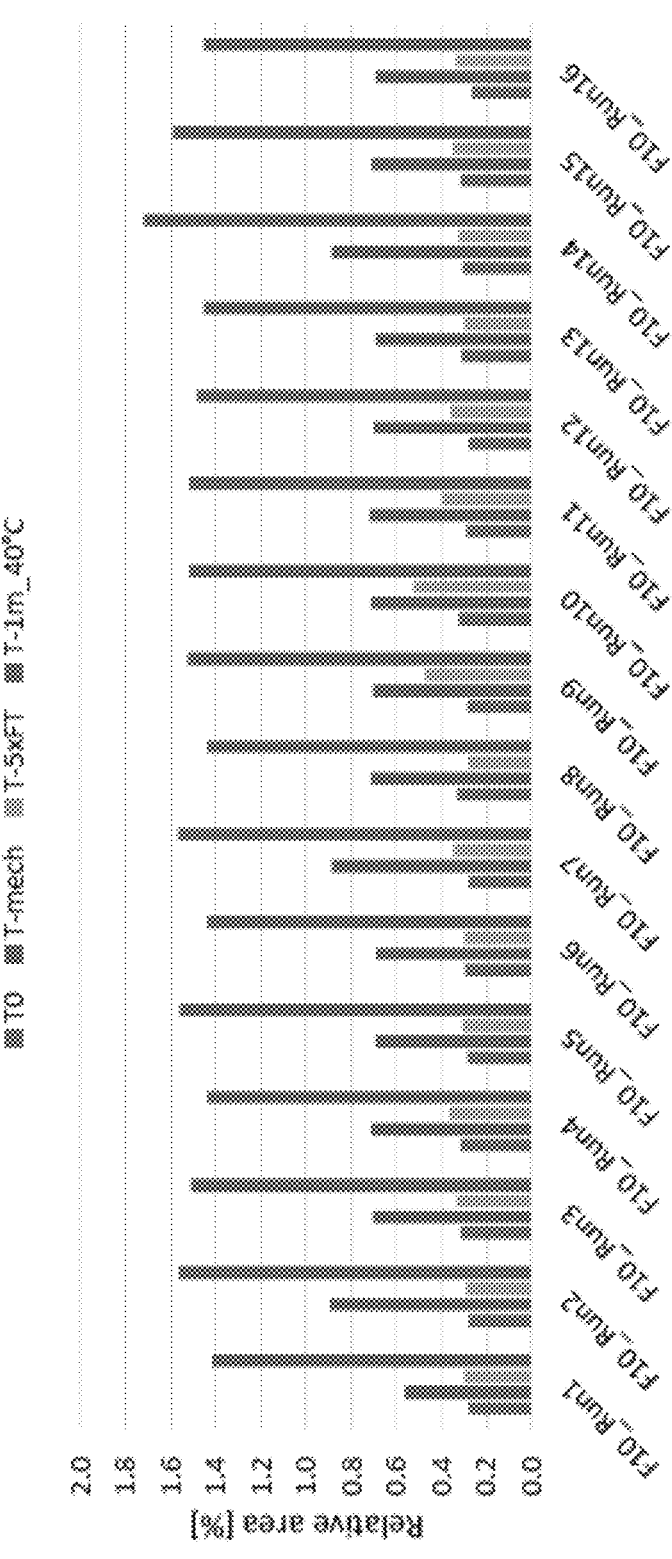
FIG. 18 is a graph depicting relative content of all fragments (LMWS) detected using HP-SEC analysis of isatuximab in Formulations F10-1 to F10-16 (Run 1-Run 16, respectively, n=2, mean); T0: no treatment, T-mech: Mechanical stress, T-5xFT: 5 Freeze/Thaw cycles, T-1m_40° C.: 1 month at 40° C.

The sum of the content of all LMWS was calculated with peaks ≥0.15%. At T0, the total LMWS content was about 0.3% in all tested formulations. Whereas freezethawing had no impact on the LMWS content, mechanical stress led to small increases in the LMWS content (0.7-0.9%). Storage at 40° C./75% r.h. led to more notable increases, especially at the later time points (FIG. 17 and FIG. 18). The highest increase was observed at T-1m_40° C., where the total LMWS content ranged between 1.4-1.8%.

At T0, the relative content of the main peak as measured by capillary isoelectric focusing (cIEF) was between 70.3-74.0%. A gradual decrease in the relative content of the main peak was detected after storage at 40° C./75% r.h. for one week, two weeks and one month. The highest decrease was observed for Formulation F10-8 (55.4% at T-1m_40° C.). The pI of the main peak remained stable at about 8.2 for all formulations at all stability time points.

Figure 19:
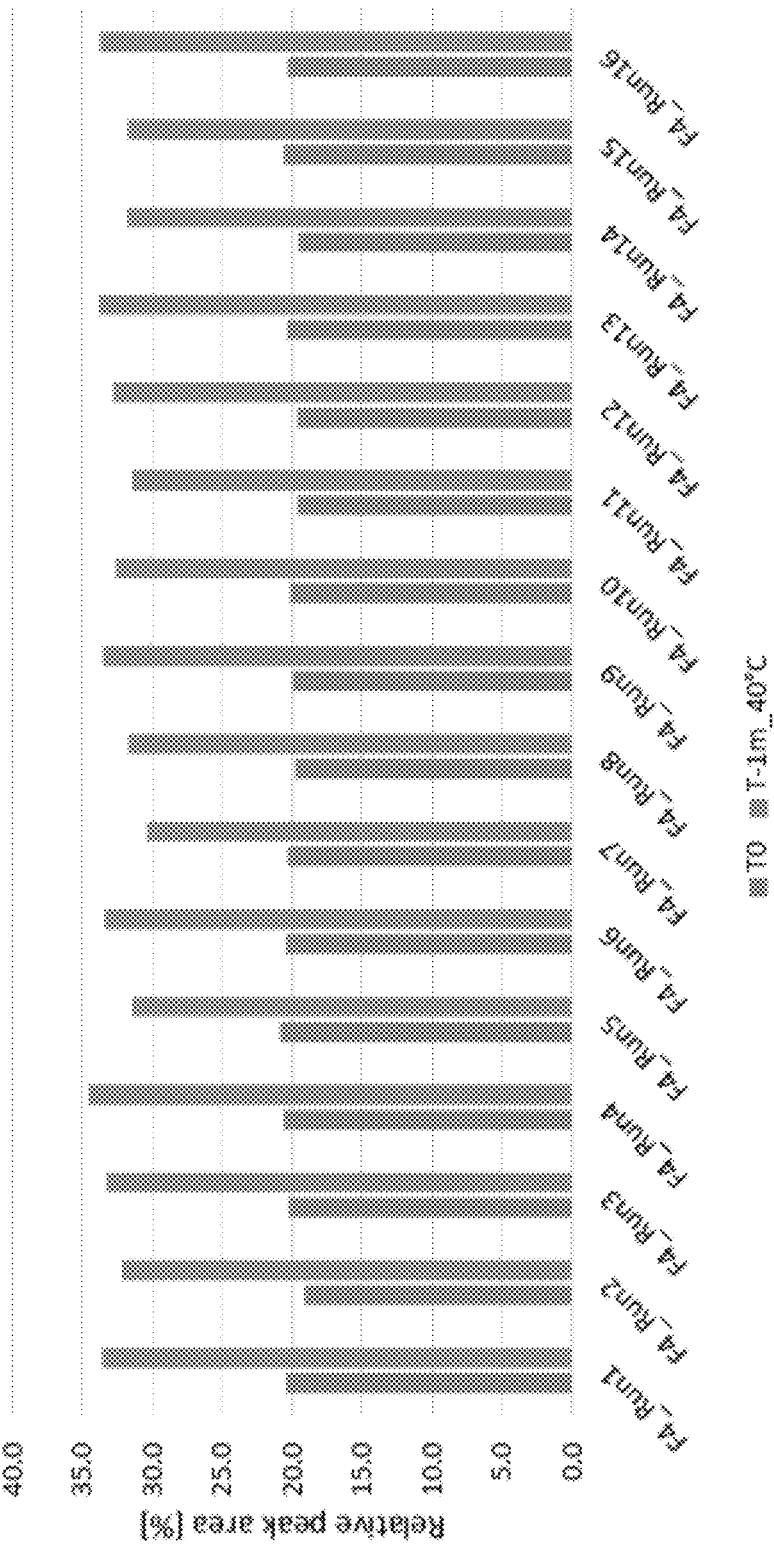
FIG. 19 is a graph depicting acidic peak content obtained from capillary isoelectric focusing (cIEF) analysis of isatuximab Formulations F4-1 to F4-16 (Run 1-Run 16, respectively, n=2, mean); T0: no treatment, T−1m_40° C.: 1 month at 40° C.
Figure 20:
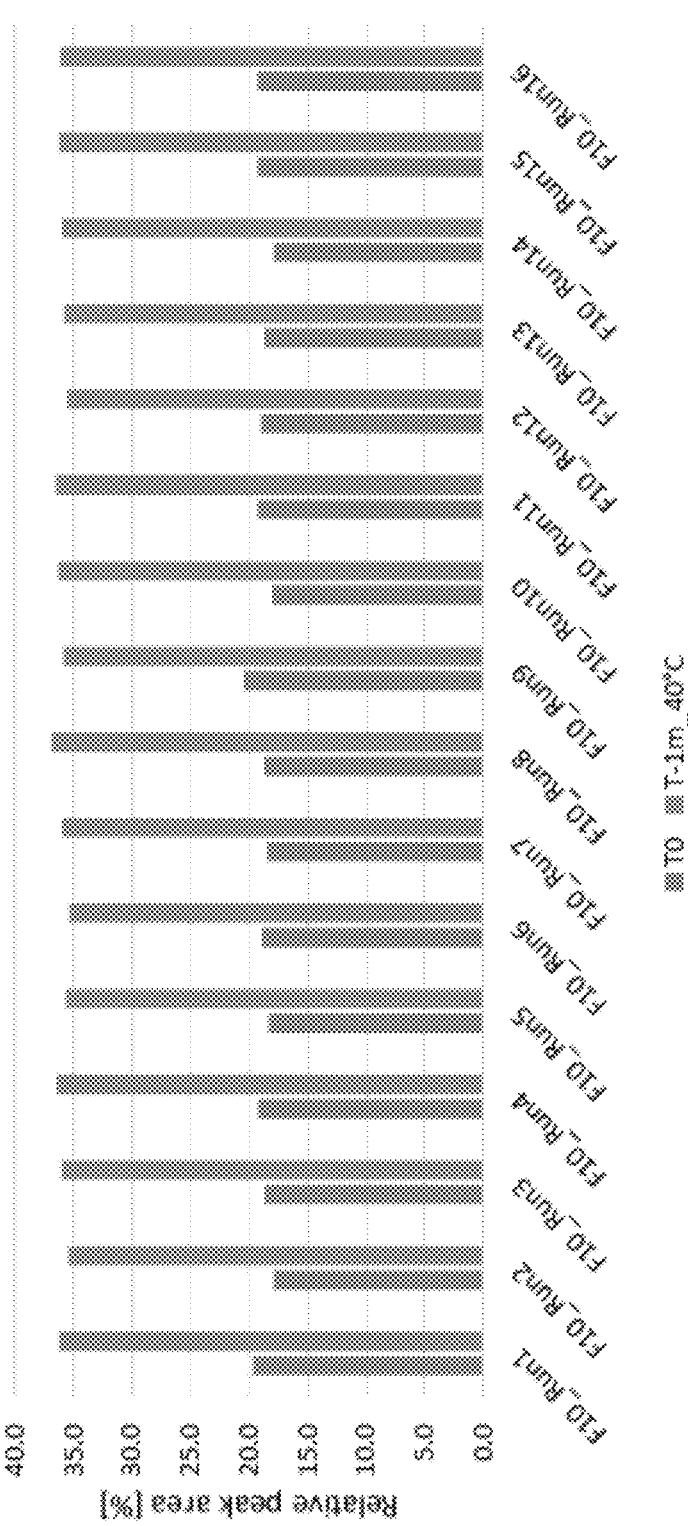
FIG. 20 is a graph depicting acidic peak content obtained from cIEF analysis of isatuximab in Formulations F10-1 to F10-16 (Run 1-Run 16, respectively, n=2, mean); T0: no treatment, T-1m_40° C.: 1 month at 40° C.

At T0, the relative content of acidic species ranged between ca. 17.9-20.9%. Storage at 40° C./75% r.h. led to a notable increase of acidic species content. The highest increase was observed at time point T-1m_40° C. with values between 30.4-36.9%. The highest increase was observed for Formulation F10-8, whereas Formulation F4-7 showed the lowest increase. A graphical representation of the data is shown in FIG. 19 and FIG. 20.

At T0, basic peak contents between 8.1-9.5% were observed. During the stability study, the basic peak content remained relatively stable for all formulations at most time points. For T-1m_40° C., the basic peak content ranged from 7.1-9.1%.

Figure 21:
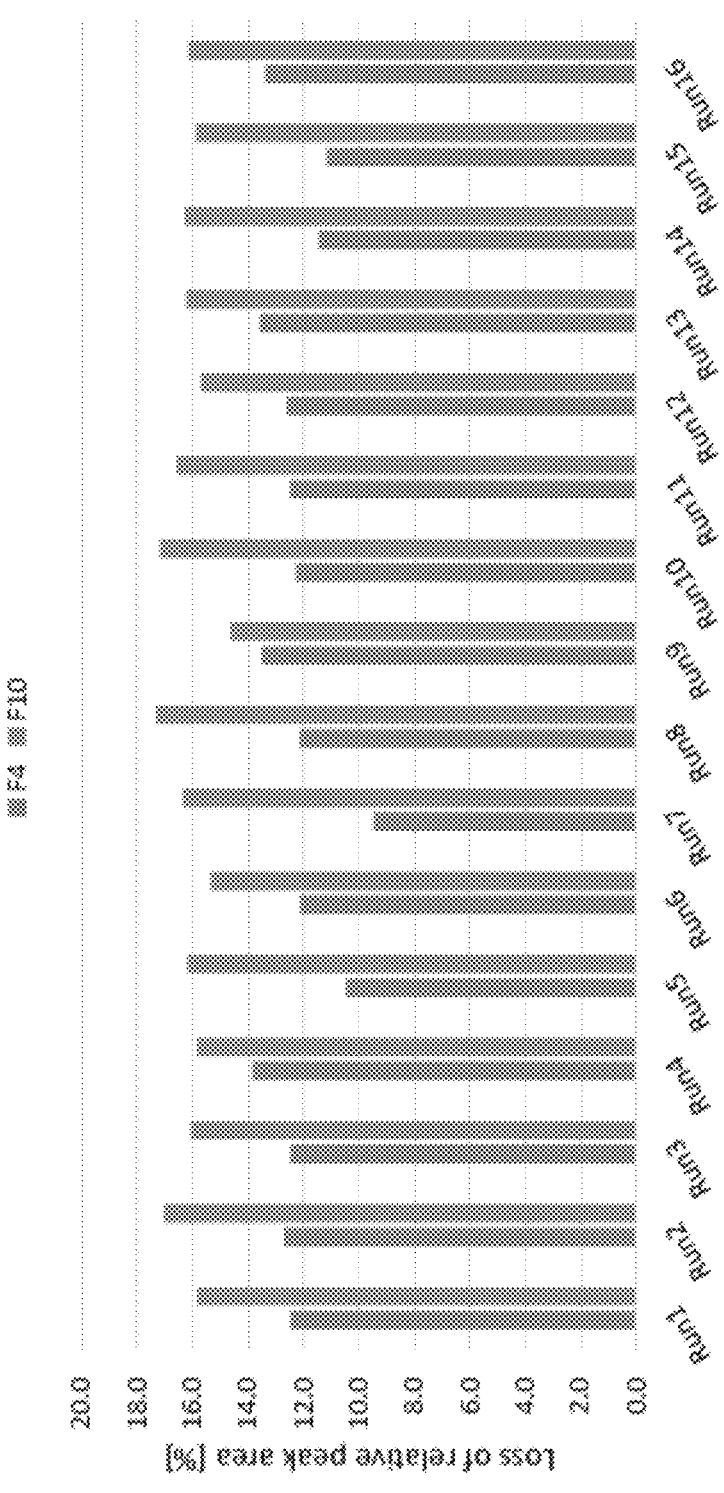
FIG. 21 is a graph depicting loss of relative area [%] of monomer peak content obtained from cIEF analysis of isatuximab in Formulations F4-1 to F4-16 and F10-1 to F10-16 after one month storage at 40° C./75% r.h. (Run 1-Run 16, respectively, n=2, mean).

After storage at 40° C./75% r.h, capillary isoelectric focusing (cIEF) data showed increases in acidic species content at the expense of main peak content for all formulations. F4 formulations showed better chemical stability than F10 formulations with a lower decrease of the main peak relative content after one month storage at 40° C./75% r.h., as presented in FIG. 21. After one month storage at 40° C./75% r.h., F4 formulations showed a monomer peak loss in the range of 9.5-13.9%, while F10 formulations showed a monomer peak loss in the range of 14.7-17.3%.

Example 4—Stability

The results of the stability studies performed on 140 mg/mL isatuximab formulated in 110 mM Arginine-HCl, 9 mM Histidine, Sucrose 2%, Poloxamer-188 0.4%, pH 6.2 are provided.

Results

Stability at –20° C.±5° C.

As shown in Table 18, after storage at –20° C.±5° C. for 1 month, all the tested quality attributes (Visible particles, color, degree of opalescence, purity by SEC and cGE, protein concentration by UV, potency by ADCC and CDC bioassays, particulate matter by light obscuration and pH remained stable.

Charge heterogeneity by icIEF did not show any significant change compared to starting material.

Stability at +5° C.±3° C. (Long-Term Storage Condition)

As shown in Table 19 and Table 20, after storage at +5° C.±3° C. for 1, 3, 6, 9, and 12 months, all the tested quality attributes (visible particles, purity by SEC and cGE, protein concentration by UV, potency by CDC bioassay, particulate matter by light obscuration and pH remained stable for at least 12 months.

Color, degree of opalescence and charge heterogeneity by icIEF did not show any significant change compared to starting material for at least 12 months, compared to starting material.

Stability at +25° C.±2° C./60%±5% RH (Accelerated Storage Condition)

As shown in Table 21, after storage at +25° C.±2° C. for 6 months, all the tested quality attributes (visible particles, purity by SEC, protein concentration by UV, potency by ADCC and CDC bioassays, particulate matter by light obscuration and pH) remained stable for at least 6 months.

After 6 months at +25° C.±2° C., no changes were observed for both color and degree of opalescence.

After 6 months at +25° C.±2° C., a change in the charge heterogeneity profile by icIEF was observed as follows: a decrease in the main isoform content by 9% along with an increase in acidic isoforms by 9% was observed.

A slight decrease in the main peak (–2%) in the purity by cGE was observed correlated with an increase in sum of low molecular species (+2%).

A slight decrease in the monomer purity (–1.7%) by SEC was observed.

All other parameters did not show any significant change compared to starting material.

Stability at +40° C.±2° C./75%±5% RH (Stress Condition)

As shown in Table 22, under stress conditions, the following changes were observed after 1 month:

Change in charge heterogeneity profile by icIEF was observed as follows: decrease in main isoform content by 14%, mainly correlated with an increase in acidic forms by 15%.

A slight decrease in the main peak (–2%) in the purity by cGE was observed correlated with an increase in sum of low molecular species (+2%).

The percentage of aggregates by SEC remained constant.

CONCLUSION

The results from this stability study show that isatuximab—140 mg/mL formulated in 110 mM Arginine-HCl, 9 mM Histidine, Sucrose 2%, Poloxamer-188 0.4%, pH 6.2 remains stable at –20° C. for at least 1 month and at +5° C.±3° C. for at least 12 months.

TABLE 18

| Isatuximab 140 mg/mL-stability results at –20° C. ± 5° C. | | |
|---|---|---|
| Test | Initial Results | 1 month |
| Clarity and degree of opalescence | Not more than reference suspension | Not more than reference suspension |
| Color | Not more than degree 5 | Not more than degree 5 |
| Assay (UV) | | |
| Protein concentration (mg/mL) | 139.2 | 138.9 |
| pH | 6.3 | 6.3 |
| Purity (HPLC-SEC) | | |
| Monomer (area %) | 98.8 | 99.0% |
| Sum of HMW species (area %) | 1.0 | 0.8% |
| Charge heterogeneity (icIEF) | | |
| Main isoform (area %) | 74 | 71 |
| Sum of acidic isoforms (area %) | 18 | 21 |
| Sum of basic isoforms (area %) | 8 | 8 |
| Purity (cGE non reduced) | | |
| Main peak (area %) | 96 | 96 |
| Sum of LMW (area %) | 4 | 4 |
| Particulate matter (light obscuration) | | |
| Particles per container ≥25 μm | 0 | 0 |
| Particles per container ≥10 μm | 19 | 56 |
| Visible particles | Free from visible particulates | Free from visible particulates |
| ADCC Bioassay | | |
| Relative potency (% Ref Std EC$_{50}$/Sample EC$_{50}$) | 107 | 104 |
| CDC Bioassay | | |
| Relative potency (% Ref Std EC$_{50}$/Sample EC$_{50}$) | 105 | 111 |

TABLE 19

| isatuximab solution for injection 140 mg/mL-stability results at +5° C. ± 3° C. (T1M to T6M) | | | | |
|---|---|---|---|---|
| Test | Initial Results | 1 month | 3 months | 6 months |
| Clarity and degree of opalescence | Not more than reference suspension | Not more than reference suspension | Not more than reference suspension | Not more than reference suspension |
| Color | Not more than degree 5 | Not more than degree 5 | Not more than degree 5 | Not more than degree 5 |
| Assay (UV) | | | | |
| Protein concentration (mg/mL) | 139.2 | 140.4 | 139.8 | 139.8 |
| pH | 6.3 | 6.2 | 6.3 | 6.4 |

TABLE 19-continued

| isatuximab solution for injection 140 mg/mL-stability results at +5° C. ± 3° C. (T1M to T6M) | | | | |
|---|---|---|---|---|
| Test | Initial Results | 1 month | 3 months | 6 months |
| Purity (HPLC-SEC) | | | | |
| Monomer (area %) | 98.8 | 98.8 | 98.7 | 98.6 |
| Sum of HMW species (area %) | 1.0 | 0.9 | 0.9 | 1.0 |
| Charge heterogeneity (icIEF) | | | | |
| Main isoform (area %) | 74 | 72 | 70 | 73 |
| Sum of acidic isoforms (area %) | 18 | 21 | 22 | 19 |
| Sum of basic isoforms (area %) | 8 | 8 | 8 | 8 |
| Purity (cGE non reduced) | | | | |
| Main peak (area %) | 96 | 96 | 96 | 96 |
| Sum of LMW (area %) | 4 | 4 | 4 | 4 |
| Particulate matter (Light obscuration) | | | | |
| Particles per container ≥25 μm | 0 | 0 | 0 | 19 |
| Particles per container >10 μm | 19 | 243 | 187 | 206 |
| Visible particles | Free from visible particulates | Free from visible particulates | Free from visible particulates | Free from visible particulates |
| ADCC Bioassay | | | | |
| Relative potency (% Ref Std EC$_{50}$/Sample EC$_{50}$) | 107 | 103 | Not Determined | 91 |
| CDC Bioassay | | | | |
| Relative potency (% Ref Std EC$_{50}$/Sample EC$_{50}$) | 105 | 118 | 101 | 78 |

TABLE 20

| Isatuximab solution for injection 140 mg/mL-stability results at +5° C. ± 3° C. (T9M to T12M) | | | |
|---|---|---|---|
| Test | Initial Results | 9 months | 12 months |
| Clarity and degree of opalescence | Not more than reference suspension | Not more than reference suspension | Not more than reference suspension |
| Color | Not more than degree 5 | Not more than degree 5 | Not more than degree 5 |
| Assay (UV) | | | |
| Protein concentration | 139.2 | 141.9 | 140.2 |
| pH | 6.3 | 6.2 | 6.2 |
| Purity (HPLC-SEC) | | | |
| Monomer (area %) | 98.8 | 98.5 | 98.5 |
| Sum of HMW species (area %) | 1.0 | 1.1 | 1.1 |
| Charge heterogeneity (icIEF) | | | |
| Main isoform (area %) | 74 | 73 | 73 |
| Sum of acidic isoforms (area %) | 18 | 19 | 20 |
| Sum of basic isoforms (area %) | 8 | 8 | 8 |
| Purity (cGE non reduced) | | | |
| Main peak (area %) | 96 | 95 | 95 |
| Sum of LMW (area %) | 4 | 5 | 5 |
| Particulate matter (Light | | | |

TABLE 20-continued

Isatuximab solution for injection 140 mg/mL-stability
results at +5° C. ± 3° C. (T9M to T12M)

| Test | Initial Results | 9 months | 12 months |
|---|---|---|---|
| obscuration) | | | |
| Particles per container ≥25 μm | 0 | 56 | 0 |
| Particles per container ≥10 μm | 19 | 747 | 691 |
| Visible particles | Free from visible particulates | Free from visible particulates | Free from visible particulates |
| ADCC Bioassay | | | |
| Relative potency (% Ref Std EC$_{50}$/Sample EC$_{50}$) | 107 | Not determined | 95 |
| CDC Bioassay | | | |
| Relative potency (% Ref Std EC$_{50}$/Sample EC$_{50}$) | 105 | 97 | 93 |

TABLE 21

Isatuximab solution for injection, 140 mg/mL-stability results at
+25° C. ± 2° C./60% ± 5% RH

| Test | Initial Results | 1 month | 3 months | 6 months |
|---|---|---|---|---|
| Clarity and degree of opalescence | Not more than reference suspension | Not more than reference suspension | Not more than reference suspension | Not more than reference suspension |
| Color | Not more than degree 5 | Not more than degree 5 | Not more than degree 5 | Not more than degree 5 |
| Assay (UV) | | | | |
| Protein concentration | 139.2 | 138.2 | 140.7 | 140.5 |
| pH | 6.3 | 6.3 | 6.3 | 6.3 |
| Purity (HPLC-SEC) | | | | |
| Monomer (area %) | 98.8 | 98.7 | 97.9 | 97.1 |
| Sum of HMW species (area %) | 1.0 | 0.9 | 1.1 | 1.3 |
| Charge heterogeneity (icIEF) | | | | |
| Main isoform (area %) | 74 | 71 | 66 | 65 |
| Sum of acidic isoforms (area %) | 18 | 21 | 26 | 27 |
| Sum of basic isoforms (area %) | 8 | 8 | 8 | 8 |
| Purity (cGE non reduced) | | | | |
| Main peak (area %) | 96 | 96 | 95 | 94 |
| Sum of LMW (area %) | 4 | 4 | 5 | 6 |
| Particulate matter (Light obscuration) | | | | |
| Particles per container ≥25 μm | 0 | 19 | 56 | 0 |
| Particles per container ≥10 μm | 19 | 280 | 1158 | 1400 |
| Visible particles | Free from visible particulates | Free from visible particulates | Free from visible particulates | Free from visible particulates |
| ADCC Bioassay | | | | |
| Relative potency (% Ref Std EC$_{50}$/ Sample EC$_{50}$) | 107 | 107 | Not determined | 83 |
| CDC Bioassay | | | | |
| Relative potency (% Ref Std EC$_{50}$/Sample EC$_{50}$) | 105 | 105 | 95 | 85 |

TABLE 22

Isatuximab solution for injection, 140 mg/mL-stability results at +40° C. ± 2° C./75% ± 5% RH

| Test | Initial Results | 15 days | 1 month |
|---|---|---|---|
| Clarity and degree of opalescence | Not more than reference suspension III | Not more than reference suspension III | Not more than reference suspension IV |
| Color | Not more than degree 5 | Not more than degree 5 | Not more than degree 5 |
| Assay (UV) | | | |
| Protein concentration | 139.2 | 139.2 | 138.4 |
| pH | 6.3 | 6.3 | 6.3 |
| Purity (HPLC-SEC) | | | |
| Monomer (area %) | 98.8 | 97.9 | 97.2 |
| Sum of HMW species (area %) | 1.0 | 1.1 | 1.1 |
| Charge heterogeneity (icIEF) | | | |
| Main isoform (area %) | 74 | 68 | 60 |
| Sum of acidic isoforms (area %) | 18 | 25 | 33 |
| Sum of basic isoforms (area %) | 8 | 8 | 7 |
| Purity (cGE non reduced) | | | |
| Main peak (area %) | 96 | 95 | 94 |
| Sum of LMW (area %) | 4 | 5 | 6 |
| Particulate matter (Light obscuration) | | | |
| Particles per container ≥25 μm | 0 | 0 | 0 |
| Particles per container ≥10 μm | 19 | 150 | 56 |
| Visible particles | Free from visible particulates | Free from visible particulates | Free from visible particulates |
| ADCC Bioassay | | | |
| Relative potency (% Ref Std EC$_{50}$/Sample EC$_{50}$) | 107 | 100 | 103 |
| CDC Bioassay | | | |
| Relative potency (% Ref Std EC$_{50}$/Sample EC$_{50}$) | 105 | 104 | 97 |

Example 5—In Vivo Study in Minipigs

This example describes a study in which minipigs were treated with formulations of isatuximab administered by subcutaneous injection. The minipig was selected as the test model for this study of subcutaneous local tolerance because of its well accepted suitability and since it is commonly used for non-clinical assessment of the intended human route of administration.

Four formulations (F1, F2, F4 and F10) and a saline solution (0.9% sodium chloride) as negative control were tested on 8 minipigs (1-year-old female, 20-25 kg) with 4 animals per testing group. Each animal received injections of 2 formulations and a negative control, with 3 weeks for recovery between each injection. Administration was performed on the flank region via a catheter fitted with a butterfly 27 G needle using a syringe pump (Harvard Apparatus Model '22') equipped of a back pressure captor (RSBS Subminiature Load Cell 50LB/200N) for tissue back pressure monitoring.

During infusion, the animals were observed with focus on general behavior, vocalization, and visual parameters for pain assessment. Infusion syringe pressure and evidence of leakage were monitored as well. The injection sites were observed for skin changes and plasma analysis for Substance P and cortisol were performed. Skin biopsy was collected on 5th day in 10% NBF.

Pain symptoms were recorded during and after the injection for 5 days. Pain markers were dosed in the blood sampled along the injection and for the following 90 minutes. A histopathology study was then conducted on a skin sample taken at the point of injection. In terms of histopathology, all formulations were well tolerated.

All solutions of isatuximab were prepared from the same pre-formulated batch of isatuximab solution. This batch had been formulated at 30 mg/mL, pH 6 in histidine 20 mM and sucrose 5%.

All the formulations tested for the research minipig study are described in Table 23.

TABLE 23 minipig formulations

| | Conc. (mg/mL) | Histidine (mM) | Lys-Cl (mM) | Arg-Cl (mM) | Lys-Ac (mM) | Sucrose % (p/v) | PS 80 % (p/v) | P188 % (p/v) | pH |
|---|---|---|---|---|---|---|---|---|---|
| F1 | 150 | 10* | 125* | — | — | 2 | 0.04 | — | 6.2 |
| F2 | 135 | 10* | — | 125* | — | 2 | 0.04 | — | 6.2 |
| F4 | 140 | 10** | — | 125** | — | 2 | — | 0.4 | 6.2 |
| F10 | 140 | — | — | — | 125** | 2 | 0.04 | — | 6.2 |

*nominal values of diafiltration buffer and CES, not taking into account shift caused by Donnan effect during ultrafiltration

**nominal values diafiltration buffer and CES, not taking into account shift caused by Donnan effect during ultrafiltration but later quantified in F4 and F10

For the preparation of each formulation, the buffer (without sucrose and surfactant) was exchanged by diafiltration, and the antibody was concentrated to a higher value than the target formulation. After a first adjustment of concentration, a concentrated excipient solution, (concentrated sucrose and surfactant dissolved in diafiltration buffer) was added to obtain the final formulations.

Studied diafiltration buffers are presented in Table 24.

TABLE 24

Composition of diafiltration buffers

| | Histidine (mM) | Histidine, HCl (mM) | Lysine-Cl (mM) | Arginine, Cl (mM) | Lysine-Ac (mM) | Acetic acid | pH |
|---|---|---|---|---|---|---|---|
| F1 | 6.2 | 3.8 | 125 | — | — | — | 6.3 |
| F2 & F4 | 5.2 | 4.8 | — | 125 | — | — | 6.1 |
| F10 | — | — | — | — | 125 | 3.7 | 6.2 |

The values recorded of the final formulation are shown in Table 25.

TABLE 25

| | Target concentration (mg/mL) | Concentration (mg/mL) | Osmolality (mOsm/kg) | Osmolality (sample dilute) | Density | pH** | [His] (mM) | [Arg] (mM) | [Lys] (mM) |
|---|---|---|---|---|---|---|---|---|---|
| | | | | Analytical results | | | | | |
| F1 | 150 | 149.6 | 364 | 298 | 1.058* | 6.3 | n.a. | — | n.a. |
| F2 | 135 | 137.5 | 336 | 288 | 1.056 | 6.3 | n.a. | n.a. | — |
| F4 | 140 | 141.8 | 352 | 297 | 1.057 | 6.3 | 9 | 105 | — |
| F10 | 140 | 142.5 | 369 | 289 | 1.055 | 6.2 | — | — | 99 |

*density of formulation before filtration
**pH measured after filtration, with a microelectrode
n.a. = not available (not measured)

A total of eight 1-year-old female minipigs were used in the study. Each formulation was tested on 4 animals, who each received a volume of 18 mL in 30 minutes (0.6 mL/min). The study lasted 5 days, during which pain markers and symptoms were recorded. At the end of the 5 days, an 8 mm disk of skin was sampled (biopsy) for histopathology.

Formulations F2 and F4 were first tested on the minipigs. After a lag time of 21 days, formulations F1 and F10 were then tested on the same 8 minipigs. Finally, after a second lag time, a saline solution was tested on the same 8 minipigs.

For each formulation/saline solution, the study was conducted as follows:

Injection of the solution to the 4 minipigs (8 for saline solution)

During infusion: live record of following parameters:
Telemetric measurements (ECG)
Syringe back pressure (for calculation of tissue back pressure)
Pain markers (cortisol, Substance P, dosed in blood—required regular blood sampling)
Pain symptoms (scratching, scrubbing, noise, redness), and size of edema from infusion.

After infusion:
Pain markers in the 90 minutes following the end of the infusion
Pain symptoms (scratching, scrubbing, redness) for 5 days (visual inspection, arbitrary units)
Histopathology on sample tissues (skin biopsy after 5 days)

The main results on pain are summarized in Table 26.

TABLE 26

| | Plasma cortisol in nmol/L (max of average on 4 minipig)* | Pain symptoms during infusion (per minipig) |
|---|---|---|
| | | Pain markers and pain symptoms |
| F1 | 145 | 0.25 |
| F2 | 235 | 1.5 |
| F4 | 195 | 1 |
| F10 | 340 | 2.25 |
| control | n.r.** | 20 |

*strong variation between animals for the same formulation
**n.r.= not reported

In Table 26, only plasma cortisol was reported as a pain marker. Levels of Substance P, measured for all formulations, did not change over time. An increase of plasma cortisol was recorded after injection. The maximum of the average value calculated on the 4 minipigs for each formulation is reported in Table 26. The maximum value of that average was obtained for F10. For all formulations, there were variations of the level of plasma cortisol between the 4 test animals.

Figure 22:
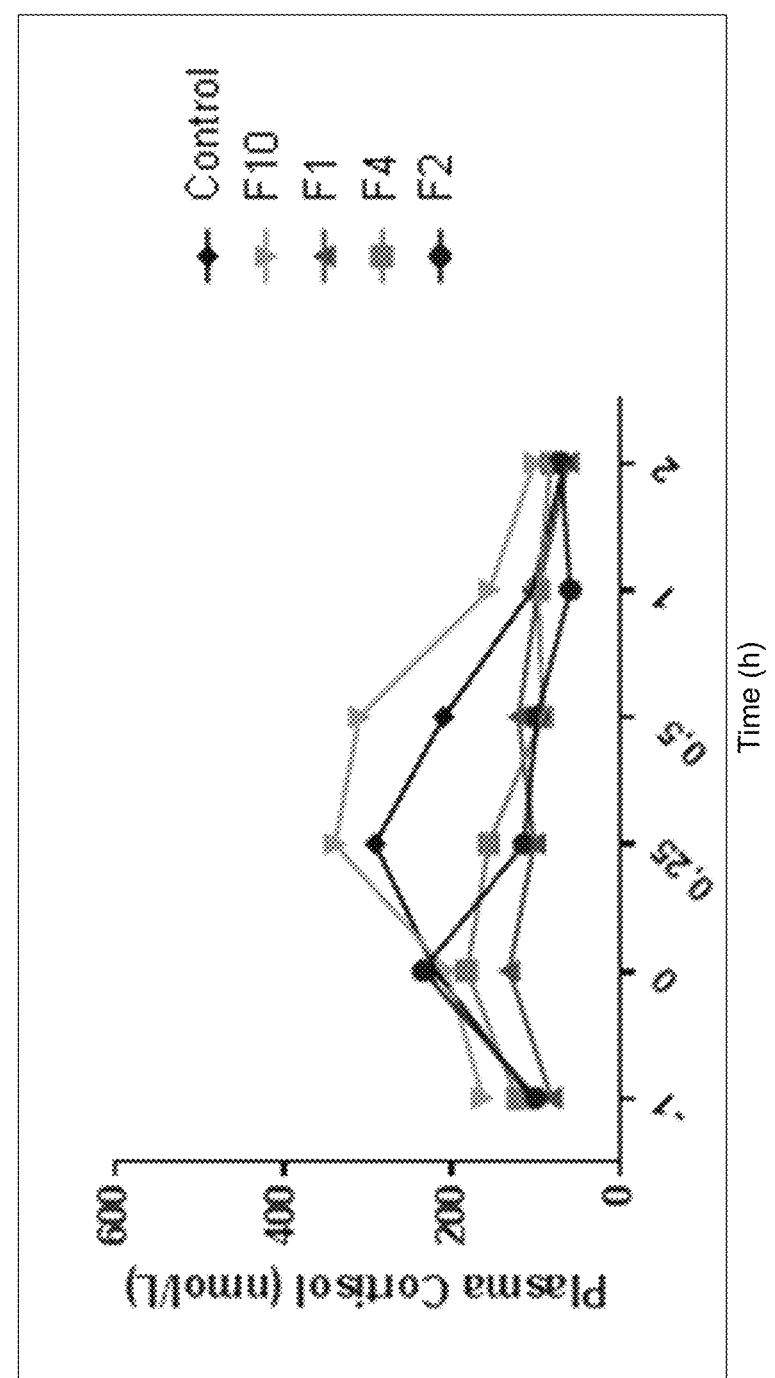
FIG. 22 is a graph depicting plasma cortisol in minipigs infused subcutaneously with indicated formulations of isatuximab or NaCl control as described in Example 5.
Figure 23:
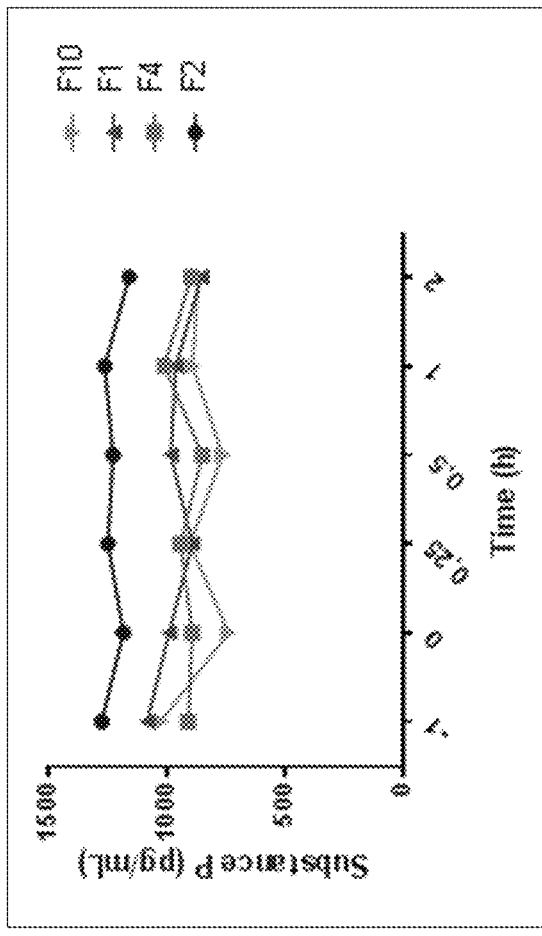
FIG. 23 is a graph depicting plasma Substance P in minipigs infused subcutaneously with indicated formulations of isatuximab or NaCl control as described in Example 5.
Figure 24:
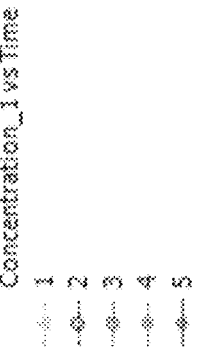
FIG. 24 is a graph depicting serum concentration of isatuximab over time in individual minipigs 1 to 5 in Group I as described in Example 6.
Figure 24:
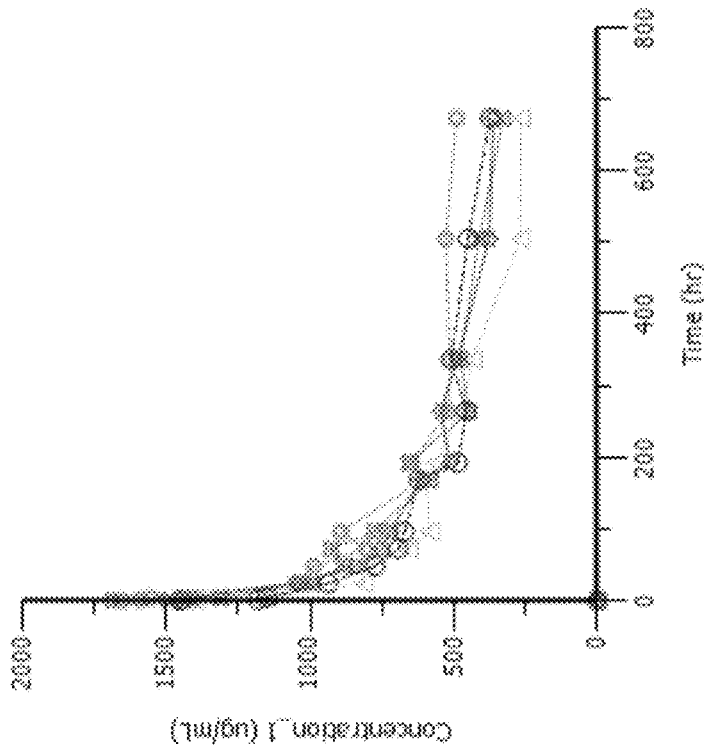
Figure 25:
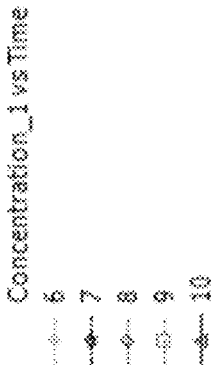
FIG. 25 is a graph depicting serum concentration of isatuximab over time in individual minipigs 6 to 10 in Group II as described in Example 6.
Figure 25:
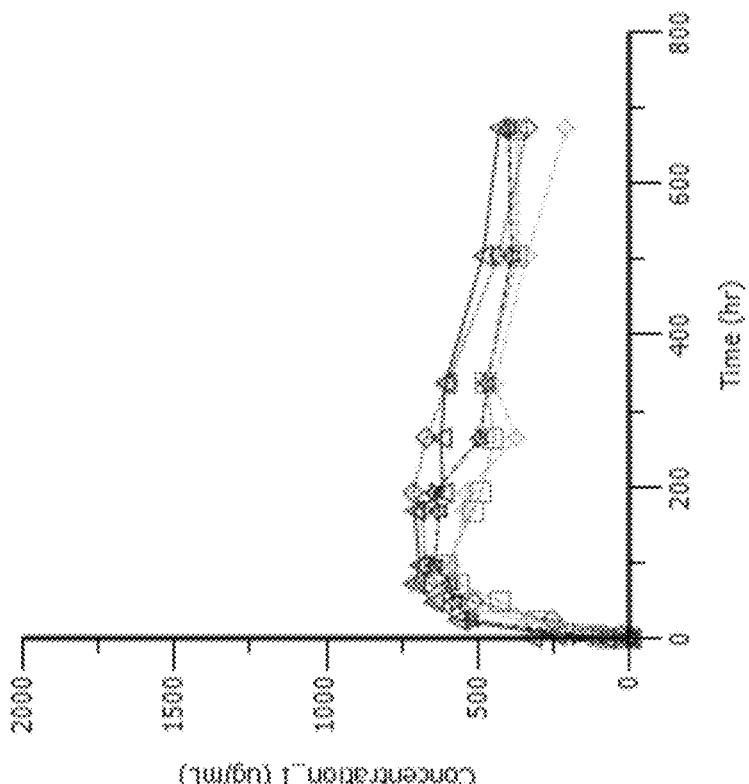
Figure 26:
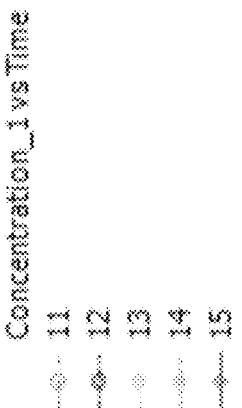
FIG. 26 is a graph depicting serum concentration of isatuximab over time in individual minipigs 11 to 15 in Group III as described in Example 6.
Figure 26:
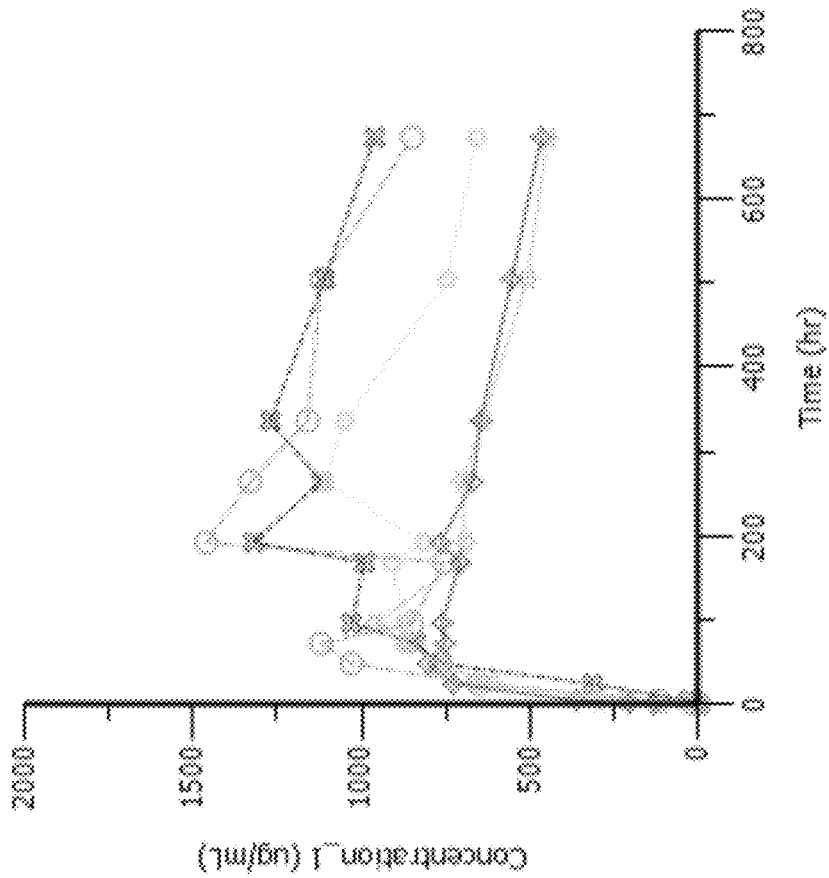
Figure 27:
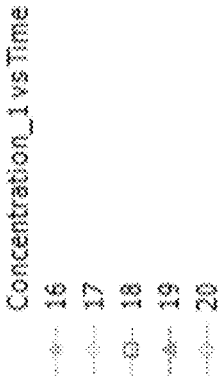
FIG. 27 is a graph depicting serum concentration of isatuximab over time in individual minipigs 16 to 20 in Group IV as described in Example 6.
Figure 27:
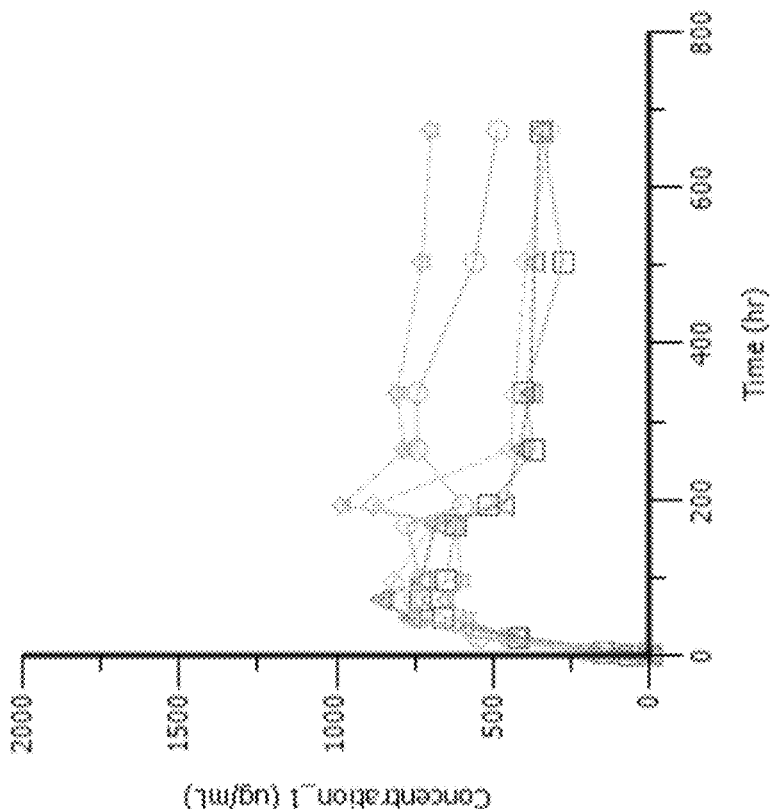

The number of pain symptoms for F10 was also the highest of the 4 formulations and had the highest plasma cortisol levels (FIG. 22). F2 had the second highest number of pain symptoms and had the highest Substance P levels (FIG. 23). Not shown in Table 26 was the finding that both F1 and F2 had poor antibody stability.

No leakage and nearly constant syringe back pressure were observed during the injection with the 4 formulations.

The main results on histopathology are summarized in Table 27.

TABLE 27

| Treatment Group | Dermis Minimal perivascular inflammation | Subcutaneous tissue Minimal to moderately increased collagen | Skeletal muscle Focal myofiber necrosis, reparative granulation tissue |
|---|---|---|---|
| | | Histopathology results | |
| F1 | 4/4 (100%) | 3/4 (75%) | 1/4 (25%) |
| F2 | 4/4 (100%) | 2/4 (50%) | 4/4 (100%) |
| F4 | 4/4 (100%) | 3/4 (75%) | 1/4 (25%) |
| F10 | 4/4 (100%) | 3/4 (75%) | 0/4 (0%) |
| Saline | 4/4 (100%) | 1/4 (25%) | 1/4 (25%) |

Dermis and subcutaneous tissue did not show meaningful differences between the formulations. Formulation F2 showed higher incidence (100%) of skeletal muscle changes compared to formulation F1 (25%), F4 (25%), F10 (0%), or saline (25%).

Example 6—Second In Vivo Study in Minipigs

The objective of the study described in this example was to assess the local tolerance and plasma pharmacokinetics of isatuximab following single administration by subcutaneous infusion to minipigs using three different flow rates. Further, one group of animals was dosed once intravenously to evaluate the bioavailability of isatuximab following the different subcutaneous infusions.

The test samples, isatuximab 500 mg/25 mL (20 mg/mL) for IV infusion, and isatuximab 140 mg/mL (Formulation F4 in Example 5), for SC infusion, were used. Saline (0.9% NaCl) for injection was used as negative control item for Groups 2, 3 and 4.

The study was performed in 20 female Gottingen SPF (Specific Pathogen Free) minipigs from Ellegaard Göttingen Minipigs A/S, DK-4261 Dalmose, Denmark. The animals were ordered with a body weight of 20-25 kg at arrival. A pre-treatment period of 15 days (including an acclimatization period of 5 days) was allowed, during which the animals were observed daily in order to reject any animals in poor condition. All observations were recorded.

The animals were randomized into four treatment groups as shown in Table 28:

TABLE 28

| | Treatment groups | | | | | |
|---|---|---|---|---|---|---|
| | Sample and concentration (mg/mL) | | Dose Route (infusion | Dose Volume | Isatuximab Dose | Animal |
| Group | Day 1 | Day 8 | rate) | (mL) | (mg/animal) | Nos |
| 1 | isatuximab (20) | — | IV (3 mL/min) | 90 | 1800 | 1-5 |
| 2 | isatuximab (140) | saline | SC (0.5 mL/min) | 12.9 | 1806 | 6-10 |
| 3 | isatuximab (140) | saline | SC (1 mL/min) | 12.9 | 1806 | 11-15 |
| 4 | isatuximab (140) | saline | SC (2 mL/min) | 12.9 | 1806 | 16-20 |

For intravenous infusion, 9 days before start of treatment, ear vein catheters were implanted in 6 animals (5+1 spare). Five of these animals were allocated to Group 1 (IV infusion group); the last animal was included in one of the subcutaneous groups.

All administrations were performed using a Baxter Colleague CXE volumetric infusion pump. The Baxter Colleague CXE pump is capable of infusing from semi-rigid containers, rigid containers, flexible IV bags, and vented syringes. The test and negative control items were placed in sterile glass infusion bottles during the administrations.

The first day of treatment was designated Day 1.

On Day 1, Group 1, a single dose of isatuximab (1800 mg/animal) was given by 30-minute infusion through the implanted ear vein catheter, at a flow rate of 3 mL/min.

On Day 1, Groups 2, 3 and 4, a single dose of isatuximab (1806 mg/animal) was given through a subcutaneous catheter with butterfly needle, at a flow rate of 0.5, 1 and 2 mL/min, respectively. The butterfly needle was placed in the left lower flanks area just in front of the knee area.

On Day 8, Groups 2, 3 and 4, a single dose of saline (negative control) was given through a subcutaneous catheter with butterfly needle, at a flow rate of 0.5, 1 and 2 mL/min, respectively. The butterfly needle was placed in the right lower flanks area just in front of the knee area.

Dose volume was 90 mL for Group 1 and 12.9 mL for Groups 2-4.

The subcutaneous injection sites in Groups 2-4 was observed for leakage during the infusions.

The subcutaneous injection sites were marked along the edge of the local swelling that develops during the infusion procedure, and re-marked as necessary.

Needle size for SC infusion was 23 G.

All signs of ill health and any behavioral changes were recorded daily. Any deviation from normal was recorded. During dosing, the animals were observed for general behavior and any vocalization, with emphasis on any signs of stress, discomfort or pain.

For Groups 2-4, the subcutaneous injection sites were observed daily from the day of dosing, for hemorrhage, erythema, swelling (bleb formation, with indication of size)

and firmness, but not excluding other signs. On days of dosing, the injection sites were observed before infusion, and at end of the infusions, and then at 15 min (±2 min), 30 min (±2 min), 1 (±3 min), 2 (±6 min), and 4 hours (±12 min) after end of dosing. Thereafter, the injection sites were observed daily until Day 17, as no local reactions were observed from Day 10. The parameters were scored according to the following grading system: 0—not present; 1—minimal; 2—slight; 3—moderate; and 4—marked.

Blood Samples for Pharmacokinetics

Starting on Day 1, blood samples were taken from all animals. Blood sampling was performed at the following time points: pre-treatment, within 2 minutes after the end of infusion, and at 1 (±3 min), 4 (±12 min), 24 (±1 hour 12 min), 48 (±2 hours 24 min), 72, 96, 168, 192, 264, 336, 504 and 672 hours post end of infusion (tolerance of ±3 hours from 72 hours).

Pharmacokinetic (PK) analysis were performed using the software Phoenix WinNonlin Version 6.3 by Pharsight Corporation, Mountain View, CA, USA. A noncompartmental analysis using WinNonlin plasma model (intravenous infusion and extravascular dose model) was performed as appropriate.

The plasma concentration-time data from each individual animal was used for pharmacokinetic calculations. In addition to parameter estimates for individual animals, descriptive statistics (e.g., mean, standard deviation, and coefficient of variation) were reported, as appropriate. All parameters for each animal were generated from individual test article concentrations in plasma following treatments on Day 1. For determination of individual pharmacokinetic parameters, concentrations below the limit of quantitation were treated as zero. For determination of mean concentrations, samples below the limit of quantitation were treated as zero.

Parameters were estimated using nominal dose levels. Parameters were estimated using nominal sampling times as no time deviations more than 15% from nominal were documented. Predose concentrations on Day 1 were set equal to zero.

Descriptive statistics (mean, standard deviation, as applicable) and pharmacokinetic parameters were reported to three significant figures. Coefficient of variation was reported without decimal place.

The following PK parameters were estimated for isatuximab:

$C_{max}$—observed maximum concentration, $t_{max}$—time of maximum concentration, $C_{last}$—the last measurable concentration, $t_{last}$—the time of the last measurable concentration, $AUC_{0-24\ h}$—area under the plasma concentration-time curve from 0 to 24 hours were calculated by noncompartmental analysis using the linear trapezoidal rule, $AUC_{0-72\ h}$—area under the plasma concentration-time curve from 0 to 72 hours were calculated by noncompartmental analysis using the linear trapezoidal rule, $AUC_{0-168\ h}$—area under the plasma concentration-time curve from 0 to 168 hours were calculated by noncompartmental analysis using the linear trapezoidal rule, $AUC_{0-t}$—area under the plasma concentration-time curve calculated from 0–t, where t was the time of the last measurable concentration, was calculated by noncompartmental analysis using the linear trapezoidal rule, Bioavailability of the SC infusions relative to IV infusions were evaluated, using $AUC_{0-24 \ h}$, $AUC_{0-72 \ h}$, $AUC_{0-168 \ h}$, and $AUC_{0-t}$.

Additional parameters (i.e. $t_{1/2z}$, $V_z$, CL) were calculated for IV route.

Collection of Skin Biopsies from SC Injection Sites (Groups 2 to 4)

On both Day 8 and Day 29, three skin biopsies, approximately 7-10 mm in depth, for histopathology were taken from the left subcutaneous infusion site (test item site) of all animals in Groups 2 to 4, using a 6 mm biopsy punch. The collection on Day 8 was performed after dosing with saline (negative control) in order to be able to monitor the animals during the infusions.

The biopsies collected on Day 8 (biopsy Nos 1-3) were taken from the cranial half of the infusion area. Biopsy No 1 was collected from the dorsal area, biopsy No 2 from the mid area, and biopsy No 3 from the ventral part. The biopsies collected on Day 29 were collected from the caudal half of the infusion area in a similar way. Furthermore, an untreated control (biopsy No 4) from outside the dosed area was collected from the same region of all animals on both days.

On both Day 15 and 36, skin biopsies were collected in a similar way from the right subcutaneous infusion site (saline site) of all animals in Groups 2 to 4.

The biopsies collected on Day 15 (biopsy Nos 5-7) were taken from the cranial half of the infusion area. Biopsy No 5 was collected from the dorsal area, biopsy No 6 from the mid area, and biopsy No 7 from the ventral part. The biopsies collected on Day 36 were collected from the caudal half of the infusion area in a similar way. Furthermore, an untreated control (biopsy No 8) from outside the dosed area was collected from the same region of all animals on both days.

Each biopsy from each animal was placed in a separate container and fixed in phosphate buffered neutral 4% formaldehyde.

Results

No test sample-related clinical signs were observed in any of the animals.

In three animals (No 4, Group 1, and No 6 and 7, Group 2) the skin appeared to be warm to the touch on Day 1 and Day 2. However, as the number of animals affected was low, this was considered to be an incidental finding.

In all groups, local reactions at the infusion sites were scored on the day of infusion. No scores were obtained on the other days.

In Group 2 (0.5 mL/min) on Day 1 (isatuximab), slight erythema was primarily noted among all animals at the infusion site, and minimal to moderate swelling (bleb formation) was observed in three animals, within the first two hours after the end of infusion. Furthermore, three animals had minimal hemorrhage within the first 15 minutes after the end of infusion.

On Day 8 (saline at 0.5 mL/min) for Group 2, minimal erythema was primarily noted among all animals at the infusion site, and minimal to moderate swelling (bleb formation) was observed in two animals, within the first two hours after the end of infusion. Further, minimal hemorrhage was observed in three animals after the end of infusion.

In Group 3 (1 mL/min) on Day 1 (isatuximab), minimal to slight erythema was observed among four animals at the infusion site within the first 4 hours after the end of infusion, and minimal to marked swelling (bleb formation) was seen in three animals, reducing in size by 4 hours after the end of infusion. Minimal hemorrhage, and slight hemorrhage in one animal, was observed within the first 30 minutes after the end of infusion in three animals.

On Day 8 (saline at 1 mL/min) for Group 3, minimal to slight erythema was observed among all animals at the infusion site within the first 4 hours after the end of infusion, and one animal had minimal to moderate swelling (bleb formation) from post dosing, reducing in size by 2 hours after the end of infusion. Minimal hemorrhage, and slight hemorrhage in one animal, was observed within the first 15 minutes after the end of infusion in all animals.

In Group 4 (2 mL/min) on Day 1 (isatuximab), minimal to slight erythema (moderate in one animal) was observed among four animals at the infusion site within the first 2 hours after the end of infusion, and up to marked swelling (bleb formation) was seen among the animals from post dosing, reducing in size by 4 hours after the end of infusion. Two animals showed minimal hemorrhage at the end of infusion.

On Day 8 (saline at 2 mL/min) for Group 4, minimal erythema (slight in two instances) was primarily observed among all animals at the infusion site within the first 30 minutes after the end of infusion, and up to moderate swelling (bleb formation) was seen in two animals from post dosing, reducing in size by 1 hour after the end of infusion. Minimal hemorrhage was observed in two animals at the end of infusion.

No signs of leakage were observed during the infusions.

TABLE 29

| Summary of local reaction findings at SC infusion sites | | | | |
|---|---|---|---|---|
| Infusion speed (mL/min) | Test item | Erythema Incidence (Severity range) | Hemorrhage Incidence (Severity range) | Swelling Incidence (Severity range) [Maximal size] |
| 0.5 | isatuximab | 5/5 (minimal-moderate) | 3/5 (minimal) | 3/5 (minimal-moderate) [50 × 35 × 10 mm] |
| | 0.9% NaCl | 5/5 (minimal-slight) | 3/5 (minimal) | 2/5 (minimal-moderate) [45 × 45 × 10 mm] |
| 1 | isatuximab | 4/5 (minimal-slight) | 3/5 (minimal-slight) | 3/5 (minimal-marked) [50 × 40 × 8 mm] |
| | 0.9% NaCl | 5/5 (minimal-slight) | 5/5 (minimal-slight) | 1/5 (moderate) [35 × 35 × 12 mm] |
| 2 | isatuximab | 4/5 (minimal-moderate) | 2/5 (minimal) | 4/5 (minimal-marked) [55 × 40 × 10 mm] |
| | 0.9% NaCl | 5/5 (minimal-slight) | 2/5 (minimal) | 2/5 (minimal-moderate) [25 × 25 × 8 mm] |

Pharmacokinetics

Individual plasma concentrations of isatuximab over time are shown in FIGS. 24-27.

Non-compartmental pharmacokinetic analysis of the plasma level data was performed using Phoenix WinNonlin Version 6.3 pharmacokinetic software.

TABLE 30

Mean (CV %, n = 5) pharmacokinetic parameters of isatuximab in minipig
plasma following a single intravenous (IV) or subcutaneous (SC) infusion

| Route Rate (mL/min) | $T_{max}$ (hr) | $C_{max}$ (μg/mL) | $T_{last}$ (hr) | $C_{last}$ (μg/mL) | $AUC_{last}$ (h * μg/mL) | $AUC_{0-24}$ (h * μg/mL) | $AUC_{0-72}$ (h * μg/mL) | $AUC_{0-168}$ (h * μg/mL) | $F^1$ |
|---|---|---|---|---|---|---|---|---|---|
| IV 3 | End[3] (0) | 1,540 (8) | 672[3] (0) | 366 (22) | 364,000 (11) | 28,400 (11) | 69,800 (10) | 136,000 (10) | — |
| SC 0.5 | 96 [72-192][2] (50) | 678 (8) | 672[3] (0) | 349 (24) | 325,000 (13) | 5,450 (48) | 31,500 (20) | 92,200 (11) | 0.89 |
| SC 1 | 192 [48-264][2] (54) | 1130 (23) | 672[3] (0) | 677 (34) | 565,000 (25) | 8,330 (37) | 45,900 (14) | 129,000 (5) | 1.55[4] |
| SC 2 | 168 [72-192][2] (45) | 847 (12) | 672[3] (0) | 440 (36) | 369,000 (23) | 6,610 (19) | 38,500 (10) | 106,000 (10) | 1.01 |

End = End of infusion
[1] calculated using $AUC_{last}$
[2] median [min-max]
[3] same value for median, min and max
[4] high F value related to higher variability noted for this group; the contribution of 2/5 animals which showed an apparent higher exposure Isatuximab was quantifiable in all plasma samples in the study collected from the end of the infusion onwards, with the exception of a single sample taken at the end of the SC infusion for a Group 4 female and at 1 hour post SC infusion for a Group 3 female, which were below the lower limit of quantification (LLOQ). Concentrations in all predose samples were below the LLOQ. Profiles were consistent with extravascular and intravenous dosing, for the SC and IV routes, respectively. Overall, the variability observed in the PK parameters was low for the IV infusion, and low to moderate for the SC infusion.

Following a single IV infusion of isatuximab at 1800 mg/animal over a 30-minute period to minipigs, the maximal plasma levels were all observed at the end of the infusion period in all animals. Following a single SC infusion of isatuximab at 1806 mg/animal to minipigs under a flow rate of 0.5, 1 or 2 mL/min, the median maximal plasma levels were observed at 96, 192 and 168 hours after the end of the infusions, respectively. However, individual $T_{max}$ values ranged from 48 to 264 hours and showed no relationship to SC infusion rate.

Following a single IV infusion of isatuximab at 1800 mg/animal over a 30-minute period to minipigs, the mean AUC over the complete 672-hour post dose sampling period ($AUC_{last}$) was 364,000 hr*μg/mL. Following a single SC infusion of isatuximab at 1806 mg/animal to minipigs under a flow rate of 0.5, 1 or 2 mL/min, the mean AUC over the complete 672-hour post dose sampling period ($AUC_{last}$) was 326,000, 565,000 and 369,000 hr*μg/mL, respectively. $AUC_{last}$ values were globally similar for each SC group, suggesting no impact of the infusion rate on exposure.

Under the conditions of this study, the absolute SC bioavailability for isatuximab, when given by SC infusion to minipigs at flow rates of 0.5, 1 or 2 mL/min, was broadly similar for the 3 flow rates tested at each of the AUC intervals considered. Bioavailability increased with increasing AUC interval, reaching F values of 0.89, 1.55 and 1.01 for the 0.5, 1 and 2 mL/min flow rates, respectively, when calculated using the AUC for the complete 672-hour post dose sampling period ($AUC_{last}$). For the group infused at 1 mL/min, the high F value estimated was related to the higher variability noted for this group; the contribution of 2/5 animals which showed an apparent higher exposure.

Overall, it was concluded that the absolute SC bioavailability of isatuximab in minipigs when given at a dose of 1806 mg/animal (solution of 140 mg/mL) by SC infusion at flow rates of 0.5 to 2 mL/min was at least 89%.

Microscopic Examination of Skin Biopsies

At the microscopic examination of the injection site skin biopsies, no treatment-related changes were observed for any subcutaneous group. The microscopic findings were mainly minimal focal infiltration of mononuclear cells and minimal focal epidermal crusts with no difference in incidence and morphology of the findings between the subcutaneous dose groups. Likewise, the findings were considered similar when comparing the saline (negative control) treated injection sites to the test sample treated injection sites within a dose group (same infusion speed). All microscopic findings were considered well-known incidental background changes in the skin of Gottingen minipigs.

Discussion

Isatuximab, when given by intravenous infusion (as solution of 20 mg/mL) at a dose of 1800 mg/animal and under a flow rate 3 mL/min, or as subcutaneous infusion (as solution of 140 mg/mL in formulation F4 of Example 5) at a dose of 1806 mg/animal and under a flow rate of 0.5, 1 or 2 mL/min, were both clinically and histopathologically very well tolerated when given to female Gottingen minipigs.

Local reactions at the subcutaneous injection sites of all groups were only observed on the day of infusion at the sites.

The incidence and severity scores for erythema and hemorrhage were comparable for the three subcutaneous flow rates tested (0.5, 1 and 2 mL/min), and similar for both isatuximab and saline negative control. However, swelling (bleb formation) at the infusion site was more pronounced for isatuximab infused at 1 mL/min and 2 mL/min as compared to 0.5 mL/min. This was most probably a physical phenomenon, related to the large volume injected at a single site, with the severity being inversely related to infusion time, at constant removal rate of fluid from the infusion site. Furthermore, swelling was more marked after infusion with isatuximab than after infusion with saline. Swelling after infusion with saline was comparable at all 3 flow rates.

At the microscopic examination of the injection site skin biopsies, no treatment-related changes were observed for any subcutaneous group.

Following a single IV infusion of isatuximab at 1800 mg/animal over a 30-minute period to minipigs, the maximal plasma levels were all observed at the end of the infusion period in all animals. Following a single SC infusion of isatuximab at 1806 mg/animal to minipigs under a flow rate of 0.5, 1 or 2 mL/min, the median maximal plasma levels were observed at 96, 192 and 168 hours after the end of the infusions, respectively. However, individual $T_{max}$ values ranged from 48 to 264 hours and showed no relationship to SC infusion rate.

Following a single IV infusion of isatuximab at 1800 mg/animal over a 30-minute period to minipigs, the mean AUC over the complete 672-hour post dose sampling period ($AUC_{last}$) was 364,000 hr*μg/mL. Following a single SC infusion of isatuximab at 1806 mg/animal to minipigs under a flow rate of 0.5, 1 or 2 mL/min, the mean AUC over the complete 672-hour post dose sampling period ($AUC_{last}$) was 326,000, 565,000 and 369,000 hr*μg/mL, respectively. $AUC_{last}$ values were globally similar for each SC group, suggesting no impact of the infusion rate on exposure.

Under the conditions of this study, the absolute SC bioavailability for isatuximab formulated in F4 of Example 4, when given by SC infusion to minipigs at flow rates of 0.5, 1 or 2 mL/min, was broadly similar for the 3 flow rates tested at each of the AUC intervals considered. Bioavailability increased with increasing AUC interval, reaching F values of 0.89, 1.55 and 1.01 for the 0.5, 1 and 2 mL/min flow rates, respectively, when calculated using the AUC for the complete 672-hour post dose sampling period ($AUC_{last}$). For the group infused at 1 mL/min, the high F value estimated was related to the higher variability noted for this group; the contribution of 2/5 animals which showed an apparent higher exposure.

Example 7—Phase 1b Study of Subcutaneous Isatuximab in Humans

This example describes a multi-center, open-label, phase 1b study to assess the pharmacokinetics, safety, and efficacy of subcutaneous and intravenous isatuximab in combination with pomalidomide and dexamethasone in patients with relapsed/refractory multiple myeloma (RRMM).

The instant study is designed to assess for the first time the SC administration of isatuximab. In addition, the SC formulation is not the same as the formulation used for IV dosing. Isatuximab SC in combination with pomalidomide and dexamethasone is administered in a similar patient population as in previous studies mentioned above. This study also includes cohorts with isatuximab IV administration to allow the assessment of safety and PK versus isatuximab SC.

Primary endpoints of the study are (i) to evaluate the safety and tolerability (including local injection site tolerability) of isatuximab administered subcutaneously (SC) using infusion pump versus isatuximab administered intravenously (IV); and (ii) to evaluate the pharmacokinetics of isatuximab when given SC and IV in combination with pomalidomide and dexamethasone. Secondary endpoints of the study include (i) estimation of absolute bioavailability of isatuximab SC and IV; (ii) to measure the CD38 receptor occupancy (RO) of isatuximab in plasma cells from bone marrow aspirate after SC administration versus IV administration; and (iii) to evaluate the efficacy of isatuximab SC/IV administration.

The study includes 5 cohorts of participants. Patients are randomized in Cohorts 1a (SC 1000 mg dose) or 1b (IV) (randomization ratio of 2:1). After evaluation of isatuximab SC safety, PK, and RO data in Cohort 1a, additional participants are randomized in Cohorts 2a or 2b (randomization ratio of 2:1) with a higher dose of isatuximab SC in Cohort 2a (1400 mg dose) and the same IV dose in Cohort 2b. A final review of safety, PK, and RO data after administration of isatuximab SC and IV is made once all patients in Cohorts 2a and 2b have completed Cycle 1 of the treatment. After confirmation of the recommended phase 2 dose (RP2D) level, an additional 22 patients are recruited in Cohort 2c and are administered isatuximab SC at this dose level. Table 31 describes treatment by cohort in more detail.

TABLE 31

| Cohort Treatment Details | | |
| --- | --- | --- |
| Cohort | Dose | Administration Route/Method |
| 1a (n = 8) | 1000 mg | SC/infusion pump (0.8 mL/min) |
| 1b (n = 4) | 10 mg/kg | IV |
| 2a (n = 8) | 1400 mg | SC/infusion pump (0.8 mL/min) |
| 2b (n = 4) | 10 mg/kg | IV |
| 2c (n = 22) | RP2D | SC/infusion pump (0.8 mL/min) |

Isatuximab is administered weekly for 4 weeks (Cycle 1) and on Day 1 and Day 15 of each subsequent cycle, in combination with pomalidomide and dexamethasone. Each cycle is 28 days in duration. All participants in the study continue treatment until disease progression, unacceptable adverse reaction, or other reason for discontinuation.

Cohorts 1a, 2a, and 2c receive by subcutaneous (SC) infusion a formulation of isatuximab comprising 140 mg/mL isatuximab, 9 mM histidine, 110 mM Arginine monohydrochloride, 2% (w/v) sucrose, and 0.4% (w/v) Poloxamer 188, pH 6.2. Cohorts 1a, 2a, and 2c also receive 4 mg pomalidomide orally (p.o.) on Days 1 to 21 every 28 day cycle; and dexamethasone 4 mg p.o. on Days 1, 8, 15, and 22 every 28 day cycle.

Cohorts 1b and 2b receive by intravenous (IV) infusion a different formulation of isatuximab comprising 20 mg/mL isatuximab, 20 mM histidine, 10% (w/v) sucrose, and 0.02% (w/v) polysorbate 80, pH 6.0. Cohorts 1b and 2b also receive 4 mg pomalidomide orally (p.o.) on Days 1 to 21 every 28 day cycle; and dexamethasone 4 mg p.o. on Days 1, 8, 15, and 22 every 28 day cycle.

The safety, PK, and RO data from Cycle 1 (first 4 weeks) of Cohort 1a and Cohort 2a are reviewed before proceeding to the Cohort 2a or 2c, respectively.

A review of safety, PK, and RO data collected in Cohorts 1 (a/b) and 2 (a/b) is used to support the selection of the most appropriate SC isatuximab dose RP2D.

An isatuximab dose of 1000 mg was selected as the starting dose based on PK modeling and simulations which demonstrated that even assuming 80% SC bioavailability, isatuximab concentrations (Trough plasma concentration [Ctrough] at Day 28) will be in a similar range as Day 28 concentrations observed following IV administration at 10 mg/kg and much lower than 20 mg/kg IV, which has been shown to be safe in the clinic. A lower dose than 1000 mg was not considered as the starting dose because of the PK non-linearity of isatuximab.

The selection of the 1400 mg dose for SC isatuximab is based on a population PK model built with IV data (n=127). This model has shown that 1400 mg SC isatuximab administered as QW×4/Q2W would maintain Ctrough above the levels reached following 10 mg/kg IV QW×4/Q2W, with the hypothesis of an absolute bioavailability ≥50%. The PK/PD analyses have demonstrated that Ctrough at 4 weeks is a significant predictor of the response (objective response rate, IV administration).

Inclusion criteria include the following:

Patients who have been previously diagnosed with multiple myeloma (MM) based on standard criteria and currently require treatment because MM has relapsed following a response, according to International Myeloma Working Group (IMWG) criteria.

Patients who have received at least 2 previous therapies including lenalidomide and a proteasome inhibitor and had demonstrated disease progression on last therapy or after completion of the last therapy; and Patients with measurable disease defined as at least one of the following:

Serum M protein ≥0.5 g/dL (≥5 g/L);

Urine M protein ≥200 mg/24 hours; and

Serum free light chain (FLC) assay: Involved FLC assay ≥10 mg/dL (≥100 mg/L) and an abnormal serum FLC ratio (<0.26 or >1.65).

Bone marrow and blood samples are collected for the following biomarker analyses:

CD38 receptor occupancy of isatuximab is measured in plasma cells from bone marrow aspirate and correlated with parameters of PK and clinical response. Bone marrow samples are collected at screening and at Day 1 of Cycle 2 (predose). This sample collection is stopped once RP2D the isatuximab SC dose has been selected (cohorts 1a/b and cohorts 2a/b only).

Minimal residual disease (MRD) is assessed by next generation sequencing in bone marrow aspirates and correlated with parameters of clinical response. Bone marrow samples are collected at screening for all participants and at the time of maximum confirmed response of either complete response (CR) or very good partial response (VGPR). Samples at screening are analyzed only for participants who will reach VGPR or better.

Potential isatuximab interference with the M-protein assessment in immunoelectrophoresis and immunofixation assays is assessed on serum sample using an assay that removes isatuximab interference.

The invention claimed is:

1. An antibody formulation suitable for subcutaneous administration comprising:
  (i) 125-155 mg/ml isatuximab, and
  (ii) excipients consisting of:
    (a) histidine,
    (b) 90-125 mM arginine (Arg),
    (c) sucrose,
    (c) 0.4% (w/v) Poloxamer 188,
  wherein the antibody formulation has a pH of 5.9-6.3 and a viscosity of at most 25 mPa·s at 20° C.

2. The antibody formulation of claim 1, wherein the Arg is at a concentration of 110 mM Arg.

3. The antibody formulation of claim 1, wherein the histidine is at a concentration of 9 mM histidine.

4. The antibody formulation of claim 1, wherein the antibody formulation comprises 140 mg/ml isatuximab.

5. The antibody formulation of claim 1, wherein the sucrose is at a concentration of 2% (w/v) sucrose.

6. The antibody formulation of claim 1, wherein the pH is 6.2-6.3.

7. The antibody formulation of claim 1, wherein the formulation has a viscosity of at most 14 mPa·s at 20° C.

8. The antibody formulation of claim 1, wherein the subcutaneous administration comprises a large-volume subcutaneous infusion.

9. The antibody formulation of claim 8, wherein the large-volume subcutaneous infusion comprises an infusion volume of 5 mL to 30 mL.

10. The antibody formulation of claim 9, wherein the large-volume subcutaneous infusion comprises an infusion volume of 10 mL to 15 mL.

11. The antibody formulation of claim 10, wherein the large-volume subcutaneous infusion comprises an infusion volume of 10 mL to 12 mL.

12. An antibody formulation suitable for subcutaneous administration, wherein the antibody formulation comprises:
  (i) 125-155 mg/ml isatuximab, and
  (ii) excipients consisting of:
    (a) histidine,
    (b) 90-125 mM arginine (Arg),
    (c) sucrose, and
    (d) Poloxamer 188,
  wherein the antibody formulation has a pH of 5.9-6.3 and wherein the subcutaneous administration comprises a large-volume subcutaneous infusion.

13. The antibody formulation of claim 12, wherein the large-volume subcutaneous infusion comprises an infusion volume of 5 mL to 30 mL.

14. The antibody formulation of claim 13, wherein the large-volume subcutaneous infusion comprises an infusion volume of 10 mL to 15 mL.

15. The antibody formulation of claim 14, wherein the large-volume subcutaneous infusion comprises an infusion volume of 10 mL to 12 mL.

16. A packaged pharmaceutical product comprising a sterile container or a device, the sterile container or device comprising a therapeutically effective amount of a formulation suitable for subcutaneous administration comprising:
  (i) 125-155 mg/ml isatuximab, and
  (ii) excipients consisting of:
    (a) histidine,
    (b) 90-125 mM arginine (Arg),
    (c) sucrose, and
    (d) 0.4% (w/v) Poloxamer 188,
  wherein the formulation has a pH of 5.9-6.3 and
  wherein the subcutaneous administration comprises a large-volume subcutaneous infusion.

17. The packaged pharmaceutical product of claim 16, wherein the large-volume subcutaneous infusion comprises an infusion volume of 10 mL to 12 mL.

18. The packaged pharmaceutical product of claim 16, wherein the formulation has a viscosity of at most 25 mPa's at 20° C.

19. The packaged pharmaceutical product of claim 16, wherein the device is selected from a syringe, a syringe driver, a pre-filled syringe, and an infusion pump.

20. An antibody formulation suitable for large volume subcutaneous administration, comprising:
  (i) 125-155 mg/ml isatuximab, and
  (ii) excipients consisting of:
    (a) 9 mM histidine,
    (b) 90-125 mM arginine (Arg),
    (c) 2% (w/v) sucrose, and
    (d) 0.4% (w/v) Poloxamer 188,
  wherein the antibody formulation does not include hyaluronidase; and
  wherein the large volume subcutaneous administration comprises an infusion volume of 10 mL to 12 mL.

21. An antibody formulation suitable for subcutaneous administration, comprising:
  (i) 125-155 mg/ml isatuximab, and
  (ii) excipients consisting of:
    (a) histidine,
    (b) 90-125 mM arginine (Arg),
    (c) sucrose, and
    (d) Poloxamer 188,
  wherein the antibody formulation has a pH of 5.9-6.3, wherein the subcutaneous administration comprises a large-volume subcutaneous infusion, and wherein the antibody formulation does not include hyaluronidase.

22. The antibody formulation of claim 21, wherein the formulation has a pH of 5.9-6.3 and a viscosity of at most 25 mPa·s at 20° C.

23. The antibody formulation of claim 21, wherein the antibody formulation has a viscosity of at most 14 mPa·s at 20° C.

24. The antibody formulation of claim 21, wherein the antibody formulation comprises 140 mg/ml isatuximab.

25. The antibody formulation of claim 21, wherein the large-volume subcutaneous infusion comprises an infusion volume of 5 mL to 30 mL.

26. The antibody formulation of claim 21, wherein the large-volume subcutaneous infusion comprises an infusion volume of 10 mL to 12 mL.

27. An antibody formulation suitable for subcutaneous administration, wherein the antibody formulation comprises:

(i) 125-155 mg/ml isatuximab; and (ii) excipients consisting of:

(a) 9 mM histidine, (b) 90-125 mM arginine, (c) 2% (w/v) sucrose, and (d) 0.4% (w/v) Poloxamer 188, and wherein the antibody formulation has a pH of 5.9-6.3 and a viscosity of at most 25 mPa·s at 20° C.

28. The antibody formulation of claim 27, wherein the Arg is at a concentration of 110 mM Arg.

29. The antibody formulation of claim 27, wherein the antibody formulation comprises 140 mg/ml isatuximab.

30. The antibody formulation of claim 29, wherein the pH is 6.2-6.3.

31. The antibody formulation of claim 29, wherein the antibody formulation has a viscosity of at most 14 mPa·s at 20° C.

\* \* \* \* \*

```
                        SEQUENCE LISTING

<160> NUMBER OF SEQ ID NOS: 10

<210> SEQ ID NO 1
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 1

Asp Tyr Trp Met Gln
1               5

<210> SEQ ID NO 2
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 2

Thr Ile Tyr Pro Gly Asp Gly Asp Thr Gly Tyr Ala Gln Lys Phe Gln
1               5                   10                  15

Gly

<210> SEQ ID NO 3
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 3

Gly Asp Tyr Tyr Gly Ser Asn Ser Leu Asp Tyr
1               5                   10

<210> SEQ ID NO 4
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 4
```

-continued

```
Lys Ala Ser Gln Asp Val Ser Thr Val Val Ala
1               5                   10

<210> SEQ ID NO 5
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 5

Ser Ala Ser Tyr Arg Tyr Ile
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 6

Gln Gln His Tyr Ser Pro Pro Tyr Thr
1               5

<210> SEQ ID NO 7
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 7

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
                20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
        50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120

<210> SEQ ID NO 8
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 8

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
                20                  25                  30
```

```
Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
        50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
                100                 105

<210> SEQ ID NO 9
<211> LENGTH: 450
<212> TYPE: PRT
<213> ORGANISM: Artificial sequence
<220> FEATURE:
<223> OTHER INFORMATION: Synthetic polypeptide

<400> SEQUENCE: 9

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
                20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
        50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
                100                 105                 110

Gly Thr Ser Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285
```

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
    435                 440                 445

Gly Lys
    450

<210> SEQ ID NO 10
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 10

Asp Ile Val Met Thr Gln Ser His Leu Ser Met Ser Thr Ser Leu Gly
1               5               10              15

Asp Pro Val Ser Ile Thr Cys Lys Ala Ser Gln Asp Val Ser Thr Val
                20              25              30

Val Ala Trp Tyr Gln Gln Lys Pro Gly Gln Ser Pro Arg Arg Leu Ile
            35              40              45

Tyr Ser Ala Ser Tyr Arg Tyr Ile Gly Val Pro Asp Arg Phe Thr Gly
    50              55              60

Ser Gly Ala Gly Thr Asp Phe Thr Phe Thr Ile Ser Ser Val Gln Ala
65              70              75              80

Glu Asp Leu Ala Val Tyr Tyr Cys Gln Gln His Tyr Ser Pro Pro Tyr
            85              90              95

Thr Phe Gly Gly Gly Thr Lys Leu Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
            130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190
```

```
Ala Cys Glu Val Thr His Gln Gly Leu Ser Ser Pro Val Thr Lys Ser
        195                 200                 205

Phe Asn Arg Gly Glu Cys
    210
```